(12) United States Patent
Singletary et al.

(10) Patent No.: US 6,423,886 B1
(45) Date of Patent: Jul. 23, 2002

(54) STARCH SYNTHASE POLYNUCLEOTIDES AND THEIR USE IN THE PRODUCTION OF NEW STARCHES

(75) Inventors: George W. Singletary, Ankeny; Lan Zhou, Johnston, both of IA (US)

(73) Assignee: Pioneer Hi-Bred International, Inc., Des Moines, IA (US)

( * ) Notice: Subject to any disclaimer, the term of this patent is extended or adjusted under 35 U.S.C. 154(b) by 0 days.

(21) Appl. No.: 09/388,743

(22) Filed: Sep. 2, 1999

(51) Int. Cl.[7] .................. C12N 15/29; C12N 15/82; C12P 19/04; A01H 5/00; A01H 5/10
(52) U.S. Cl. .................. 800/284; 800/286; 800/305; 800/306; 800/312; 800/314; 800/315; 800/317.1; 800/317.2; 800/317.4; 800/320; 800/320.1; 800/320.2; 800/320.3; 800/322; 435/69.1; 435/320.1; 435/419; 536/23.6; 536/24.5; 536/23.2
(58) Field of Search .................. 536/23.6, 24.5, 536/23.2; 435/69.1, 320.1, 419; 800/284, 286, 305, 306, 312, 314, 317.1, 315, 317.2, 317.4, 320, 320.1–320.3, 322

(56) References Cited

U.S. PATENT DOCUMENTS 5,824,790 A 10/1998 Keeling et al. ............ 536/23.6
6,130,367 A * 10/2000 Kossmann .................. 800/284

FOREIGN PATENT DOCUMENTS

| CA | 2205118 | 5/1996 | ........... C12N/15/54 |
| WO | WO 97/20936 | 6/1997 | ........... C12N/15/52 |
| WO | WO 97/26362 | 7/1997 | ........... C12N/15/82 |
| WO | WO 97/45545 | 12/1997 | ........... C12N/15/54 |

OTHER PUBLICATIONS

Kossmann, J. et al., "Transgenic plants as a tool to understand starch biosynthesis." 1995, Progress in Biotechnol., vol. 10, pp. 271–278.*
Denyer, K. et al. "Identification of multiple isoforms of soluble and granule–bound starch synthase in developing wheat endosperm." 1995, Planta, vol. 196, pp. 256–265.*
Nakatani, M. et al., "Relationship between Starch Content and Activity of Starch Synthase and ADP–glucose Pyrophosphorylase in Tuberous Root of Sweet Potato." 1992, Jpn. J. Crop Sci., vol. 61, pp. 463–468.*
Salehuzzaman, S. et al., "Isolation and characterization of a cDNA encoding granule–bound starch synthase in cassava (*Manihot esculenta* Crantz) and its antisense expression in potato." 1993, Plant Molecular Biology, vol. 23, pp. 947–962.*
Dry, I. et al., "Characterization of cDNAs encoding two isoforms of granule–bound starch synthase which show differential expression in developing storage organs of pea and potato," 1992, The Plant Journal, vol. 2, pp. 193–202.*

* cited by examiner

*Primary Examiner*—David T. Fox
(74) *Attorney, Agent, or Firm*—Pioneer Hi-Bred International, Inc.

(57) ABSTRACT

The invention provides isolated nucleic acids and their encoded proteins that are involved in starch biosynthesis. The invention further provides recombinant expression cassettes, host cells, transgenic plants, and antibody compositions. The present invention provides methods and compositions relating to altering the amount and/or morphology of starch in plants.

56 Claims, No Drawings

STARCH SYNTHASE POLYNUCLEOTIDES AND THEIR USE IN THE PRODUCTION OF NEW STARCHES

TECHNICAL FIELD

The present invention relates generally to plant molecular biology. More specifically, it relates to nucleic acids and methods for modulating their expression in plants.

BACKGROUND OF THE INVENTION

Starches are polymers of glucose molecules produced and stored only in the chloroplasts and amyloplasts of plants. Most of the starch produced in the world is used as food, but about one-third of the total production is employed for a variety of industrial purposes that take advantage of starch's unique properties. These properties (e.g. viscosity, gelatinization temperature) vary greatly with the plant source and affect the usefulness of the starch for food and nonfood products. (Sivak and Preiss, *Advances in Food and Nutrition Research*, Vol. 41. Academic Press, 1998, p. 163.) The properties of a starch are determined by the structure of its constituent granules and the polymers from which the granules are formed. Molecular structure is, in turn, dependent largely upon the presence and activity of specific isozymes of starch synthase. Genes encoding the starch synthase enzymes are therefore of interest.

The presence or absence of specific starch synthase isozymes in tissues can have profound effects upon the nature of starch polymers and granules produced in plants, although the exact role of different synthase isozymes in defining the specificity of amylose, amylopectin and granule properties is still unclear. Recent research suggests that the contribution of a starch synthase isozyme is determined not only by intrinsic properties of the enzyme but also by interactions among various synthases, branching enzymes, and/or debranching enzymes. Thus, the genetic, environmental, and developmental backgrounds in which a particular starch synthase isozyme is expressed affect the role of that isozyme in dictating distinct features of starch. This implies that almost any manipulation of combinations of starch synthesizing enzymes may have surprising and potentially useful results. (Smith, A. M. *Current Opinion in Plant Biology* 2:223–229 (1999))

When a mutation affecting a particular starch biosynthetic enzyme results in changes in the appearance of a seed, the resulting changes in starch structure may be subtle: for example, a slight decrease in the average chain length of amylopectin or a small increase in the proportion of amylose to amylopectin. (Sivak and Preiss, supra, p. 29.) However, even small changes in the molecular structure of a starch may have significant effects on its industrial utility. Identification of enzymatic changes and of the consequent modification of starch will result in enhanced diversity of starch functionalities for industrial purposes.

Certain genes encoding starch synthases have been identified and cloned, and modifications of starch content using these genes have been attempted or accomplished. See, for example, U.S. Pat. No. 5,824,798; WO Publication No. 96/15248; WO Publication No. 97/45545; WO Publication No. 97/26362; and WO Publication No. 97/20936.

Starch synthase enzymes utilize ADPglucose and/or UDPglucose in a polymerization reaction. The glycosyl portion of the substrate is transferred to, in most cases, preexisting maltooligosaccharides or polymers of α-(1,4) or mixed α-(1,4) and α-(1,6) linkages. In other words, these enzymes are involved in the biosynthesis of amylose [α-(1, 4) polymer] and amylopectin [polymer of α-(1,4) branched with α-(1–4,6) linkages], the primary types of molecules occurring in starch granules.

Starch composition varies with species and tissue. Maize starch stored in the endosperm is typically composed of 28% amylose and 72% amylopectin. Amylose of maize starch has an average degree of polymerization (number-average; $DP_n$) of 960 and an average chain length (CL) of 305. Maize amylopectin, on the other hand, has a $DP_n$ of $10.2 \times 10^3$ and a CL of 22. (Morrison et al., "Starch" in Dey & Harborne, *Methods in Plant Biochemistry* (London, Academic Press, 1990), pp. 323–352).

The different structures of amylose and amylopectin confer distinctive properties to these polysaccharides. For example, the amylose fraction of starch will precipitate from an aqueous solution over time as the linear amylose molecules align themselves parallel to each other and become held together by hydrogen bonds. This precipitation is known as retrogradation. Amylopectin, on the other hand, does not readily form intermolecular complexes and is more stable in aqueous solutions. However, the crystalline nature of starch is due to the presence of amylopectin and not to amylose. This is contrary to the general principle that branching in a molecule is detrimental to crystallization. (Sivak and Preiss, supra, pp. 20–22) Indeed, the chain length of amylopectin is a basic factor in the determination of the crystalline type of the starch. (Hizukuri, S., *Carbohydrate Research* 141, pp. 295–306 (1985))

The ease of isolation of starch granules for food and industrial purposes is affected by starch composition. In each bushel of maize processed, roughly 2.2 to 3.4 pounds of starch are unrecoverable. This represents a 6% to 8% loss of potential starch yield. Thus, a need exists for improved yield of starch from maize grain; alteration of granule size and/or density could improve this processing yield.

Starches with unusual, desirable functional properties may be currently available only in small quantities, or in plants or plant parts not commonly processed. Therefore, a need exists to develop plants, especially cereals, potato, or cassava, capable of synthesizing unusual starch for use in specific food and non-food industrial applications.

SUMMARY OF THE INVENTION

It is an object of the present invention to provide nucleic acids and polypeptides relating to the biosynthesis of starch.

It is another object of the present invention to provide nucleic acids and polypeptides that can be used to identify proteins involved in starch biosynthesis.

It is another object of the present invention to provide antigenic fragments of the polypeptides of the present invention.

It is another object of the present invention to provide transgenic plants comprising the nucleic acids of the present invention.

It is another object of the present invention to provide methods for modulating, in a transgenic plant, the expression of the nucleic acids of the present invention.

It is another object of the present invention to provide a method for modulating the type and level of starch synthase in a plant.

It is another object of the present invention to provide a method for modulating the type and level of starch in a plant.

It is another object of the present invention to improve the industrial processing yield of starch from maize grain by altering starch granule size and/or density.

It is another object of the present invention to provide plants, especially maize, wheat, sorghum, barley, millet, rice, potato, or cassava plants, capable of synthesizing unusual starch with desirable functional properties for use in specific food and non-food industrial applications.

It is another object of the present invention to provide plants capable of synthesizing starch with altered granule sizes.

It is another object of the present invention to provide plants capable of synthesizing starch with altered degrees of crystallinity.

It is another object of the present invention to provide plants capable of synthesizing starch with altered densities.

It is another object of the present invention to provide plants capable of synthesizing starch with altered digestibilities.

It is another object of the present invention to provide plants capable of synthesizing starch with altered levels of covalently bound phosphate.

It is another object of the present invention to provide plants capable of synthesizing starch with altered patterns of branching and/or average chain lengths.

It is another object of the present invention to provide plants capable of synthesizing starch with altered temperatures of gelatinization.

It is another object of the present invention to provide plants capable of synthesizing starch with altered degrees of polymerization and retrogradation.

Therefore, in one aspect, the present invention relates to an isolated nucleic acid comprising a member selected from the group consisting of:

(a) a polynucleotide that encodes a polypeptide of SEQ ID NO: 2, 6, 10, 14, 18, 22, or 26;

(b) a polynucleotide amplified from a *Zea mays* nucleic acid library using one or more primers selected from SEQ ID NOS: 3, 4, 7, 8, 11, 12, 15, 16, 19, 20, 23, 24, 27, and 28;

(c) a polynucleotide comprising at least 20 contiguous bases of SEQ ID NO: 1, 5, 9, 13, 17, 21, or 25;

(d) a polynucleotide encoding a starch synthase from *Curcuma zedoaria, Maranta arundinacea, Canna edulis, Typha latifolia,* or *Tulipa fosteriana;*

(e) a polynucleotide having at least 73% sequence identity to SEQ ID NO: 1, 5, 9, 13, 17, 21, or 25, wherein the % sequence identity is based on the entire coding sequence and is determined by BLAST 2.0 using default parameters;

(f) a polynucleotide comprising at least 25 nucleotides in length which hybridizes under low stringency conditions to a polynucleotide having the sequence set forth in SEQ ID NO: 1, 5, 9, 13, 17, 21, or 25, wherein the conditions include a wash in 0.1×SSC at 60° C.;

(g) a polynucleotide comprising the coding sequence set forth in SEQ ID NO: 1, 5, 9, 13, 17, 21, or 25; and (h) a polynucleotide complementary to a polynucleotide of (a) through (g).

Other aspects of the present invention include expression cassettes comprising the nucleic acid operably linked to a promoter, host cells transfected with the expression cassette, and transgenic plants and seeds comprising the expression cassette.

Also provided is an isolated protein comprising a member selected from the group consisting of:

(a) a polypeptide comprising at least 25 contiguous amino acids of SEQ ID NO: 2, 6, 10, 14, 18, 22, or 26;

(b) a polypeptide which is a starch synthase protein from *Curcuma zedoaria, Maranta arundinacea, Canna edulis, Typha latifolia,* or *Tulipa fosteriana;*

(c) a polypeptide comprising at least 73% sequence identity to SEQ ID NO: 2, 6, 10, 14, 18, 22, or 26, wherein the % sequence identity is based on the entire sequence and is determined by BLAST 2.0 using default parameters;

(d) a polypeptide encoded by a nucleic acid of claim 1; and (e) a polypeptide characterized by SEQ ID NO: 2, 6, 10, 14, 18, 22, or 26.

In a further aspect, the present invention relates to a method of modulating expression of the nucleic acids in a plant, comprising the steps of:

(a) transforming a plant cell with an expression cassette comprising a nucleic acid of the present invention operably linked to a promoter in sense or antisense orientation;

(b) growing the plant cell under plant growing conditions to produce a regenerated plant capable of expressing the nucleic acid for a time sufficient to modulate expression of the nucleic acids in the plant compared to a corresponding non-transformed plant.

Expression of the nucleic acids encoding the proteins of the present invention can be increased or decreased relative to a non-transformed control plant.

DETAILED DESCRIPTION OF THE INVENTION

The genes presently claimed encode starch synthases derived from plant species known to contain starch with unusual properties. Expression of these genes in other species, such as maize, wheat, sorghum, barley, millet, rice, potato, or cassava, is expected to modify the structure of starch polymers and granules in those species. The result will be improved industrial isolation of starch and the production of starch with novel functional properties currently unobtainable in agronomic crops.

Starch granules of *Curcuma zedoaria* have an unusual elongated morphology, are about 70$\mu$ in length and 14$\mu$ in thickness, and have a temperature of gelatinization of about 83° C. (Jane, J., et al., *Starch* 46:121–129 (1994); Reichert, E. T., *The Differentiation and Specificity of Starches in Relation to Genera, Species,* Etc. Carnegie Institution, Washington, D.C. (1913)). In contrast, maize granules have a round, polygonal form; range in size from about 2$\mu$ to 30$\mu$, with an average diameter of 10$\mu$ (Swinkels, J. J. M. *Starch* 37:1–5 (1985)); and gelatinize at about 65° C.

Tulip starch contains approximately 27% amylose (Deatherage, W. L., et al. *Trans. Am. Assoc. Cereal Chem.* 13:31–42 (1955)) and has a granule size of roughly 6$\mu$ to 50$\mu$, with an average diameter of 35$\mu$. Most notably, tulip starch has a gelatinization temperature of about 50° C., (Reichert, E. T., supra) and its amylopectin has a chain length longer than that of maize starch. Tulip starch also has a pattern of branching different from that of maize starch. (Hizukuri, S., supra).

Expression of the isolated starch synthase genes of the present application in plants, especially maize, wheat, sorghum, barley, millet, rice, potato, or cassava plants, could allow the production of starch with unique functional properties not currently available. For example, it is expected that expression of the present starch synthase genes in maize could:

(1) Lead to the biosynthesis of a population of starch granules that are, on average, larger than the granules which occur in normal maize. For example, the starch granules could range in size from $35\mu$ to $100\mu$, from $40\mu$ to $100\mu$, or from $50\mu$ to $100\mu$.

(2) Lead to the biosynthesis of starch granules that have greater or lesser degrees of crystallinity and gelatinization temperatures and, in turn, elevated or reduced densities. Greater density could facilitate recovery of starch in wet milling, and increased gelatinization temperatures could allow the use of higher temperatures (i.e. reaction rates) in chemical modification of starch. Starch of decreased density or gelatinization temperature could be more digestible as a food material or in feedstuffs and could offer process efficiency in the conversion of intact granules into gelatinized granule fragments.

(3) Lead to the biosynthesis of starch granules that have a greater degree of crystallinity and display reduced digestibility. Such a starch could have application in low-calorie foods and/or sport drinks which help maintain lower, stable glycemic indices.

(4) Result in higher levels of covalently bound phosphate by way of a synergistic interaction with the native mechanism which normally allows only low levels of phosphorylation.

(5) Produce altered patterns of branching and modified average chain lengths in amylopectin which could produce starch that has a reduced temperature of gelatinization.

(6) Produce amylose of lower or higher degree of polymerization than in normal maize starch and lead to altered rates of retrogradation.

Definitions

The term "isolated" refers to material, such as a nucleic acid or a protein, which is: (1) substantially or essentially free from components which normally accompany or interact with it as found in its natural environment. The isolated material optionally comprises material not found with the material in its natural environment; or (2) if the material is in its natural environment, the material has been synthetically altered or synthetically produced by deliberate human intervention and/or placed at a different location within the cell. The synthetic alteration or creation of the material can be performed on the material within or apart from its natural state. For example, a naturally-occurring nucleic acid becomes an isolated nucleic acid if it is altered or produced by non-natural, synthetic methods, or if it is transcribed from DNA which has been altered or produced by non-natural, synthetic methods. The isolated nucleic acid may also be produced by the synthetic re-arrangement ("shuffling") of a part or parts of one or more allelic forms of the gene of interest. Likewise, a naturally-occurring nucleic acid (e.g., a promoter) becomes isolated if it is introduced to a different locus of the genome. Nucleic acids which are "isolated," as defined herein, are also referred to as "heterologous" nucleic acids.

As used herein, "polypeptide" means proteins, protein fragments, modified proteins, amino acid sequences and synthetic amino acid sequences. The polypeptide can be glycosylated or not.

As used herein, "plant" includes but is not limited to plant cells, plant tissue and plant seeds.

As used herein, "promoter" includes reference to a region of DNA upstream from the start of transcription and involved in recognition and binding of RNA polymerase and other proteins to initiate transcription.

By "fragment" is intended a portion of the nucleotide sequence or a portion of the amino acid sequence and hence protein encoded thereby. Preferably fragments of a nucleotide sequence may encode protein fragments that retain the biological activity of the native nucleic acid. However, fragments of a nucleotide sequence which are useful as hybridization probes generally do not encode fragment proteins retaining biological activity. Fragments of a nucleotide sequence are generally greater than 10 nucleotides, preferably at least 20 nucleotides and up to the entire nucleotide sequence encoding the proteins of the invention. Generally probes are less than 1000 nucleotides and preferably less than 500 nucleotides. Fragments of the invention include antisense sequences used to decrease expression of the inventive nucleic acids. Such antisense fragments may vary in length ranging from at least about 20 nucleotides, about 50 nucleotides, about 100 nucleotides, up to and including the entire coding sequence.

By "variants" is intended substantially similar sequences. Generally, nucleic acid sequence variants of the invention will have at least 50%, 60%, 70%, or preferably 80%, more preferably at least 90% and most preferably at least 95% sequence identity to the native nucleotide sequence.

Generally, polypeptide sequence variants of the invention will have at least about 55%, 60%, 70%, 80%, or preferably at least about 90% and more preferably at least about 95% sequence identity to the native protein.

As used herein, "sequence identity" or "identity" in the context of two nucleic acid or polypeptide sequences includes reference to the residues in the two sequences that are the same when aligned for maximum correspondence over a specified comparison window. An indication that two peptide sequences are substantially identical is that one peptide is immunologically reactive with antibodies raised against the second peptide. A polypeptide is substantially identical to a second polypeptide, for example, where the two polypeptides differ only by a conservative substitution.

Methods of alignment of sequences for comparison are well-known in the art. For purposes of defining the present invention, the BLAST 2.0 suite of programs using default parameters is used. Altschul et al., *Nucleic Acids Res.* 25:3389–3402 (1997). Software for performing BLAST analyses is publicly available, e.g., through the National Center for Biotechnology Information (http://www.ncbi.nlm.nih.gov/).

By "functional equivalent, variant, or derivative" is intended a sequence that produces a protein having substantially the same biological effect as the native protein of interest.

Nucleic Acids

The isolated nucleic acids of the present invention can be made using (a) standard recombinant methods, (b) synthetic techniques, or (c) combinations thereof. The isolated nucleic acid may also be produced by the synthetic rearrangement ("shuffling") of a part or parts of one or more allelic forms of the gene of interest. Sequence shuffling is described in PCT publication No. WO97/20078. See also, Zhang, J. H., et al., *Proc. Natl. Acad. Sci. USA* 94:45044509 (1997).

In some embodiments, the polynucleotides of the present invention will be cloned, amplified, or otherwise constructed from a plant, including potato, cassava, maize, soybean, sunflower, canola, alfalfa, cotton, Arabidopsis, tomato, pepper, apple, spinach, and lettuce. In preferred embodiments the plant is *Curcuma zedoaria* or other species of the genus Curcuma; *Tulipa fosteriana* or other species of the genus Tulipa; *Maranta arundinacea* or other species of the genus Maranta; *Canna edulis* or other species of the genus Canna; *Typha latifolia* or other species of the genus Typha. Source tissues for isolated polynucleotides are preferably starchy plant parts, including tuber, root, and rhizome.

Functional fragments included in the invention can be obtained using primers that selectively hybridize under stringent conditions. Primers are generally at least 12 bases in length and can be as high as 200 bases, but will generally be from 15 to 75, preferably from 15 to 50. Functional fragments can be identified using a variety of techniques such as restriction analysis, Southern analysis, primer extension analysis, and DNA sequence analysis.

The present invention includes a plurality of polynucleotides that encode for the identical amino acid sequence. The degeneracy of the genetic code allows for such "silent variations" which can be used, for example, to selectively hybridize and detect allelic variants of polynucleotides of the present invention. Additionally, the present invention includes isolated nucleic acids comprising allelic variants. The term "allele" as used herein refers to a related nucleic acid of the same gene.

Variants of nucleic acids included in the invention can be obtained, for example, by oligonucleotide-directed mutagenesis, linker-scanning mutagenesis, mutagenesis using the polymerase chain reaction, and the like. See, for example, Ausubel, pages 8.0.3–8.5.9. Also, see generally, McPherson (ed.), *DIRECTED MUTAGENESIS: A Practical approach,* (IRL Press, 1991). Thus, the present invention also encompasses DNA molecules comprising nucleotide sequences that have substantial sequence similarity with the inventive sequences.

Variants included in the invention may contain individual substitutions, deletions or additions to the nucleic acid or polypeptide sequences. Such changes will alter, add or delete a single amino acid or a small percentage of amino acids in the encoded sequence. Variants are referred to as "conservatively modified variants" where the alteration results in the substitution of an amino acid with a chemically similar amino acid. When the nucleic acid is prepared or altered synthetically, advantage can be taken of known codon preferences of the intended host.

The present invention also includes the use of 5' and/or 3' UTR regions for modulation of translation of heterologous coding sequences. Positive sequence motifs include translational initiation consensus sequences (Kozak, *Nucleic Acids Res.*15:8125 (1987)) and the 7-methylguanosine cap structure (Drummond et al., *Nucleic Acids Res.* 13:7375 (1985)). Negative elements include stable intramolecular 5' UTR stem-loop structures (Muesing et al., *Cell* 48:691 (1987)) and AUG sequences or short open reading frames preceded by an appropriate AUG in the 5' UTR (Kozak, supra, Rao et al., *Mol. and Cell. Biol.* 8:284 (1988)).

Further, the polypeptide-encoding segments of the polynucleotides of the present invention can be modified to alter codon usage. Altered codon usage can be employed to alter translational efficiency and/or to optimize the coding sequence for expression in a desired host or to optimize the codon usage in a heterologous sequence for expression in maize. Codon usage in the coding regions of the polynucleotides of the present invention can be analyzed statistically using commercially available software packages such as "Codon Preference" available from the University of Wisconsin Genetics Computer Group (see Devereaux et al., *Nucleic Acids Res.* 12:387–395 (1984)) or MacVector 4.1 (Eastman Kodak Co., New Haven, Conn.).

For example, the inventive nucleic acids can be optimized for enhanced expression in organisms of interest. See, for example, EPA0359472; WO91/16432; Perlak et al., *Proc. Natl. Acad. Sci. USA* 88:3324–3328 (1991); and Murray et al., *Nucleic Acids Res.* 17:477–498 (1989). In this manner, the genes can be synthesized utilizing species-preferred codons. See, for example, Murray et al., *Nucleic Acids Res.* 17:477–498 (1989), the disclosure of which is incorporated herein by reference.

The present invention provides subsequences comprising isolated nucleic acids containing at least 16 contiguous bases of the inventive sequences. For example the isolated nucleic acid includes those comprising at least 20, 25, 30, 40, 50, 60, 75 or 100 contiguous nucleotides of the inventive sequences. Subsequences of the isolated nucleic acid can be used to modulate or detect gene expression by introducing into the subsequences compounds which bind, intercalate, cleave and/or crosslink to nucleic acids.

The nucleic acids of the invention may conveniently comprise a multi-cloning site comprising one or more endonuclease restriction sites inserted into the nucleic acid to aid in isolation of the polynucleotide. Also, translatable sequences may be inserted to aid in the isolation of the translated polynucleotide of the present invention. For example, a hexa-histidine marker sequence provides a convenient means to purify the proteins of the present invention.

A polynucleotide of the present invention can be attached to a vector, adapter, promoter, transit peptide or linker for cloning and/or expression of a polynucleotide of the present invention. Additional sequences may be added to such cloning and/or expression sequences to optimize their function in cloning and/or expression, to aid in isolation of the polynucleotide, or to improve the introduction of the polynucleotide into a cell. Use of cloning vectors, expression vectors, adapters, and linkers is well known and extensively described in the art. For a description of such nucleic acids see, for example, Stratagene Cloning Systems, Catalogs 1995, 1996, 1997 (La Jolla, Calif.); and, Amersham Life Sciences, Inc, Catalog '97 (Arlington Heights, Ill.).

The isolated nucleic acid compositions of this invention, such as RNA, cDNA, genomic DNA, or a hybrid thereof, can be obtained from plant biological sources using any number of cloning methodologies known to those of skill in the art. In some embodiments, oligonucleotide probes that selectively hybridize, under stringent conditions, to the polynucleotides of the present invention are used to identify the desired sequence in a cDNA or genomic DNA library.

Exemplary total RNA and mRNA isolation protocols are described in *Plant Molecular Biology: A Laboratory Manual,* Clark, Ed., Springer-Verlag, Berlin (1997); and, *Current Protocols in Molecular Biology,* Ausubel, et al., Eds., Greene Publishing and Wiley-Interscience, New York (1995). Total RNA and mRNA isolation kits are commercially available from vendors such as Stratagene (La Jolla, Calif.), Clonetech (Palo Alto, Calif.), Pharmacia (Piscataway, N.J.), and 5'-3' (Paoli, P A). See also, U.S. Pat. Nos. 5,614,391; and, 5,459,253.

Typical cDNA synthesis protocols are well known to the skilled artisan and are described in such standard references as: *Plant Molecular Biology: A Laboratory Manual,* Clark, Ed., Springer-Verlag, Berlin (1997); and, *Current Protocols in Molecular Biology,* Ausubel, et al., Eds., Greene Publishing and Wiley-Interscience, New York (1995). cDNA synthesis kits are available from a variety of commercial vendors such as Stratagene or Pharmacia.

An exemplary method of constructing a greater than 95% pure full-length cDNA library is described by Carninci et al.,*Genomics* 37:327–336 (1996). Other methods for producing full-length libraries are known in the art. See, e.g., Edery et al., *Mol. Cell Biol.*15(6):3363–3371 (1995); and, PCT Application WO 96/34981.

It is often convenient to normalize a cDNA library to create a library in which each clone is more equally represented. A number of approaches to normalize cDNA libraries are known in the art. Construction of normalized libraries is described in Ko, *Nucl. Acids. Res.* 18(19):5705–5711 (1990); Patanjali et al., *Proc. Natl. Acad. USA* 88:1943–1947 (1991); U.S. Pat. No. 5,482,685 and 5,637,685; and Soares et al., *Proc. Natl. Acad. Sci. USA* 91:9228–9232 (1994).

Subtracted cDNA libraries are another means to increase the proportion of less abundant cDNA species. See, Foote et al. in, *Plant Molecular Biology: A Laboratory Manual*, Clark, Ed., Springer-Verlag, Berlin (1997); Kho and Zarbl, *Technique*, 3(2):58–63 (1991); Sive and St. John, *Nucl. Acids Res.* 16(22):10937 (1988); *Current Protocols in Molecular Biology*, Ausubel, et al., Eds., Greene Publishing and Wiley-Interscience, New York (1995); and, Swaroop et al., *Nucl. Acids Res.* 19(8):1954 (1991). cDNA subtraction kits are commercially available. See, e.g., PCR-Select (Clontech).

To construct genomic libraries, large segments of genomic DNA are generated by random fragmentation. Examples of appropriate molecular biological techniques and instructions are found in Sambrook, et al., *Molecular Cloning: A Laboratory Manual*, 2nd Ed., Cold Spring Harbor Laboratory Vols. 1–3 (1989), Methods in Enzymology, Vol. 152: *Guide to Molecular Cloning Techniques*, Berger and Kimmel, Eds., San Diego: Academic Press, Inc. (1987), *Current Protocols in Molecular Biology*, Ausubel, et al., Eds., Greene Publishing and Wiley-Interscience, New York (1995); *Plant Molecular Biology: A Laboratory Manual*, Clark, Ed., Springer-Verlag, Berlin (1997). Kits for construction of genomic libraries are also commercially available.

The cDNA or genomic library can be screened using a probe based upon the sequence of a nucleic acid of the present invention such as those disclosed herein. Probes may be used to hybridize with genomic DNA or cDNA sequences to isolate homologous genes in the same or different plant species. Those of skill in the art will appreciate that various degrees of stringency of hybridization can be employed in the assay; and either the hybridization or the wash medium can be stringent. The degree of stringency can be controlled by temperature, ionic strength, pH and the presence of a partially denaturing solvent such as formamide.

Typically, stringent hybridization conditions will be those in which the salt concentration is less than about 1.5 M Na ion, typically about 0.01 to 1.0 M Na ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Typically the hybridization will be conducted for about 4 to about 12 hours.

Preferably the hybridization is conducted under low stringency conditions which include hybridization with a buffer solution of 30% formamide, 1 M NaCl, 1% SDS (sodium dodecyl sulfate) at 37° C., and a wash in 1× to 2×SSC (20×SSC=3.0 M NaCl/0.3 M trisodium citrate) at 50° C. More preferably the hybridization is conducted under moderate stringency conditions which include hybridization in 40% formamide, 1 M NaCl, 1% SDS at 37° C., and a wash in 0.5× to 1×SSC at 55° C. Most preferably the hybridization is conducted under high stringency conditions which include hybridization in 50% formamide, 1 M NaCl, 1% SDS at 37° C., and a wash in 0.1×SSC at 60° C. Typically the hybridization will be conducted for about 4 to about 12 hours.

An extensive guide to the hybridization of nucleic acids is found in Tijssen, *Laboratory Techniques in Biochemistry and Molecular Biology—Hybridization with Nucleic Acid Probes*, Part I, Chapter 2 *"Overview of principles of hybridization and the strategy of nucleic acid probe assays"*, Elsevier, N.Y. (1993); and *Current Protocols in Molecular Biology*, Chapter 2, Ausubel, et al., Eds., Greene Publishing and Wiley-Interscience, New York (1995). Often, cDNA libraries will be normalized to increase the representation of relatively rare cDNAs.

The nucleic acids of the invention can be amplified from nucleic acid samples using amplification techniques. For instance, polymerase chain reaction (PCR) technology can be used to amplify the sequences of polynucleotides of the present invention and related genes directly from genomic DNA or cDNA libraries. PCR and other in vitro amplification methods may also be useful, for example, to clone nucleic acid sequences that code for proteins to be expressed, to make nucleic acids to use as probes for detecting the presence of the desired mRNA in samples, for nucleic acid sequencing, or for other purposes.

Examples of techniques useful for in vitro amplification methods are found in Berger, Sambrook, and Ausubel, as well as Mullis et al., U.S. Pat. No. 4,683,202 (1987); and, *PCR Protocols A Guide to Methods and Applications*, Innis et al., Eds., Academic Press Inc., San Diego, Calif. (1990). Commercially available kits for genomic PCR amplification are known in the art. See, e.g., Advantage-GC Genomic PCR Kit (Clontech). The T4 gene 32 protein (Boehringer Mannheim) can be used to improve yield of long PCR products.

PCR-based screening methods have also been described. Wilfinger et al. describe a PCR-based method in which the longest cDNA is identified in the first step so that incomplete clones can be eliminated from study. *BioTechniques*, 22(3): 481–486 (1997).

In one aspect of the invention, nucleic acids can be amplified from a plant nucleic acid library. The nucleic acid library may be a cDNA library, a genomic library, or a library generally constructed from nuclear transcripts at any stage of intron processing. Libraries can be made from a variety of plant tissues.

Alternatively, the sequences of the invention can be used to isolate corresponding sequences in other organisms, particularly other plants, more particularly, other monocots. In this manner, methods such as PCR, hybridization, and the like can be used to identify such sequences having substantial sequence similarity to the sequences of the invention. See, for example, Sambrook et al. (1989) *Molecular Cloning: A Laboratory Manual* (2d ed., Cold Spring Harbor Laboratory Press, Plainview, N.Y.). and Innis et al. (1990), *PCR Protocols: A Guide to Methods and Applications* (Academic Press, New York). Coding sequences isolated based on their sequence identity to the entire inventive coding sequences set forth herein or to fragments thereof are encompassed by the present invention.

The isolated nucleic acids of the present invention can also be prepared by direct chemical synthesis by methods such as the phosphotriester method of Narang et al., *Meth. Enzymol.* 68:90–99 (1979); the phosphodiester method of Brown et al., *Meth. Enzymol.* 68:109–151 (1979); the diethylphosphoramidite method of Beaucage et al., *Tetra. Lett.* 22:1859–1862 (1981); the solid phase phosphoramidite triester method described by Beaucage and Caruthers, *Tetra.*

Letts. 22(20):1859–1862 (1981), e.g., using an automated synthesizer, e.g., as described in Needham-VanDevanter et al., *Nucleic Acids Res.*, 12:6159–6168 (1984); and, the solid support method of U.S. Pat. No. 4,458,066. Chemical synthesis generally produces a single stranded oligonucleotide. This may be converted into double stranded DNA by hybridization with a complementary sequence, or by polymerization with a DNA polymerase using the single strand as a template. One of skill will recognize that while chemical synthesis of DNA is limited to sequences of about 100 bases, longer sequences may be obtained by the ligation of shorter sequences.

Expression Cassettes

In another embodiment expression cassettes comprising isolated nucleic acids of the present invention are provided. An expression cassette will typically comprise a polynucleotide of the present invention operably linked to transcriptional initiation regulatory sequences which will direct the transcription of the polynucleotide in the intended host cell, such as tissues of a transformed plant.

The construction of expression cassettes that can be employed in conjunction with the present invention is well known to those of skill in the art in light of the present disclosure. See, e.g., Sambrook, et al.; *Molecular Cloning: A Laboratory Manual;* Cold Spring Harbor, N.Y.; (1989); Gelvin, et al.; *Plant Molecular Biology Manual;* (1990); *Plant Biotechnology: Commercial Prospects and Problems,* eds. Prakash, et al.; Oxford & IBH Publishing Co.; New Delhi, India; (1993); and Heslot, et al.; *Molecular Biology and Genetic Engineering of Yeasts;* CRC Press, Inc., USA; (1992); each incorporated herein in its entirety by reference.

For example, plant expression vectors may include (1) a cloned plant nucleic acid under the transcriptional control of 5' and 3' regulatory sequences and (2) a dominant selectable marker. Such plant expression vectors may also contain, if desired, a promoter regulatory region (e.g., one conferring inducible, constitutive, environmentally- or developmentally-regulated, or cell- or tissue-specific/selective expression), a transcription initiation start site, a ribosome binding site, an RNA processing signal, a transcription termination site, and/or a polyadenylation signal.

Constitutive, tissue-preferred or inducible promoters can be employed. Examples of constitutive promoters include the cauliflower mosaic virus (CaMV) 35S transcription initiation region, the 1'- or 2'-promoter derived from T-DNA of *Agrobacterium tumefaciens,* the ubiquitin 1 promoter, the Smas promoter, the cinnamyl alcohol dehydrogenase promoter (U.S. Pat. No. 5,683,439), the Nos promoter, the pEmu promoter, the rubisco promoter, the GRP1-8 promoter and other transcription initiation regions from various plant genes known to those of skill.

Examples of inducible promoters are the Adh1 promoter which is inducible by hypoxia or cold stress, the Hsp70 promoter which is inducible by heat stress, and the PPDK promoter which is inducible by light. Also useful are promoters which are chemically inducible.

Examples of promoters under developmental control include promoters that initiate transcription preferentially in certain tissues, such as leaves, roots, fruit, seeds, or flowers. An exemplary promoter is the anther specific promoter 5126 (U.S. Pat. Nos. 5,689,049 and 5,689,051). Examples of seed-preferred promoters include, but are not limited to, 27 kD gamma zein promoter and waxy promote, Boronat, A., Martinez, M. C., Reina, M., Puigdomenech, P. and Palau, J.; Isolation and sequencing of a 28 kD glutelin-2 gene from maize: Common elements in the 5' flanking regions among zein and glutelin genes; *Plant Sci.* 47, 95–102 (1986) and Reina, M., Ponte, I., Guillen, P., Boronat, A. and Palau, J., Sequence analysis of a genomic clone encoding a Zc2 protein from *Zea mays* W64 A, *Nucleic Acids Res.* 18 (21), 6426 (1990). See the following site relating to the waxy promoter: Kloesgen, R. B., Gierl, A., Schwarz-Sommer, Z S. and Saedler, H., Molecular analysis of the waxy locus of *Zea mays, Mol. Gen. Genet.* 203, 237–244 (1986). Promoters that express in the embryo, pericarp, and endosperm are disclosed in U.S. application Ser. No. 60/097,233 filed Aug. 20, 1998 and Ser. No. 60/098,230 filed Aug. 28, 1998. The disclosures of each of these are incorporated herein by reference in their entirety.

Either heterologous or non-heterologous (i.e., endogenous) promoters can be employed to direct expression of the nucleic acids of the present invention. These promoters can also be used, for example, in expression cassettes to drive expression of antisense nucleic acids to reduce, increase, or alter concentration and/or composition of the proteins of the present invention in a desired tissue.

If polypeptide expression is desired, it is generally desirable to include a polyadenylation region at the 3'-end of a polynucleotide coding region. The polyadenylation region can be derived from the natural gene, from a variety of other plant genes, or from T-DNA. The 3' end sequence to be added can be derived from, for example, the nopaline synthase or octopine synthase genes, or alternatively from another plant gene, or less preferably from any other eukaryotic gene.

An intron sequence can be added to the 5' untranslated region or the coding sequence of the partial coding sequence to increase the amount of the mature message that accumulates. See for example Buchman and Berg, *Mol. Cell Biol.* 8:4395–4405 (1988); Callis et al., *Genes Dev.* 1:1 183–1200 (1987). Use of maize introns Adh1-S intron 1, 2, and 6, the Bronze-1 intron are known in the art. See generally, *The Maize Handbook,* Chapter 116, Freeling and Walbot, Eds., Springer, N.Y. (1994).

The vector comprising the sequences from a polynucleotide of the present invention will typically comprise a marker gene which confers a selectable phenotype on plant cells. Usually, the selectable marker gene will encode antibiotic or herbicide resistance. Suitable genes include those coding for resistance to the antibiotic spectinomycin or streptomycin (e.g., the aada gene), the streptomycin phosphotransferase (SPT) gene coding for streptomycin resistance, the neomycin phosphotransferase (NPTII) gene encoding kanamycin or geneticin resistance, the hygromycin phosphotransferase (HPT) gene coding for hygromycin resistance.

Suitable genes coding for resistance to herbicides include those which act to inhibit the action of acetolactate synthase (ALS), in particular the sulfonylurea-type herbicides (e.g., the acetolactate synthase (ALS) gene containing mutations leading to such resistance in particular the S4 and/or Hra mutations), those which act to inhibit action of glutamine synthase, such as phosphinothricin or basta (e.g., the bar gene), or other such genes known in the art. The bar gene encodes resistance to the herbicide basta and the ALS gene encodes resistance to the herbicide chlorsulfuron.

Typical vectors useful for expression of nucleic acids in higher plants are well known in the art and include vectors derived from the tumor-inducing (Ti) plasmid of *Agrobacterium tumefaciens* described by Rogers et al., *Meth. In Enzymol.* 153:253–277 (1987). Exemplary *A. tumefaciens* vectors useful herein are plasmids pKYLX6 and pKYLX7 of Schardi et al., Gene 61:1–11 (1987) and Berger et al., Proc. Natl. Acad. Sci. USA 86:8402–8406 (1989). Another useful vector herein is plasmid pBl101.2 that is available from Clontech Laboratories, Inc. (Palo Alto, Calif.).

A variety of plant viruses that can be employed as vectors are known in the art and include cauliflower mosaic virus (CaMV), geminivirus, brome mosaic virus, and tobacco mosaic virus.

A polynucleotide of the present invention can be expressed in either sense or anti-sense orientation as desired. In plant cells, it has been shown that antisense RNA inhibits gene expression by preventing the accumulation of mRNA which encodes the enzyme of interest, see, e.g., Sheehy et al., Proc. Nat'l. Acad. Sci. USA 85:8805–8809 (1988); and Hiatt et al., U.S. Pat. No. 4,801,340.

Another method of suppression is sense suppression. Introduction of nucleic acid configured in the sense orientation has been shown to be an effective means by which to block the transcription of target genes. For an example of the use of this method to modulate expression of endogenous genes see, Napoli et al., *The Plant Cell* 2:279–289 (1990) and U.S. Pat. No. 5,034,323.

A method of down-regulation of the protein involves using PEST sequences that provide a target for degradation of the protein.

Catalytic RNA molecules or ribozymes can also be used to inhibit expression of plant genes. The inclusion of ribozyme sequences within antisense RNAs confers RNA-cleaving activity upon them, thereby increasing the activity of the constructs. The design and use of target RNA-specific ribozymes is described in Haseloff et al., *Nature* 334:585–591 (1988).

A variety of cross-linking agents, alkylating agents and radical generating species as pendant groups on polynucleotides of the present invention can be used to bind, label, detect, and/or cleave nucleic acids. For example, Vlassov, V. V., et al., *Nucleic Acids Res* (1986) 14:4065–4076, describe covalent bonding of a single-stranded DNA fragment with alkylating derivatives of nucleotides complementary to target sequences. A report of similar work by the same group is that by Knorre, D. G., et al., *Biochimie* (1985) 67:785–789. Iverson and Dervan also showed sequence-specific cleavage of single-stranded DNA mediated by incorporation of a modified nucleotide which was capable of activating cleavage (*J. Am. Chem. Soc.* (1987) 109:1241–1243). Meyer, R. B., et al., *J. Am. Chem. Soc.* (1989) 111:8517–8519, effect covalent crosslinking to a target nucleotide using an alkylating agent complementary to the single-stranded target nucleotide sequence. A photoactivated crosslinking to single-stranded oligonucleotides mediated by psoralen was disclosed by Lee, B. L., et al., *Biochemistry* (1988) 27:3197–3203. Use of crosslinking in triple-helix forming probes was also disclosed by Home, et al., *J. Am. Chem. Soc.* (1990) 112:2435–2437. Use of N4, N4-ethanocytosine as an alkylating agent to crosslink to single-stranded oligonucleotides has also been described by Webb and Matteucci, *J. Am. Chem. Soc.* (1986) 108:2764–2765; *Nucleic Acids Res.* (1986) 14:7661–7674; Feteritz et al., *J. Am. Chem. Soc.* 113:4000 (1991). Various compounds to bind, detect, label, and/or cleave nucleic acids are known in the art. See, for example, U.S. Pat. Nos. 5,543,507; 5,672,593; 5,484,908; 5,256,648; and, 5,681941.

Proteins

Proteins of the present invention include proteins derived from the native protein by deletion (so-called truncation), addition or substitution of one or more amino acids at one or more sites in the native protein. Such variants may result from, for example, genetic polymorphism or from human manipulation. Methods for such manipulations are generally known in the art.

For example, amino acid sequence variants of the polypeptide can be prepared by mutations in the cloned DNA sequence encoding the native protein of interest. Methods for mutagenesis and nucleotide sequence alterations are well known in the art. See, for example, Walker and Gaastra, eds. (1983) *Techniques in Molecular Biology* (MacMillan Publishing Company, New York); Kunkel (1985) *Proc. Natl. Acad. Sci. USA* 82:488492; Kunkel et al. (1987) *Methods Enzymol.* 154:367–382; Sambrook et al. (1989) *Molecular Cloning: A Laboratory Manual* (Cold Spring Harbor, N.Y.); U.S. Pat. No. 4,873,192; and the references cited therein; herein incorporated by reference. Guidance as to appropriate amino acid substitutions that do not affect biological activity of the protein of interest may be found in the model of Dayhoff et al. (1978) *Atlas of Protein Sequence and Structure* (Natl. Biomed. Res. Found., Washington, D.C.), herein incorporated by reference. Conservative substitutions, such as exchanging one amino acid with another having similar properties, may be preferred.

In constructing variants of the proteins of interest, modifications to the nucleotide sequences encoding the variants will be made such that variants continue to possess the desired activity. Obviously, any mutations made in the DNA encoding the variant protein must not place the sequence out of reading frame and preferably will not create complementary regions that could produce secondary mRNA structure. See EP Patent Application Publication No. 0075444 B1.

The isolated proteins of the present invention include a polypeptide comprising at least 23 contiguous amino acids encoded by any one of the nucleic acids of the present invention, or polypeptides which are conservatively modified variants thereof. The proteins of the present invention or variants thereof can comprise any number of contiguous amino acid residues from a polypeptide of the present invention, wherein that number is selected from the group of integers consisting of from 23 to the number of residues in a full-length polypeptide of the present invention. Optionally, this subsequence of contiguous amino acids is at least 25, 30, 35, or 40 amino acids in length, often at least 50, 60, 70, 80, or 90 amino acids in length.

The present invention includes catalytically active polypeptides (i.e., enzymes). Catalytically active polypeptides will generally have a specific activity of at least 20%, 30%, or 40%, and preferably at least 50%, 60%, or 70%, and most preferably at least 80%, 90%, or 95% that of the native (non-synthetic), endogenous polypeptide. Further, the substrate specificity ($k_{cat}/K_m$) is optionally substantially similar to the native (non-synthetic), endogenous polypeptide. Typically, $k_{cat}/K_m$ will be at least 30%, 40%, or 50%, that of the native (non-synthetic), endogenous polypeptide; and more preferably at least 60%, 70%, 80%, or 90%. Methods of assaying and quantifying measures of enzymatic activity and substrate specificity ($k_{cat}/K_m$), are well known to those of skill in the art.

The present invention includes modifications that can be made to an inventive protein without diminishing its biological activity. Some modifications may be made to facilitate the cloning, expression, or incorporation of the targeting molecule into a fusion protein. Such modifications are well known to those of skill in the art and include, for example, a methionine added at the amino terminus to provide an initiation site, or additional amino acids (e.g., poly His)

placed on either terminus to create conveniently located restriction sites or termination codons or purification sequences.

A protein of the present invention can be expressed in a recombinantly engineered cell such as bacteria, yeast, insect, mammalian, or preferably plant cells. The cells produce the protein in a non-natural condition (e.g., in quantity, composition, location, and/or time), because they have been genetically altered through human intervention to do so.

Typically, an intermediate host cell will be used in the practice of this invention to increase the copy number of the cloning vector. With an increased copy number, the vector containing the nucleic acid of interest can be isolated in significant quantities for introduction into the desired plant cells.

Host cells that can be used in the practice of this invention include prokaryotes, including bacterial hosts such as *Eschericia coli, Salmonella typhimurium,* and *Serratia marcescens.* Eukaryotic hosts such as yeast or filamentous fungi may also be used in this invention. It is preferred to use plant promoters that do not cause expression of the polypeptide in bacteria.

Commonly used prokaryotic control sequences include promoters such as the beta lactamase (penicillinase) and lactose (lac) promoter systems (Chang et al., Nature 198:1056 (1977)), the tryptophan (trp) promoter system (Goeddel et al., Nucleic Acids Res. 8:4057 (1980)) and the lambda derived P L promoter and N-gene ribosome binding site (Shimatake et al., Nature 292:128 (1981)). The inclusion of selection markers in DNA vectors transfected in *E. coli* is also useful. Examples of such markers include genes specifying resistance to ampicillin, tetracycline, or chloramphenicol.

The vector is selected to allow introduction into the appropriate host cell. Bacterial vectors are typically of plasmid or phage origin. Expression systems for expressing a protein of the present invention are available using Bacillus sp. and Salmonella (Palva, et al., *Gene* 22:229–235 (1983); Mosbach, et al., *Nature* 302:543–545 (1983)).

Synthesis of heterologous proteins in yeast is well known. See Sherman, F., et al., *Methods in Yeast Genetics,* Cold Spring Harbor Laboratory (1982). Two widely utilized yeast for production of eukaryotic proteins are *Saccharomyces cerevisiae* and *Pichia pastoris.* Vectors, strains, and protocols for expression in Saccharomyces and Pichia are known in the art and available from commercial suppliers (e.g., Invitrogen). Suitable vectors usually have expression control sequences, such as promoters, including 3-phosphoglycerate kinase or alcohol oxidase, and an origin of replication, termination sequences and the like as desired.

A protein of the present invention, once expressed, can be isolated from yeast by lysing the cells and applying standard protein isolation techniques to the lysates. The monitoring of the purification process can be accomplished by using Western blot techniques or radioimmunoassay or other standard immunoassay techniques.

The proteins of the present invention can also be constructed using non-cellular synthetic methods. Solid phase synthesis of proteins of less than about 50 amino acids in length may be accomplished by attaching the C-terminal amino acid of the sequence to an insoluble support followed by sequential addition of the remaining amino acids in the sequence. Techniques for solid phase synthesis are described by Barany and Merrifield, Solid-Phase Peptide Synthesis, pp. 3–284 in *The Peptides: Analysis, Synthesis, Biology.* Vol. 2: *Special Methods in Peptide Synthesis, Part A.;* Merrifield, et al., *J. Am. Chem. Soc.* 85:2149–2156(1963), and Stewart et al., *Solid Phase Peptide Synthesis,* 2nd ed., Pierce Chem. Co., Rockford, Ill. (1984). Proteins of greater length may be synthesized by condensation of the amino and carboxy termini of shorter fragments. Methods of forming peptide bonds by activation of a carboxy terminal end (e.g., by the use of the coupling reagent N,N'-dicycylohexylcarbodiimide) is known to those of skill.

The proteins of this invention may be purified to substantial purity by standard techniques well known in the art, including detergent solubilization, selective precipitation with such substances as ammonium sulfate, column chromatography, immunopurification methods, and others. See, for instance, R. Scopes, *Protein Purification: Principles and Practice,* Springer-Verlag: New York (1982); Deutscher, *Guide to Protein Purification,* Academic Press (1990). For example, antibodies may be raised to the proteins as described herein. Purification from *E. coli* can be achieved following procedures described in U.S. Pat. No. 4,511,503. Detection of the expressed protein is achieved by methods known in the art and include, for example, radioimmunoassays, Western blotting techniques or immunoprecipitation.

The present invention further provides a method for modulating (i.e., increasing or decreasing) the concentration or composition of the polypeptides of the present invention in a plant or part thereof. Modulation of the polypeptides can be effected by increasing or decreasing the concentration and/or the composition of the polypeptides in a plant. The method comprises transforming a plant cell with an expression cassette comprising a polynucleotide of the present invention to obtain a transformed plant cell, growing the transformed plant cell under plant forming conditions, and expressing the polynucleotide in the plant for a time sufficient to modulate concentration and/or composition of the polypeptides in the plant or plant part.

In some embodiments, the content and/or composition of polypeptides of the present invention in a plant may be modulated by altering, in vivo or in vitro, the promoter of a non-isolated gene of the present invention to up- or down-regulate gene expression. In some embodiments, the coding regions of native genes of the present invention can be altered via substitution, addition, insertion, or deletion to decrease activity of the encoded enzyme. See, e.g., Kmiec, U.S. Pat. No. 5,565,350; Zarling et al., PCT/US93/03868.

In some embodiments, an isolated nucleic acid (e.g., a vector) comprising a promoter sequence is transfected into a plant cell. Subsequently, a plant cell comprising the isolated nucleic acid is selected for by means known to those of skill in the art such as, but not limited to, Southern blot, DNA sequencing, or PCR analysis using primers specific to the promoter and to the nucleic acid and detecting amplicons produced therefrom. A plant or plant part altered or modified by the foregoing embodiments is grown under plant forming conditions for a time sufficient to modulate the concentration and/or composition of polypeptides of the present invention in the plant. Plant forming conditions are well known in the art.

In general, concentration of the polypeptides is increased or decreased by at least 5%, 10%, 20%, 30%, 40%, 50%, 60%, 70%, 80%, or 90% relative to a native control plant, plant part, or cell lacking the aforementioned expression cassette. Modulation in the present invention may occur during and/or subsequent to growth of the plant to the desired stage of development.

Modulating nucleic acid expression temporally and/or in particular tissues can be controlled by employing the appropriate promoter operably linked to a polynucleotide of the present invention in, for example, sense or antisense orientation as discussed in greater detail above. Induction of expression of a polynucleotide of the present invention can also be controlled by exogenous administration of an effective amount of inducing compound. Inducible promoters and inducing compounds that activate expression from these promoters are well known in the art.

In preferred embodiments, the polypeptides of the present invention are modulated in monocots or dicots, preferably maize, soybean, alfalfa, sunflower, Brassica, cotton, sorghum, wheat, barley, millet, rice, cassava, potato, Arabidopsis, tomato, pepper, apple, spinach, or lettuce.

Means of detecting the proteins of the present invention are not critical aspects of the present invention. In a preferred embodiment, the proteins are detected and/or quantified using any of a number of well recognized immunological binding assays (see, e.g., U.S. Pat. Nos. 4,366,241; 4,376,110; 4,517,288; and 4,837,168). For a review of the general immunoassays, see also Methods in Cell Biology, Vol. 37: *Antibodies in Cell Biology*, Asai, Ed., Academic Press, Inc. New York (1993); *Basic and Clinical Immunology* 7th Edition, Stites & Terr, Eds. (1991). Moreover, the immunoassays of the present invention can be performed in any of several configurations, e.g., those reviewed in *Enzyme Immunoassay*, Maggio, Ed., CRC Press, Boca Raton, Fla. (1980); Tijan, Practice and Theory of Enzyme Immunoassays, *Laboratory Techniques in Biochemistry and Molecular Biology*, Elsevier Science Publishers B. V., Amsterdam (1985); Harlow and Lane, supra; *Immunoassay: A Practical Guide*, Chan, Ed., Academic Press, Orlando, Fla. (1987); *Principles and Practice of Immunoassays*, Price and Newman Eds., Stockton Press, NY (1991); and *Non-isotopic Immunoassays*, Ngo, Ed., Plenum Press, NY (1988).

Typical methods for detecting proteins include Western blot (immunoblot) analysis, analytic biochemical methods such as electrophoresis, capillary electrophoresis, high performance liquid chromatography (HPLC), thin layer chromatography (TLC), hyperdiffusion chromatography, and the like, and various immunological methods such as fluid or gel precipitin reactions, immunodiffusion (single or double), immunoelectrophoresis, radioimmunoassays (RIAs), enzyme-linked immunosorbent assays (ELISAs), immunofluorescent assays, and the like.

Non-radioactive labels are often attached by indirect means. Generally, a ligand molecule (e.g., biotin) is covalently bound to the molecule. The ligand then binds to an anti-ligand (e.g., streptavidin) molecule that is either inherently detectable or covalently bound to a signal system, such as a detectable enzyme, a fluorescent compound, or a chemiluminescent compound. A number of ligands and anti-ligands can be used. Where a ligand has a natural anti-ligand, for example, biotin, thyroxine, and cortisol, it can be used in conjunction with the labeled, naturally occurring anti-ligands. Alternatively, any haptenic or antigenic compound can be used in combination with an antibody.

The molecules can also be conjugated directly to signal generating compounds, e.g., by conjugation with an enzyme or fluorophore. Enzymes of interest as labels will primarily be hydrolases, particularly phosphatases, esterases and glycosidases, or oxidoreductases, particularly peroxidases. Fluorescent compounds include fluorescein and its derivatives, rhodamine and its derivatives, dansyl, umbelliferone, etc. Chemiluminescent compounds include luciferin, and 2,3-dihydrophthalazinediones, e.g., luminol. For a review of various labeling or signal producing systems which may be used, see U.S. Pat. No. 4,391,904, which is incorporated herein by reference.

Some assay formats do not require the use of labeled components. For instance, agglutination assays can be used to detect the presence of the target antibodies. In this case, antigen-coated particles are agglutinated by samples comprising the target antibodies. In this format, none of the components need be labeled and the presence of the target antibody is detected by simple visual inspection.

The proteins of the present invention can be used for identifying compounds that bind to (e.g., substrates), and/or increase or decrease (i.e., modulate) the enzymatic activity of catalytically-active polypeptides of the present invention. The method comprises contacting a polypeptide of the present invention with a compound whose ability to bind to or modulate enzyme activity is to be determined. The polypeptide employed will have at least 20%, preferably at least 30% or 40%, more preferably at least 50% or 60%, and most preferably at least 70% or 80% of the specific activity of the native, full-length polypeptide of the present invention (e.g., enzyme). Methods of measuring enzyme kinetics are well known in the art. See, e.g., Segel, *Biochemical Calculations*, $2^{nd}$ ed., John Wiley and Sons, New York (1976).

Antibodies can be raised to a protein of the present invention, including individual, allelic, strain, or species variants, and fragments thereof, both in their naturally occurring (full-length) forms and in recombinant forms. Additionally, antibodies are raised to these proteins in either their native configurations or in non-native configurations. Anti-idiotypic antibodies can also be generated. Many methods of making antibodies are known to persons of skill.

In some instances, it is desirable to prepare monoclonal antibodies from various mammalian hosts, such as mice, rodents, primates, humans, etc. Description of techniques for preparing such monoclonal antibodies are found in, e.g., *Basic and Clinical Immunology*, 4th ed., Stites et al., Eds., Lange Medical Publications, Los Altos, Calif., and references cited therein; Harlow and Lane, Supra; Goding, *Monoclonal Antibodies: Principles and Practice*, 2nd ed., Academic Press, New York, N.Y. (1986); and Kohler and Milstein, *Nature* 256: 495–497 (1975).

Other suitable techniques involve selection of libraries of recombinant antibodies in phage or similar vectors (see, e.g., Huse et al., *Science* 246:1275–1281 (1989); and Ward, et al., *Nature* 341:544–546 (1989); and Vaughan et al., *Nature Biotechnology*, 14:309–314 (1996)). Alternatively, high avidity human monoclonal antibodies can be obtained from transgenic mice comprising fragments of the unrearranged human heavy and light chain lg loci (i.e., minilocus transgenic mice). Fishwild et al., *Nature Biotech.*, 14:845–851 (1996). Also, recombinant immunoglobulins may be produced. See, Cabilly, U.S. Pat. No. 4,816,567; and Queen et al., *Proc. Nat'l Acad. Sci.* 86:10029–10033 (1989).

The antibodies of this invention can be used for affinity chromatography in isolating proteins of the present invention, for screening expression libraries for particular expression products such as normal or abnormal protein or for raising anti-idiotypic antibodies which are useful for detecting or diagnosing various pathological conditions related to the presence of the respective antigens.

Frequently, the proteins and antibodies of the present invention will be labeled by joining, either covalently or non-covalently, a substance which provides for a detectable signal. A wide variety of labels and conjugation techniques are known and are reported extensively in both the scientific and patent literature. Suitable labels include radionucleotides, enzymes, substrates, cofactors, inhibitors, fluorescent moieties, chemiluminescent moieties, magnetic particles, and the like.

Transformation of Cells

The method of transformation/transfection is not critical to the invention; various methods of transformation or transfection are currently available. As newer methods are available to transform crops or other host cells they may be directly applied. Accordingly, a wide variety of methods have been developed to insert a DNA sequence into the genome of a host cell to obtain the transcription and/or translation of the sequence to effect phenotypic changes in the organism. Thus, any method that provides for efficient transformation/transfection may be employed.

A DNA sequence coding for the desired polynucleotide of the present invention, for example a cDNA, RNA or a genomic sequence, will be used to construct an expression cassette that can be introduced into the desired plant. Isolated nucleic acid acids of the present invention can be introduced into plants according to techniques known in the art. Generally, expression cassettes as described above and suitable for transformation of plant cells are prepared.

Techniques for transforming a wide variety of higher plant species are well known and described in the technical, scientific, and patent literature. See, for example, Weising et al., *Ann. Rev. Genet* 22:421–477 (1988). For example, the DNA construct may be introduced directly into the genomic DNA of the plant cell using techniques such as electroporation, PEG-mediated transfection, particle bombardment, silicon fiber delivery, or microinjection of plant cell protoplasts or embryogenic callus. See, e.g., Tomes, et al., Direct DNA Transfer into Intact Plant Cells Via Microprojectile Bombardment. pp.197–213 in Plant Cell, Tissue and Organ Culture, Fundamental Methods. eds. O. L. Gamborg and G. C. Phillips. Springer-Verlag Berlin Heidelberg New York, 1995. Alternatively, the DNA constructs may be combined with suitable T-DNA flanking regions and introduced into a conventional *Agrobacterium tumefaciens* host vector. The virulence functions of the *Agrobacterium tumefaciens* host will direct the insertion of the construct and adjacent marker into the plant cell DNA when the cell is infected by the bacteria. See, U.S. Pat. No. 5,591,616.

The introduction of DNA constructs using polyethylene glycol precipitation is described in Paszkowski et al., *Embo J.* 3:2717–2722 (1984). Electroporation techniques are described in Fromm et al., *Proc. Natl. Acad. Sci.* 82:5824 (1985). Ballistic transformation techniques are described in Klein et al., *Nature* 327:70–73 (1987).

*Agrobacterium tumefaciens*-meditated transformation techniques are well described in the scientific literature. See, for example Horsch et al., *Science* 233:496498 (1984), and Fraley et al., *Proc. Natl. Acad. Sci.* 80:4803 (1983). For instance, Agrobacterium transformation of maize is described in WO publication no. 98/32326.

Other methods of transfection or transformation include (1) *Agrobacterium rhizogenes*-mediated transformation (see, e.g., Lichtenstein and Fuller In: Genetic Engineering, vol. 6, PWJ Rigby, Ed., London, Academic Press, 1987; and Lichtenstein, C. P., and Draper, J,. In: DNA Cloning, Vol. II, D. M. Glover, Ed., Oxford, IRI Press, 1985); Application PCT/US87/02512 (WO 88/02405 published Apr. 7, 1988) describes the use of *A. rhizogenes* strain A4 and its Ri plasmid along with *A. tumefaciens* vectors pARC8 or pARC16; (2) liposome-mediated DNA uptake (see, e.g., Freeman et al., *Plant Cell Physiol.* 25:1353, 1984); (3) the vortexing method (see, e.g., Kindle, *Proc. Natl. Acad. Sci.* USA 87:1228, (1990).

DNA can also be introduced into plants by direct DNA transfer into pollen as described by Zhou et al., Methods in Enzymology, 101:433 (1983); D. Hess, Intern Rev. Cytol., 107:367 (1987); Luo et al., Plant Mol. Biol. Reporter, 6:165 (1988). Expression of polypeptide coding nucleic acids can be obtained by injection of the DNA into reproductive organs of a plant as described by Pena et al., Nature 325:274 (1987). DNA can also be injected directly into the cells of immature embryos and the rehydration of desiccated embryos as described by Neuhaus et al., Theor. Appl. Genet., 75:30 (1987); and Benbrook et al., in Proceedings Bio Expo 1986, Butterworth, Stoneham, Mass., pp. 27–54 (1986).

Animal and lower eukaryotic (e.g., yeast) host cells are competent or rendered competent for transfection by various means. There are several well-known methods of introducing DNA into animal cells. These include: calcium phosphate precipitation, fusion of the recipient cells with bacterial protoplasts containing the DNA, treatment of the recipient cells with liposomes containing the DNA, DEAE dextran, electroporation, biolistics, and micro-injection of the DNA directly into the cells. The transfected cells are cultured by means well known in the art. Kuchler, R. J., *Biochemical Methods in Cell Culture and Virology*, Dowden, Hutchinson and Ross, Inc. (1977).

Transgenic Plant Regeneration

Transformed plant cells which are derived by any of the above transformation techniques can be cultured to regenerate a whole plant which possesses the transformed genotype. Such regeneration techniques often rely on manipulation of certain phytohormones in a tissue culture growth medium, typically relying on a biocide and/or herbicide marker which has been introduced together with a polynucleotide of the present invention. For transformation and regeneration of maize see, Gordon-Kamm et al., *The Plant Cell*, 2:603–618 (1990).

Plants cells transformed with a plant expression vector can be regenerated, e.g., from single cells, callus tissue or leaf discs according to standard plant tissue culture techniques. It is well known in the art that various cells, tissues, and organs from almost any plant can be successfully cultured to regenerate an entire plant. Plant regeneration from cultured protoplasts is described in Evans et al., *Protoplasts Isolation and Culture, Handbook of Plant Cell Culture*, Macmillan Publishing Company, New York, pp. 124–176 (1983); and Binding, *Regeneration of Plants, Plant Protoplasts*, CRC Press, Boca Raton, pp. 21–73 (1985).

The regeneration of plants containing the foreign gene introduced by Agrobacterium can be achieved as described by Horsch et al., *Science,* 227:1229–1231 (1985) and Fraley et al., *Proc. Natl. Acad. Sci. USA* 80:4803 (1983). This procedure typically produces shoots within two to four weeks and these transformant shoots are then transferred to an appropriate root-inducing medium containing the selective agent and an antibiotic to prevent bacterial growth. Transgenic plants of the present invention may be fertile or sterile.

Regeneration can also be obtained from plant callus, explants, organs, or parts thereof. Such regeneration techniques are described generally in Klee et al., *Ann. Rev. of Plant Phys.* 38:467–486 (1987). The regeneration of plants from either single plant protoplasts or various explants is well known in the art. See, for example, *Methods for Plant Molecular Biology*, A. Weissbach and H. Weissbach, eds., Academic Press, Inc., San Diego, Calif. (1988). For maize cell culture and regeneration see generally, *The Maize Handbook*, Freeling and Walbot, Eds., Springer, N.Y. (1994); *Corn and Corn Improvement*, 3$^{rd}$ edition, Sprague and Dudley Eds., American Society of Agronomy, Madison, Wis. (1988).

One of skill will recognize that after the expression cassette is stably incorporated in transgenic plants and confirmed to be operable, it can be introduced into other plants by sexual crossing. Any of a number of standard breeding techniques can be used, depending upon the species to be crossed.

In vegetatively propagated crops, mature transgenic plants can be propagated by the taking of cuttings or by tissue culture techniques to produce multiple identical plants. Selection of desirable transgenics is made and new varieties are obtained and propagated vegetatively for commercial use. In seed-propagated crops, mature transgenic plants can be self crossed to produce a homozygous inbred plant. The inbred plant produces seed containing the newly introduced heterologous nucleic acid. These seeds can be grown to produce plants that would produce the selected phenotype.

Parts obtained from the regenerated plant, such as flowers, seeds, leaves, branches, fruit, and the like are included in the invention, provided that these parts comprise cells comprising the isolated nucleic acid of the present invention. Progeny and variants, and mutants of the regenerated plants are also included within the scope of the invention, provided that these parts comprise the introduced nucleic acid sequences.

Transgenic plants expressing a selectable marker can be screened for transmission of the nucleic acid of the present invention by, for example, standard immunoblot and DNA detection techniques. Transgenic lines are also typically evaluated on levels of expression of the heterologous nucleic acid. Expression at the RNA level can be determined initially to identify and quantitate expression-positive plants. Standard techniques for RNA analysis can be employed and include PCR amplification assays using oligonucleotide primers designed to amplify only the heterologous RNA templates and solution hybridization assays using heterologous nucleic acid-specific probes. The RNA-positive plants can then be analyzed for protein expression by Western immunoblot analysis using the specifically reactive antibodies of the present invention. In addition, in situ hybridization and immunocytochemistry according to standard protocols can be done using heterologous nucleic acid specific polynucleotide probes and antibodies, respectively, to localize sites of expression within transgenic tissue. Generally, a number of transgenic lines are usually screened for the incorporated nucleic acid to identify and select plants with the most appropriate expression profiles.

A preferred embodiment is a transgenic plant that is homozygous for the added heterologous nucleic acid; i.e., a transgenic plant that contains two added nucleic acid sequences, one gene at the same locus on each chromosome of a chromosome pair. A homozygous transgenic plant can be obtained by sexually mating (selfing) a heterozygous transgenic plant that contains a single added heterologous nucleic acid, germinating some of the seed produced and analyzing the resulting plants produced for altered expression of a polynucleotide of the present invention relative to a control plant (i.e., native, non-transgenic). Back-crossing to a parental plant and out-crossing with a non-transgenic plant are also contemplated.

The present invention provides a method of genotyping a plant comprising a polynucleotide of the present invention. Genotyping provides a means of distinguishing homologs of a chromosome pair and can be used to differentiate segregants in a plant population. Molecular marker methods can be used for phylogenetic studies, characterizing genetic relationships among crop varieties, identifying crosses or somatic hybrids, localizing chromosomal segments affecting monogenic traits, map based cloning, and the study of quantitative inheritance. See, e.g., *Plant Molecular Biology: A Laboratory Manual,* Chapter 7, Clark, Ed., Springer-Verlag, Berlin (1997). For molecular marker methods, see generally, The DNA Revolution by Andrew H. Paterson 1996 (Chapter 2) in: *Genome Mapping in Plants* (ed. Andrew H. Paterson) by Academic Press/R. G. Landis Company, Austin, Tex., pp. 7–21.

The particular method of genotyping in the present invention may employ any number of molecular marker analytic techniques such as, but not limited to, restriction fragment length polymorphisms (RFLPs). RFLPs are the product of allelic differences between DNA restriction fragments caused by nucleotide sequence variability. Thus, the present invention further provides a means to follow segregation of a gene or nucleic acid of the present invention as well as chromosomal sequences genetically linked to these genes or nucleic acids using such techniques as RFLP analysis.

Plants that can be transformed in the method of the invention include monocotyledonous and dicotyledonous plants. Preferred plants include maize, soybean, alfalfa, sunflower, Brassica, cotton, sorghum, wheat, barley, millet, rice, cassava, potato, Arabidopsis, tomato, pepper, apple, spinach, and lettuce.

Seeds derived from plants regenerated from transformed plant cells, plant parts or plant tissues, or progeny derived from the regenerated transformed plants, may be used directly as feed or food, or further processing may occur.

The present invention will be further described by reference to the following detailed examples. It is understood, however, that there are many extensions, variations, and modifications on the basic theme of the present invention beyond that shown in the examples and description, which are within the spirit and scope of the present invention. All publications, patents, and patent applications cited herein are hereby incorporated by reference.

EXAMPLES

Construction of cDNA Libraries

Total RNA is isolated from preferred plant tissues, such as roots, rhizomes, or tubers, with Promega's RNAgents (Promega, Madison, Wis.). In brief, tissue samples are pulverized in liquid nitrogen before the addition of a denaturing solution. Addition of a mixture of phenol and chloroform is followed by centrifugation to separate an aqueous phase and an organic phase. The total RNA is recovered by precipitation with isopropyl alcohol from the aqueous phase. Purification of mRNA is performed using the Pharmacia oligo(dT)-cellulose spun column system (Amersham Pharmacia Biotech, Uppsala, Sweden).

cDNA synthesis is performed and unidirectional cDNA libraries are constructed using products of Life Technologies Inc. (Rockville, Md.) and Stratagene (La Jolla, Calif.). The first strand of cDNA is synthesized with SuperScript™ II Reverse Transcriptase at 37° C. Second strand synthesis is carried out at 16° C. The cDNA fragments are purified using a sephacryl cDNA size fractionation column and ligated into an appropriate vector between EcoRI and XhoI restriction sites.

Sequencing of cDNA and Library Subtraction

Sequencing Template Preparation

Individual colonies are picked and DNA prepared either by PCR with M13 forward primers and M13 reverse primers, or by plasmid isolation. All the cDNA clones are sequenced using M13 reverse primers.

Q-bot Subtraction Procedure cDNA libraries subjected to the subtraction procedure are plated out on 22×22 cm2 agar plate at density of about 3,000 colonies per plate. The plates are incubated in a 37° C. incubator for 12–24 hours. Colonies are picked into 384-well plates by a robot colony picker, Q-bot (GENETIX Limited). These plates are incubated overnight at 37° C.

Once sufficient colonies are picked, they are pinned onto 22×22 cm2 nylon membranes using Q-bot. Each membrane contains 9,216 colonies or 36,864 colonies. These membranes are placed onto agar plate with appropriate antibiotic. The plates are incubated at 37° C. overnight.

After colonies are recovered on the second day, these filters are placed on filter paper prewetted with denaturing solution for four minutes, then are incubated on top of a boiling water bath for additional four minutes. The filters are then placed on filter paper prewetted with neutralizing solution for four minutes. After excess solution is removed by placing the filters on dry filter papers for one minute, the colony side of the filters are placed into Proteinase K solution, incubated at 37° C. for 40–50 minutes. The filters are placed on dry filter papers to dry overnight. DNA is then cross-linked to nylon membrane by UV light treatment.

Colony hybridization is conducted as described by Sambrook, J., Fritsch, E. F. and Maniatis, T., (in Molecular Cloning: A laboratory Manual, 2nd Edition). The following probes are used in colony hybridization:
1. First strand cDNA from the same tissue as the library was made from to remove the most redundant clones.
2. 48–192 most redundant cDNA clones from the same library based on previous sequencing data.
3. 192 most redundant cDNA clones in the entire sequence database.
4. A Sal-A20 oligo nucleotide: TCG ACC CAC GCG TCC GAA AAA AAA AAA AAA AAA AAA, removes clones containing a poly A tail but no cDNA.
5. cDNA clones derived from rRNA.

The image of the autoradiography is scanned into computer and the signal intensity and cold colony addresses of each colony is analyzed. Re-arraying of cold-colonies from 384 well plates to 96 well plates is conducted using Q-bot.
Identification of the Gene from a Computer Homology Search Gene identities were determined by conducting BLAST (Basic Local Alignment Search Tool; Altschul, S. F., et al., (1993) *J. Mol. Biol.* 215:403–410; see also www.ncbi.nlm.nih.gov/BLAST/) searches under default parameters for similarity to sequences contained in the BLAST "nr" database (comprising all non-redundant GenBank CDS translations, sequences derived from the 3-dimensional structure Brookhaven Protein Data Bank, the last major release of the SWISS-PROT protein sequence database, EMBL, and DDBJ databases). The cDNA sequences were analyzed for similarity to all publicly available DNA sequences contained in the "nr" database using the BLASTN algorithm. The DNA sequences were translated in all reading frames and compared for similarity to all publicly available protein sequences contained in the "nr" database using the BLASTX algorithm (Gish, W. and States, D. J. Nature Genetics 3:266–272 (1993)) provided by the NCBI. In some cases, the sequencing data from two or more clones containing overlapping segments of DNA were used to construct contiguous DNA sequences.
Preparation of Transgenic Plants
Bombardment A general method of genetic transformation used to produce transgenic maize plants is by bombardment of embryogenically responsive immature embryos with tungsten particles associated with DNA plasmids, said plasmids consisting of a selectable and an unselectable marker gene.

Preparation of Tissue

Immature embryos of "High Type II" are the target for particle bombardment-mediated transformation. This genotype is the $F_1$ of two purebred genetic lines, parent A and parent B, derived from A188×B73. Both parents are selected for high competence of somatic embryogenesis. See Armstrong, et al., "Development and Availability of Germplasm with High Type II Culture Formation Response," *Maize Genetics Cooperation Newsletter,* Vol. 65, pp. 92 (1991); incorporated herein in its entirety by reference.

Ears from $F_1$ plants are selfed or sibbed, and embryos are aseptically dissected from developing caryopses when the scutellum first becomes opaque. The proper stage occurs about 9–13 days post-pollination, and most generally about 10 days post-pollination, and depends on growth conditions. The embryos are about 0.75 to 1.5 mm long. Ears are surface sterilized with 20–50% Clorox for 30 min, followed by 3 rinses with sterile distilled water.

Immature embryos are cultured, scutellum oriented upward, on embryogenic induction medium comprised of N6 basal salts (Chu, et al., "Establishment of an Efficient Medium for Anther Culture of Rice Through Comparative Experiments on the Nitrogen Sources," *Scientia Sinica,* (Peking), Vol. 18, pp. 659–668 (1975); incorporated herein in its entirety by reference; Eriksson vitamins (See Eriksson, T., "Studies on the Growth Requirements and Growth Measurements of *Haplopappus gracilis,*" *Physiol. Plant,* Vol. 18, pp. 976–993 (1965); incorporated herein in its entirety by reference), 0.5 mg/l thiamine HCl, 30 gm/l sucrose, 2.88 gm/l L-proline, 1 mg/l 2,4-dichlorophenoxyacetic acid, 2 gm/l Gelrite, and 8.5 mg/l $AgNO_3$.

The medium is sterilized by autoclaving at 121° C. for 15 min and dispensed into 100×25 mm petri dishes. $AgNO_3$ is filter-sterilized and added to the medium after autoclaving. The tissues are cultured in complete darkness at 28° C. After about 3 to 7 days, generally about 4 days, the scutellum of the embryo has swelled to about double its original size and the protuberances at the coleorhizal surface of the scutellum indicate the inception of embryogenic tissue. Up to 100% of the embryos display this response, but most commonly, the embryogenic response frequency is about 80%.

When the embryogenic response is observed, the embryos are transferred to a medium comprised of induction medium modified to contain 120 gm/l sucrose. The embryos are oriented with the coleorhizal pole, the embryogenically responsive tissue, upwards from the culture medium. Ten embryos per petri dish are located in the center of a petri dish in an area about 2 cm in diameter. The embryos are maintained on this medium for 3–16 hr, preferably 4 hours, in complete darkness at 28° C. just prior to bombardment with particles associated with plasmid DNAs containing the selectable and unselectable marker genes.

To effect particle bombardment of embryos, the particle-DNA agglomerates are accelerated using a DuPont PDS-1000 particle acceleration device. The particle-DNA agglomeration is briefly sonicated and 10 μl are deposited on macrocarriers and the ethanol allowed to evaporate. The macrocarrier is accelerated onto a stainless-steel stopping screen by the rupture of a polymer diaphragm (rupture disk). Rupture is effected by pressurized helium. Depending on the rupture disk breaking pressure, the velocity of particle-DNA acceleration may be varied. Rupture disk pressures of 200 to 1800 psi are commonly used, with those of 650 to 1100 psi being more preferred, and about 900 psi being most highly preferred. Rupture disk breaking pressures are additive so multiple disks may be used to effect a range of rupture pressures.

Preferably, the shelf containing the plate with embryos is 5.1 cm below the bottom of the macrocarrier platform (shelf #3), but may be located at other distances. To effect particle bombardment of cultured immature embryos, a rupture disk and a macrocarrier with dried particle-DNA agglomerates are installed in the device. The He pressure delivered to the device is adjusted to 200 psi above the rupture disk breaking pressure. A petri dish with the target embryos is placed into the vacuum chamber and located in the projected path of accelerated particles. A vacuum is created in the chamber, preferably about 28 inches Hg. After operation of the device, the vacuum is released and the petri dish is removed.

Bombarded embryos remain on the osmotically adjusted medium during bombardment, and preferably for two days subsequently, although the embryos may remain on this medium for 1 to 4 days. The embryos are transferred to selection medium comprised of N6 basal salts, Eriksson vitamins, 0.5 mg/l thiamine HCl, 30 gm/l sucrose, 1 mg/l 2,4-dichlorophenoxyacetic acid, 2 gm/l Gelrite, 0.85 mg/l $AgNO_3$ and 3 mg/l bialaphos. Bialaphos is added filter-sterilized. The embryos are subcultured to fresh selection medium at 10 to 14 day intervals. After about 7 weeks, embryogenic tissue, putatively transgenic for both selectable and unselectable marker genes, is seen to proliferate from about 7% of the bombarded embryos. Putative transgenic tissue is rescued, and that tissue derived from individual embryos is considered to be an event and is propagated independently on selection medium. Two cycles of clonal propagation are achieved by visual selection for the smallest contiguous fragments of organized embryogenic tissue.

For regeneration of transgenic plants, embryogenic tissue is subcultured to medium comprised of MS salts and vitamins (Murashige, T. and F. Skoog, "A revised medium for rapid growth and bio assays with tobacco tissue cultures," Physiologia Plantarum 15:473–497 (1962), incorporated herein in its entirety by reference), 100 mg/l myo-inositol, 60 gm/l sucrose, 3 gm/l Gelrite, 0.5 mg/l zeatin, 1 mg/l indole-3-acetic acid, 26.4 ng/l cis-trans-abscissic acid, and 3 mg/l bialaphos in 100×25 mm petri dishes and incubated in darkness at 28° C. until the development of well-formed, matured somatic embryos can be visualized. This requires about 14 days.

Well-formed somatic embryos are opaque and cream-colored, and are comprised of an identifiable scutellum and coleoptile. The embryos are individually subcultured to germination medium comprised of MS salts and vitamins, 100 mg/l myo-inositol, 40 gm/l sucrose and 1.5 gm/l Gelrite in 100×25 mm petri dishes and incubated under a 16 hr light: 8 hr dark photoperiod and 40 $\mu$Einsteinsm$^{-2}$sec$^{-1}$ from cool-white fluorescent tubes. After about 7 days, the somatic embryos have germinated and produced a well-defined shoot and root. The individual plants are subcultured to germination medium in 125×25 mm glass tubes to allow further plant development. The plants are maintained under a 16 hr light: 8 hr dark photoperiod and 40 $\mu$Einsteinsm$^{-2}$sec$^{-1}$ from cool-white fluorescent tubes.

After about 7 days, the plants are well-established and are transplanted to horticultural soil, hardened off, and potted into commercial greenhouse soil mixture and grown to sexual maturity in a greenhouse. An elite inbred line is used as a male to pollinate regenerated transgenic plants.

Preparation of Particles

Fifteen mg of tungsten particles (General Electric), 0.5 to 1.8 $\mu$m, preferably 1 to 1.8 $\mu$m, and most preferably 1 $\mu$m, are added to 2 ml of concentrated nitric acid. This suspension is sonicated at 0° C. for 20 min (Branson Sonifier Model 450, 40% output, constant duty cycle). Tungsten particles are pelleted by centrifugation at 10,000 rpm (Biofuge) for 1 min and the supernatant is removed. Two ml of sterile distilled water are added to the pellet and sonicated briefly to resuspend the particles. The suspension is pelleted, 1 ml of absolute ethanol is added to the pellet and sonicated briefly to resuspend the particles. The particles are rinsed, pelleted, and resuspended a further 2 times with sterile distilled water, and finally the particles are resuspended in 2 ml of sterile distilled water. The particles are subdivided into 250 $\mu$l aliquots and stored frozen.

Preparation of particle-plasmid DNA association

The stock of tungsten particles is sonicated briefly in a water bath sonicator (Branson Sonifier Model 450, 20% output, constant duty cycle) and 50 $\mu$l is transferred to a microfuge tube. Plasmid DNA is added to the particles for a final DNA amount of 0.1 to 10 $\mu$g in 10 $\mu$l total volume, and briefly sonicated. Preferably 1 $\mu$g total DNA is used. Specifically, 5 $\mu$l of PHP8001 (gz::HT12::gz) and 5 $\mu$l of PHP3528 (enhanced CAMV::Bar::PinII), at 0.1 $\mu$g/$\mu$l in TE buffer, are added to the particle suspension. Fifty $\mu$l of sterile aqueous 2.5 M $CaCl_2$ are added, and the mixture is briefly sonicated and vortexed. Twenty $\mu$l of sterile aqueous 0.1M spermidine are added and the mixture is briefly sonicated and vortexed. The mixture is incubated at room temperature for 20 min with intermittent brief sonication. The particle suspension is centrifuged, and the supernatant is removed. Two hundred fifty $\mu$l of absolute ethanol is added to the pellet and briefly sonicated. The suspension is pelleted, the supernatant is removed, and 60 $\mu$l of absolute ethanol is added. The suspension is sonicated briefly before loading the particle-DNA agglomeration onto macrocarriers.

Agrobacterium co-cultivation

Another method of transformation is by co-cultivation with Agrobacterium. Agrobacterium is streaked out from a −80° frozen aliquot onto a plate containing PHI-L medium and cultured at 28° C. in the dark for 3 days. PHI-L media comprises 25 ml/l Stock Solution A, 25 ml/l Stock Solution B, 450.9 ml/l Stock Solution C and spectinomycin (Sigma Chemicals) added to a concentration of 50 mg/l in sterile dd$H_2$O (stock solution A: $K_2HPO_4$ 60.0 g/l, $NaH_2PO_4$ 20.0 g/l, adjust pH to 7.0 w/KOH and autoclave; stock solution B: $NH_4Cl$ 20.0 g/l, $MgSO_4.7H_2O$ 6.0 g/l, KCl 3.0 g/l, $CaCl_2$ 0.20 g/l, $FeSO_4.7H_2O$ 50.0 mg/l, autoclave; stock solution C: glucose 5.56 g/l, agar 16.67 g/l (#A-7049, Sigma Chemicals, St. Louis, Mo.) and autoclave).

The plate can be stored at 4° C. and used usually for about 1 month. A single colony is picked from the master plate and streaked onto a plate containing PHI-M medium [yeast extract (Difco) 5.0 g/l; peptone (Difco)10.0 g/l; NaCl 5.0 g/l; agar (Difco) 15.0 g/l; pH 6.8, containing 50 mg/L spectinomycin] and incubated at 28° C. in the dark for 2 days. Five ml of either PHI-A, [CHU(N6) basal salts (Sigma C-1416) 4.0 g/l, Eriksson's vitamin mix (1000×, Sigma-1511) 1.0 ml/l; thiamine.HCl 0.5 mg/l (Sigma); 2,4-dichlorophenoxyacetic acid (2,4-D, Sigma) 1.5 mg/l; L-proline (Sigma) 0.69 g/l; sucrose (Mallinckrodt) 68.5 g/l; glucose (Mallinckrodt) 36.0 g/l; pH 5.2] for the PHI basic medium system, or PHI-I [MS salts (GIBCO BRL) 4.3 g/l; nicotinic acid (Sigma) 0.5 mg/l; pyridoxine.HCl (Sigma) 0.5 mg/l; thiamine.HCl 1.0 mg/l; myo-inositol (Sigma) 0.10 g/l; vitamin assay casamino acids (Difco Lab) 1.0 g/l; 2, 4-D 1.5 mg/l; sucrose 68.50 g/l; glucose 36.0 g/l; adjust pH to 5.2 w/KOH and filter-sterilize] for the PHI combined medium system and 5 $\mu$l of 100 mM (3'-5'-Dimethoxy-4'-hydroxyacetophenone, Aldrich chemicals) are added to a 14 ml Falcon tube in a hood. About 3 full loops (5 mm loop size) Agrobacterium is collected from the plate and suspended in the tube, then the tube is vortexed to make an even suspension. One ml of the suspension is transferred to a spectrophotometer tube and the OD of the suspension adjusted to 0.72 at 550 nm by adding either more Agrobacterium or more of the same suspension medium, for an Agrobacterium concentration of approximately $0.5\times10^9$ cfu/ml to $1\times10^9$ cfu/ml. The final Agrobacterium suspension is aliquoted into 2 ml microcentrifuge tubes, each containing 1 ml of the suspension. The suspensions are then used as soon as possible.

Embryo isolation, infection and co-cultivation:

About 2 ml of the same medium (here PHI-A or PHI-I) used for the Agrobacterium suspension are added into a 2 ml microcentrifuge tube. Immature embryos are isolated from a sterilized ear with a sterile spatula (Baxter Scientific Products S1565) and dropped directly into the medium in the tube. A total of about 100 embryos are placed in the tube. The optimal size of the embryos is about 1.0–1.2 mm. The cap is then closed on the tube and the tube vortexed with a Vortex Mixer (Baxter Scientific Products S8223-1) for 5 sec. at maximum speed. The medium is removed and 2 ml of fresh medium are added and the vortexing repeated. All of the medium is drawn off and 1 ml of Agrobacterium suspension is added to the embryos and the tube vortexed for 30 sec. The tube is allowed to stand for 5 min. in the hood. The suspension of Agrobacterium and embryos was poured into a Petri plate containing either PHI-B medium [CHU(N6) basal salts (Sigma C-1416) 4.0 g/l; Eriksson's vitamin mix (1000×, Sigma-1511) 1.0 ml/l; thiamine.HCl 0.5 mg/l; 2,4-D 1.5 mg/l; L-proline 0.69 g/l; silver nitrate 0.85 mg/l; gelrite (Sigma) 3.0 g/l; sucrose 30.0 g/l; acetosyringone 100 $\mu$M; pH 5.8], for the PHI basic medium system, or PHI-J medium [MS Salts 4.3 g/l; nicotinic acid 0.50 mg/l; pyridoxine HCl 0.50 mg/l; thiamine.HCl 1.0 mg/l; myo-inositol 100.0 mg/l; 2,4-D 1.5 mg/l; sucrose 20.0 g/l; glucose 10.0 g/l; L-proline 0.70 g/l; MES (Sigma) 0.50 g/l; 8.0 g/l agar (Sigma A-7049, purified) and 100 $\mu$M acetosyringone with a final pH of 5.8 for the PHI combined medium system. Any embryos left in the tube are transferred to the plate using a sterile spatula. The Agrobacterium suspension is drawn off and the embryos placed axis side down on the media. The plate is sealed with Parafilm tape or Pylon Vegetative Combine Tape (product named "E.G.CUT" and is available in 18 mm×50 m sections; Kyowa Ltd., Japan) and incubated in the dark at 23–25° C. for about 3 days of co-cultivation.

Resting, selection and regeneration steps:

For the resting step, all of the embryos are transferred to a new plate containing PHI-C medium [CHU(N6) basal salts (Sigma C-1416) 4.0 g/l; Eriksson's vitamin mix (1000× Sigma-1511) 1.0 ml/l; thiamine.HCl 0.5 mg/l; 2,4-D 1.5 mg/l; L-proline 0.69 g/l; sucrose 30.0 g/l; MES buffer (Sigma) 0.5 g/l; agar (Sigma A-7049, purified) 8.0 g/l; silver nitrate 0.85 mg/l; carbenicillin 100 mg/l; pH 5.8]. The plate is sealed with Parafilm or Pylon tape and incubated in the dark at 28° C. for 3–5 days.

Longer co-cultivation periods may compensate for the absence of a resting step since the resting step, like the co-cultivation step, provides a period of time for the embryo to be cultured in the absence of a selective agent. Those of ordinary skill in the art can readily test combinations of co-cultivation and resting times to optimize or improve the transformation frequency of other inbreds without undue experimentation.

For selection, all of the embryos are then transferred from the PHI-C medium to new plates containing PHI-D medium, as a selection medium, [CHU(N6) basal salts (SIGMA C-1416) 4.0 g/l; Eriksson's vitamin mix (1000×, Sigma-1511) 1.0 ml/l; thiamine.HCl 0.5 mg/l; 2,4-D 1.5 mg/l; L-proline 0.69 g/l; sucrose 30.0 g/l; MES buffer 0.5 g/l; agar (Sigma A-7049, purified) 8.0 g/l; silver nitrate 0.85 mg/l; carbenicillin (ICN, Costa Mesa, Calif.) 100 mg/l; bialaphos (Meiji Seika K.K., Tokyo, Japan) 1.5 mg/l for the first two weeks followed by 3 mg/l for the remainder of the time.; pH 5.8] putting about 20 embryos onto each plate. The plates are sealed as described above and incubated in the dark at 28° C. for the first two weeks of selection. The embryos are transferred to fresh selection medium at two-week intervals. The tissue is subcultured by transferring to fresh selection medium for a total of about 2 months. The herbicide-resistant calli are then "bulked up" by growing on the same medium for another two weeks until the diameter of the calli is about 1.5–2 cm.

For regeneration, the calli are then cultured on PHI-E medium [MS salts 4.3 g/l; myo-inositol 0.1 g/l; nicotinic acid 0.5 mg/l, thiamine.HCl 0.1 mg/l, Pyridoxine.HCl 0.5 mg/l, Glycine 2.0 mg/l, Zeatin 0.5 mg/l, sucrose 60.0 g/l, Agar (Sigma, A-7049) 8.0 g/l, Indoleacetic acid (IAA, Sigma) 1.0 mg/l, Abscisic acid (ABA, Sigma) 0.1 $\mu$M, Bialaphos 3 mg/l, carbenicillin 100 mg/l adjusted to pH 5.6] in the dark at 28° C. for 1–3 weeks to allow somatic embryos to mature. The calli are then cultured on PHI-F medium (MS salts 4.3 g/l; myo-inositol 0.1 g/l; Thiamine.HCl 0.1 mg/l, Pyridoxine.HCl 0.5 mg/l, Glycine 2.0 mg/l, nicotinic acid 0.5 mg/l; sucrose 40.0 g/l; gelrite 1.5 g/l; pH 5.6] at 25° C. under a daylight schedule of 16 hrs. light (270 uE m$^{-2}$sec$^{-1}$) and 8 hrs. dark until shoots and roots develop. Each small plantlet is then transferred to a 25×150 mm tube containing PHI-F medium and grown under the same conditions for approximately another week. The plants are transplanted to pots with soil mixture in a greenhouse. GUS+ events are determined at the callus stage or regenerated plant stage.

For Hi-II a preferred optimized protocol was $0.5\times10^9$ cfu/ml Agrobacterium (Table 6), a 3–5 day resting step (Example 5), and no AgNO$_3$ in the infection medium (PHI-A medium). The examples provide a variety of experiments that similarly teach those of ordinary skill in the art to optimize transformation frequencies for other maize lines.

It will be appreciated by those skilled in the art that while the invention has been described above in connection with particular embodiments and examples, the invention is not necessarily so limited and that numerous other embodiments, examples, uses, modifications and departures from the embodiments, examples and uses may be made without departing from the inventive scope of this application.

What is claimed is:

1. An isolated nucleic acid comprising a polynucleotide that encodes a polypeptide of SEQ ID NO: 14.

2. An isolated ribonucleic acid sequence encoding a polypeptide of claim 1.

3. An isolated nucleic acid comprising a polynucleotide encoding a starch synthase from *Canna edulis* or a complement thereof.

4. A method for modulating the level of starch synthase protein in a plant, comprising:
   (a) stably transforming a plant cell with a starch synthase polynucleotide of claim 3 operably linked to a promoter, wherein the polynucleotide is in sense or antisense orientation;
   (b) growing the plant cell under plant growing conditions to produce a regenerated plant capable of expressing the polynucleotide for a time sufficient to modulate the level of starch synthase protein in the plant.

5. The method of claim 4, wherein the plant is maize, soybean, alfalfa, sunflower, Brassica, cotton, sorghum, wheat, barley, millet, rice, cassava, potato, Arabidopsis, tomato, pepper, apple, spinach, or lettuce.

6. The method of claim 4, wherein starch synthase protein is increased.

7. The method of claim 4, wherein starch synthase protein is decreased.

8. A method for modulating the morphology and/or amount of starch in a plant, comprising:
   (a) stably transforming a plant cell with a starch synthase polynucleotide of claim 3 operably linked to a promoter, wherein the polynucleotide is in sense or antisense orientation;
   (b) growing the plant cell under plant growing conditions to produce a regenerated plant capable of expressing the polynucleotide for a time sufficient to modulate the morphology and/or amount of starch in the plant.

9. The method of claim 8, wherein the starch exhibits altered degree of crystallinity.

10. The method of claim 8, wherein the starch exhibits altered temperature of gelatinization.

11. The method of claim 8, wherein the starch exhibits altered density.

12. The method of claim 8, wherein the starch exhibits altered digestibility.

13. The method of claim 8, wherein the starch exhibits altered level of covalently bound phosphate.

14. The method of claim 8, wherein the starch exhibits altered branching patterns.

15. The method of claim 8, wherein the starch exhibits altered degree of polymerization.

16. The method of claim 8, wherein the starch exhibits altered average chain length.

17. The method of claim 8, wherein the starch exhibits altered rate of retrogradation.

18. The method of claim 8, wherein the plant is *Zea mays*.

19. The method of claim 18, wherein the starch exhibits altered granule diameter in the range of 31 μm to 100 μm.

20. A vector comprising at least one nucleic acid of claim 1.

21. An expression cassette comprising at least one nucleic acid of claim 1 operably linked to a promoter, wherein the nucleic acid is in sense or antisense orientation.

22. A non-human host cell into which is introduced at least one expression cassette of claim 21.

23. The host cell of claim 22 that is a plant cell.

24. A transgenic plant comprising at least one expression cassette of claim 21.

25. The transgenic plant of claim 24, wherein the plant is maize, soybean, alfalfa, sunflower, Brassica, cotton, sorghum, wheat, barley, millet, rice, cassava, potato, Arabidopsis, tomato, pepper, apple, spinach, or lettuce.

26. A seed from the transgenic plant of claim 24.

27. The seed of claim 26, wherein the seed is from maize, soybean, alfalfa, sunflower, Brassica, cotton, sorghum, wheat, barley, millet, rice, cassava, potato, Arabidopsis, tomato, pepper, apple, spinach, or lettuce.

28. An isolated nucleic acid comprising a polynucleotide having at least 73% sequence identity to SEQ ID NO:13, or a complement thereof, wherein the % sequence identity is based on the entire coding sequence and is determined by BLAST 2.0 using default parameters, wherein said polynucleotide encodes a starch synthase.

29. A vector comprising at least one nucleic acid of claim 28.

30. An expression cassette comprising at least one nucleic acid of claim 28 operably linked to a promoter, wherein the nucleic acid is in sense or antisense orientation.

31. A host cell into which is introduced at least one expression cassette of claim 30.

32. A transgenic plant comprising at least one expression cassette of claim 30.

33. A seed from the transgenic plant of claim 32.

34. An isolated nucleic acid comprising a polynucleotide which hybridizes under high stringency conditions to a polynucleotide having the sequence set forth in SEQ ID NO:13, or a complement thereof.

35. A vector comprising at least one nucleic acid of claim 34.

36. An expression cassette comprising at least one nucleic acid of claim 34 operably linked to a promoter, wherein the nucleic acid is in sense or antisense orientation.

37. A non-human host cell into which is introduced at least one expression cassette of claim 36.

38. A transgenic plant comprising at least one expression cassette of claim 36.

39. A seed from the transgenic plant of claim 38.

40. An isolated nucleic acid comprising a polynucleotide comprising the sequence set forth in SEQ ID NO:13, or a complement thereof.

41. A vector comprising at least one nucleic acid of claim 40.

42. An expression cassette comprising at least one nucleic acid of claim 40 operably linked to a promoter, wherein the nucleic acid is in sense or antisense orientation.

43. A host cell into which is introduced at least one expression cassette of claim 42.

44. A transgenic plant comprising at least one expression cassette of claim 42.

45. The transgenic plant of claim 44, wherein the plant is maize, soybean, alfalfa, sunflower, Brassica, cotton, sorghum, wheat, barley, millet, rice, cassava, potato, Arabidopsis, tomato, pepper, apple, spinach, or lettuce.

46. A seed from the transgenic plant of claim 44.

47. The seed of claim 46, wherein the seed is from maize, soybean, alfalfa, sunflower, Brassica, cotton, sorghum, wheat, barley, millet, rice, cassava, potato, Arabidopsis, tomato, pepper, apple, spinach, or lettuce.

48. A vector comprising at least one nucleic acid of claim 3.

49. An expression cassette comprising at least one nucleic acid of claim 3 operably linked to a promoter, wherein the nucleic acid is in sense or antisense orientation.

50. A non-human host cell into which is introduced at least one expression cassette of claim 49.

51. The host cell of claim 50 that is a plant cell.

52. A transgenic plant comprising at least one expression cassette of claim 49.

53. The transgenic plant of claim 52, wherein the plant is maize, soybean, alfalfa, sunflower, Brassica, cotton, sorghum, wheat, barley, millet, rice, cassava, potato, Arabidopsis, tomato, pepper, apple, spinach, or lettuce.

54. A seed from the transgenic plant of claim 53.

55. The seed of claim 54, wherein the seed is from maize, soybean, alfalfa, sunflower, Brassica, cotton, sorghum, wheat, barley, millet, rice, cassava, potato, Arabidopsis, tomato, pepper, apple, spinach, or lettuce.

56. The method of claim 8, wherein the starch synthase polynucleotide comprises SEQ ID NO:13 or functional derivatives thereof.

\* \* \* \* \*

SEQUENCE LISTING

```
<160> NUMBER OF SEQ ID NOS: 28

<210> SEQ ID NO 1
<211> LENGTH: 2202
<212> TYPE: DNA
<213> ORGANISM: Curcuma zedoaria
<220> FEATURE:
```

-continued

```
<221> NAME/KEY: CDS
<222> LOCATION: (130)...(1974)

<400> SEQUENCE: 1
cactcatcac ttccgctgca agccagagag agaaagagcg atcgagctcc ggcggtgatt      60
cttcctcgca tctctgcttc tctctctctc tcctcctttg atcgaagaga tcgccgtgag     120 ggtatcccc atg gcc atg cct tct gtg act gca tca cac ttc att gct aaa    171
          Met Ala Met Pro Ser Val Thr Ala Ser His Phe Ile Ala Lys
            1               5                  10 acc cca tgc tcc agc tac aat gga gct agt gat ttg gag ggt ttg gcc     219
Thr Pro Cys Ser Ser Tyr Asn Gly Ala Ser Asp Leu Glu Gly Leu Ala
 15              20                  25                  30 ttc caa atc aga agg atc cct tat ctg agt aac cat gcc agt act ttt     267
Phe Gln Ile Arg Arg Ile Pro Tyr Leu Ser Asn His Ala Ser Thr Phe
                 35                  40                  45 gaa gga ctg aga tcg cgg aac caa atg aat tca cgt cca atg cag tgt     315
Glu Gly Leu Arg Ser Arg Asn Gln Met Asn Ser Arg Pro Met Gln Cys
             50                  55                  60 gca aag gca act act agg caa gtg agg aag gga atc caa cat gct agc     363
Ala Lys Ala Thr Thr Arg Gln Val Arg Lys Gly Ile Gln His Ala Ser
         65                  70                  75 cga aga ccc tct gta atc tgt gca agt gga atg aac ttg atc ttt gtt     411
Arg Arg Pro Ser Val Ile Cys Ala Ser Gly Met Asn Leu Ile Phe Val
 80                  85                  90 gct gct gag gtg gct ccg tgg agt aaa act gga ggg ctt ggt gat gtt     459
Ala Ala Glu Val Ala Pro Trp Ser Lys Thr Gly Gly Leu Gly Asp Val
 95                 100                 105                 110 ctt gga ggt ttg cca ccg gcc atg gcg gca aag gga cac agg gtg atg     507
Leu Gly Gly Leu Pro Pro Ala Met Ala Ala Lys Gly His Arg Val Met
                115                 120                 125 act ata gca ccg cga cat gac caa tac aaa gat gga tgg gat acg gct     555
Thr Ile Ala Pro Arg His Asp Gln Tyr Lys Asp Gly Trp Asp Thr Ala
            130                 135                 140 gtc ttt gtc gag ttg aaa gtt ggt gat aga att gaa act gtt cgc ttt     603
Val Phe Val Glu Leu Lys Val Gly Asp Arg Ile Glu Thr Val Arg Phe
        145                 150                 155 ttc cac tgc tac aaa agg gga gtt gat cgg gtg ttt gtg gat cac cct     651
Phe His Cys Tyr Lys Arg Gly Val Asp Arg Val Phe Val Asp His Pro
160                 165                 170 ctc ttc ctt gag aag gtt tgg gga aaa act gga gga aag ata tat ggt     699
Leu Phe Leu Glu Lys Val Trp Gly Lys Thr Gly Gly Lys Ile Tyr Gly
175                 180                 185                 190 cct gtc aca aga act gat tat gaa gac aac cag cta agg ttc tgt ctt     747
Pro Val Thr Arg Thr Asp Tyr Glu Asp Asn Gln Leu Arg Phe Cys Leu
                195                 200                 205 ctg tgt ttg gca act ctg gaa act cca agg gtt ctg aat ccc aac aat     795
Leu Cys Leu Ala Thr Leu Glu Thr Pro Arg Val Leu Asn Pro Asn Asn
            210                 215                 220 aac aaa tat cat tct gga cca aaa ggt gaa gat tta ttc att gct aac     843
Asn Lys Tyr His Ser Gly Pro Lys Gly Glu Asp Leu Phe Ile Ala Asn
        225                 230                 235 gat tgg cat act gct cta tta cct tgc tat tta aag acc att gta tat     891
Asp Trp His Thr Ala Leu Leu Pro Cys Tyr Leu Lys Thr Ile Val Tyr
240                 245                 250 caa gcc cat gga ata tac aaa aat gct aaa gtt gct ttc tgc att cat     939
Gln Ala His Gly Ile Tyr Lys Asn Ala Lys Val Ala Phe Cys Ile His
255                 260                 265                 270 aat att gcg tat cag gga cgg ttt gcc ttt gaa gat ttt tcg cgt ctc     987
Asn Ile Ala Tyr Gln Gly Arg Phe Ala Phe Glu Asp Phe Ser Arg Leu
```

```
                    275                 280                 285
aat ctc cct gat aca ttc aag tct tct ttt gat ttc atc gat ggc tat    1035
Asn Leu Pro Asp Thr Phe Lys Ser Ser Phe Asp Phe Ile Asp Gly Tyr
                290                 295                 300 gca aaa cca ata aaa gga agg aaa atc aac tgg atg aag gcg gga att    1083
Ala Lys Pro Ile Lys Gly Arg Lys Ile Asn Trp Met Lys Ala Gly Ile
            305                 310                 315 ata gaa tca gat cgt gca ttg act gtg agc cca tac tat gcc cag gaa    1131
Ile Glu Ser Asp Arg Ala Leu Thr Val Ser Pro Tyr Tyr Ala Gln Glu
        320                 325                 330 ctc gtc tca gga atc gat aag ggc gtc gag ttg gac aat ata ctg cgc    1179
Leu Val Ser Gly Ile Asp Lys Gly Val Glu Leu Asp Asn Ile Leu Arg
335                 340                 345                 350 ttg aaa acc atc tgt ggc atc ata aat gga atg gac acc aac gag tgg    1227
Leu Lys Thr Ile Cys Gly Ile Ile Asn Gly Met Asp Thr Asn Glu Trp
                355                 360                 365 aat ccc tca aca gac aaa tac ata aca gca aat tac gac gca acc act    1275
Asn Pro Ser Thr Asp Lys Tyr Ile Thr Ala Asn Tyr Asp Ala Thr Thr
            370                 375                 380 gta atg gag gca aag cca ctc aac aag gaa gct ttg caa gct gag gtt    1323
Val Met Glu Ala Lys Pro Leu Asn Lys Glu Ala Leu Gln Ala Glu Val
        385                 390                 395 gga ctg ccc gtc aac agt aaa atc cct gtg ata gct ttc att ggc aga    1371
Gly Leu Pro Val Asn Ser Lys Ile Pro Val Ile Ala Phe Ile Gly Arg
    400                 405                 410 cta gaa gaa caa aag ggt tca gac att cta gct gaa gca att cca aag    1419
Leu Glu Glu Gln Lys Gly Ser Asp Ile Leu Ala Glu Ala Ile Pro Lys
415                 420                 425                 430 ttc ttc gat cag gat gtt caa gtg ata gtt ctc ggt act ggt aaa aag    1467
Phe Phe Asp Gln Asp Val Gln Val Ile Val Leu Gly Thr Gly Lys Lys
                435                 440                 445 aag tta gag cgc caa ctt gca ttg ctc gag gac gag ttc cca gac aaa    1515
Lys Leu Glu Arg Gln Leu Ala Leu Leu Glu Asp Glu Phe Pro Asp Lys
            450                 455                 460 ttc aga gct cat atg aag ttc aat att cct ttg gct cat gga atc atg    1563
Phe Arg Ala His Met Lys Phe Asn Ile Pro Leu Ala His Gly Ile Met
        465                 470                 475 gcg ggt gct gat atc ctt gtt att ccc agt agg ttc gaa cca tgc ggt    1611
Ala Gly Ala Asp Ile Leu Val Ile Pro Ser Arg Phe Glu Pro Cys Gly
    480                 485                 490 ctc att cag ctc cag ggc atg aga tac gga acc cct tcc atg tgc acc    1659
Leu Ile Gln Leu Gln Gly Met Arg Tyr Gly Thr Pro Ser Met Cys Thr
495                 500                 505                 510 acg act ggt ggg ctc gtc gac act gtc aaa gaa ggc atc aca ggt ttc    1707
Thr Thr Gly Gly Leu Val Asp Thr Val Lys Glu Gly Ile Thr Gly Phe
                515                 520                 525 cac atg ggt ccc ttc agt gtg gag tgc gac att gcc gac gag gcc gac    1755
His Met Gly Pro Phe Ser Val Glu Cys Asp Ile Ala Asp Glu Ala Asp
            530                 535                 540 gtg cta aag att gtg gaa gca gtg aag aga gcc ctt atg gtt tat gga    1803
Val Leu Lys Ile Val Glu Ala Val Lys Arg Ala Leu Met Val Tyr Gly
        545                 550                 555 acg cct gct ttc gag gag atg ata cag aac tgc atg gct caa gat ttc    1851
Thr Pro Ala Phe Glu Glu Met Ile Gln Asn Cys Met Ala Gln Asp Phe
    560                 565                 570 tcc tgg aag ggg cca gca aag gaa tgg gag aag ttc ttg ctg agc ctt    1899
Ser Trp Lys Gly Pro Ala Lys Glu Trp Glu Lys Phe Leu Leu Ser Leu
575                 580                 585                 590 ggg ctc gag ggt agt gaa gct gga att gaa ggc gag gaa gta gct cct    1947
```

```
Gly Leu Glu Gly Ser Glu Ala Gly Ile Glu Gly Glu Val Ala Pro
            595                 600                 605 ctc gcc aag gaa aac gtg gcc act cca tgaaactgat catcgagttg              1994
Leu Ala Lys Glu Asn Val Ala Thr Pro
            610                 615 tgttcctcac tgcattttca caataaatgg tttgttaaat agtagagata tcatctatca      2054
ctgcaacgtg ttgtaaattt gttcttgtaa ataagccgt gtaatctaac tctaaggccg       2114
tttgttggcg taatgcagat gctatctgtt ttaattttaa aaaaaaaaaa aaaaaaaaa       2174 aaaaaaaaaa aaaaaaaaaa aaaaaaa                                         2202

<210> SEQ ID NO 2
<211> LENGTH: 615
<212> TYPE: PRT
<213> ORGANISM: Curcuma zedoaria

<400> SEQUENCE: 2

Met Ala Met Pro Ser Val Thr Ala Ser His Phe Ile Ala Lys Thr Pro
  1               5                  10                  15

Cys Ser Ser Tyr Asn Gly Ala Ser Asp Leu Glu Gly Leu Ala Phe Gln
             20                  25                  30

Ile Arg Arg Ile Pro Tyr Leu Ser Asn His Ala Ser Thr Phe Glu Gly
         35                  40                  45

Leu Arg Ser Arg Asn Gln Met Asn Ser Arg Pro Met Gln Cys Ala Lys
     50                  55                  60

Ala Thr Thr Arg Gln Val Arg Lys Gly Ile Gln His Ala Ser Arg Arg
 65                  70                  75                  80

Pro Ser Val Ile Cys Ala Ser Gly Met Asn Leu Ile Phe Val Ala Ala
                 85                  90                  95

Glu Val Ala Pro Trp Ser Lys Thr Gly Gly Leu Gly Asp Val Leu Gly
            100                 105                 110

Gly Leu Pro Pro Ala Met Ala Ala Lys Gly His Arg Val Met Thr Ile
        115                 120                 125

Ala Pro Arg His Asp Gln Tyr Lys Asp Gly Trp Asp Thr Ala Val Phe
    130                 135                 140

Val Glu Leu Lys Val Gly Asp Arg Ile Glu Thr Val Arg Phe His
145                 150                 155                 160

Cys Tyr Lys Arg Gly Val Asp Arg Val Phe Val Asp His Pro Leu Phe
                165                 170                 175

Leu Glu Lys Val Trp Gly Lys Thr Gly Gly Lys Ile Tyr Gly Pro Val
            180                 185                 190

Thr Arg Thr Asp Tyr Glu Asp Asn Gln Leu Arg Phe Cys Leu Leu Cys
        195                 200                 205

Leu Ala Thr Leu Glu Thr Pro Arg Val Leu Asn Pro Asn Asn Asn Lys
    210                 215                 220

Tyr His Ser Gly Pro Lys Gly Glu Asp Leu Phe Ile Ala Asn Asp Trp
225                 230                 235                 240

His Thr Ala Leu Leu Pro Cys Tyr Leu Lys Thr Ile Val Tyr Gln Ala
                245                 250                 255

His Gly Ile Tyr Lys Asn Ala Lys Val Ala Phe Cys Ile His Asn Ile
            260                 265                 270

Ala Tyr Gln Gly Arg Phe Ala Phe Glu Asp Phe Ser Arg Leu Asn Leu
        275                 280                 285

Pro Asp Thr Phe Lys Ser Ser Phe Asp Phe Ile Asp Gly Tyr Ala Lys
    290                 295                 300
```

-continued

Pro Ile Lys Gly Arg Lys Ile Asn Trp Met Lys Ala Gly Ile Ile Glu
305                 310                 315                 320

Ser Asp Arg Ala Leu Thr Val Ser Pro Tyr Tyr Ala Gln Glu Leu Val
            325                 330                 335

Ser Gly Ile Asp Lys Gly Val Glu Leu Asp Asn Ile Leu Arg Leu Lys
            340                 345                 350

Thr Ile Cys Gly Ile Ile Asn Gly Met Asp Thr Asn Glu Trp Asn Pro
            355                 360                 365

Ser Thr Asp Lys Tyr Ile Thr Ala Asn Tyr Asp Ala Thr Thr Val Met
370                 375                 380

Glu Ala Lys Pro Leu Asn Lys Glu Ala Leu Gln Ala Glu Val Gly Leu
385                 390                 395                 400

Pro Val Asn Ser Lys Ile Pro Val Ile Ala Phe Ile Gly Arg Leu Glu
            405                 410                 415

Glu Gln Lys Gly Ser Asp Ile Leu Ala Glu Ala Ile Pro Lys Phe Phe
            420                 425                 430

Asp Gln Asp Val Gln Val Ile Val Leu Gly Thr Gly Lys Lys Lys Leu
            435                 440                 445

Glu Arg Gln Leu Ala Leu Leu Glu Asp Glu Phe Pro Asp Lys Phe Arg
450                 455                 460

Ala His Met Lys Phe Asn Ile Pro Leu Ala His Gly Ile Met Ala Gly
465                 470                 475                 480

Ala Asp Ile Leu Val Ile Pro Ser Arg Phe Glu Pro Cys Gly Leu Ile
            485                 490                 495

Gln Leu Gln Gly Met Arg Tyr Gly Thr Pro Ser Met Cys Thr Thr Thr
            500                 505                 510

Gly Gly Leu Val Asp Thr Val Lys Glu Gly Ile Thr Gly Phe His Met
            515                 520                 525

Gly Pro Phe Ser Val Glu Cys Asp Ile Ala Asp Glu Ala Asp Val Leu
530                 535                 540

Lys Ile Val Glu Ala Val Lys Arg Ala Leu Met Val Tyr Gly Thr Pro
545                 550                 555                 560

Ala Phe Glu Glu Met Ile Gln Asn Cys Met Ala Gln Asp Phe Ser Trp
            565                 570                 575

Lys Gly Pro Ala Lys Glu Trp Glu Lys Phe Leu Leu Ser Leu Gly Leu
            580                 585                 590

Glu Gly Ser Glu Ala Gly Ile Gly Gly Glu Val Ala Pro Leu Ala
            595                 600                 605

Lys Glu Asn Val Ala Thr Pro
610                 615

<210> SEQ ID NO 3
<211> LENGTH: 25
<212> TYPE: DNA
<213> ORGANISM: Curcuma zedoaria

<400> SEQUENCE: 3
atggccatgc cttctgtgac tgcat                                          25

<210> SEQ ID NO 4
<211> LENGTH: 25
<212> TYPE: DNA
<213> ORGANISM: Curcuma zedoaria

<400> SEQUENCE: 4

-continued

```
tcatggagtg gccacgtttt ccttg                                           25
```

<210> SEQ ID NO 5
<211> LENGTH: 2348
<212> TYPE: DNA
<213> ORGANISM: Curcuma zedoaria
<220> FEATURE:
<221> NAME/KEY: CDS
<222> LOCATION: (36)...(2105)

<400> SEQUENCE: 5

```
ccaccaccgt aactaccacg gccacttcgc tcagc atg ttc tcc cac ctc cta      53
                                      Met Phe Ser His Leu Leu
                                      1               5 tcc tct cct cca gcg ccg ccg ccc ggc gcg gcc agc tgc cgc ctc        101
Ser Ser Pro Pro Ala Pro Pro Pro Gly Ala Ala Ser Cys Arg Leu
            10                  15                  20 ctg cac ggc ggg gct cgc cct ctt ggc cac tct ccg ctt tgc tgg gcg    149
Leu His Gly Gly Ala Arg Pro Leu Gly His Ser Pro Leu Cys Trp Ala
        25                  30                  35 aat cct ctc tgt acg agc cga ttt atg gcg ggt ctt tca gaa gtc aag    197
Asn Pro Leu Cys Thr Ser Arg Phe Met Ala Gly Leu Ser Glu Val Lys
    40                  45                  50 aaa ggg agc aaa atc aca ctc aaa cat atc gat cac act gga agt gct    245
Lys Gly Ser Lys Ile Thr Leu Lys His Ile Asp His Thr Gly Ser Ala
55                  60                  65                  70 cgc aca atg agg ttt ctt aat gct tta tac cat gga caa tca gcg gat    293
Arg Thr Met Arg Phe Leu Asn Ala Leu Tyr His Gly Gln Ser Ala Asp
                75                  80                  85 cta gtt cca atc aac cac agg gga aag tct tca ggc gca gtt ggg aga    341
Leu Val Pro Ile Asn His Arg Gly Lys Ser Ser Gly Ala Val Gly Arg
            90                  95                  100 agc aat att aat gat ata caa gag gat agc aat caa gat gtt gac att    389
Ser Asn Ile Asn Asp Ile Gln Glu Asp Ser Asn Gln Asp Val Asp Ile
        105                 110                 115 gcc gat gat tct gtt gca caa aca atg gaa caa agc aag aag gtg ttg    437
Ala Asp Asp Ser Val Ala Gln Thr Met Glu Gln Ser Lys Lys Val Leu
    120                 125                 130 gaa atg cag agg aac ctg ctg caa cag att att gaa aag aga aat ttc    485
Glu Met Gln Arg Asn Leu Leu Gln Gln Ile Ile Glu Lys Arg Asn Phe
135                 140                 145                 150 tct gaa gag aca gaa tct tat gtc aag aaa gat gag aac ctt gga att    533
Ser Glu Glu Thr Glu Ser Tyr Val Lys Lys Asp Glu Asn Leu Gly Ile
                155                 160                 165 tat gca gaa gca tat atg caa acc tca aac aat caa caa gaa gct cca    581
Tyr Ala Glu Ala Tyr Met Gln Thr Ser Asn Asn Gln Gln Glu Ala Pro
            170                 175                 180 cca gaa gaa gga aat ctg aac tct cct cct ttg gct ggt cca aat gta    629
Pro Glu Glu Gly Asn Leu Asn Ser Pro Pro Leu Ala Gly Pro Asn Val
        185                 190                 195 atg aat atc ata ttg gta gct gca gaa tgt gca cca tgg tct aaa aca    677
Met Asn Ile Ile Leu Val Ala Ala Glu Cys Ala Pro Trp Ser Lys Thr
    200                 205                 210 ggt ggg ctt gga gat gtt gtt gga gct tta cct aaa gca ttg gcc aag    725
Gly Gly Leu Gly Asp Val Val Gly Ala Leu Pro Lys Ala Leu Ala Lys
215                 220                 225                 230 aga gga cat cgt gtc atg gta gtg tct cca aga tat gga aac tat cct    773
Arg Gly His Arg Val Met Val Val Ser Pro Arg Tyr Gly Asn Tyr Pro
                235                 240                 245 gaa cct aag gaa ata ggg aat ctt aaa agg tac aag gtt gat gga cag    821
Glu Pro Lys Glu Ile Gly Asn Leu Lys Arg Tyr Lys Val Asp Gly Gln
```

-continued

| | | | |
|---|---|---|---|
| gac atg gag att aaa tac tat cat act tac atc gat tct gtt gat ttt<br>Asp Met Glu Ile Lys Tyr Tyr His Thr Tyr Ile Asp Ser Val Asp Phe<br>265 270 275 | | | 869 |
| gtc ttc atc gat agt cct att ttc cgc cat att gga aat gat ata tat<br>Val Phe Ile Asp Ser Pro Ile Phe Arg His Ile Gly Asn Asp Ile Tyr<br>280 285 290 | | | 917 |
| ggt gga aac cga gtg gac att ttg aag aga atg gta ttg ttc tgc aaa<br>Gly Gly Asn Arg Val Asp Ile Leu Lys Arg Met Val Leu Phe Cys Lys<br>295 300 305 310 | | | 965 |
| gca gca gtt gag gtt cct tgg cat gtc cca tgt ggt gga ttc tgt tat<br>Ala Ala Val Glu Val Pro Trp His Val Pro Cys Gly Gly Phe Cys Tyr<br>315 320 325 | | | 1013 |
| gga gat ggg aat ttg gtt ttc att gcc aac gat tgg cat acc tcc tta<br>Gly Asp Gly Asn Leu Val Phe Ile Ala Asn Asp Trp His Thr Ser Leu<br>330 335 340 | | | 1061 |
| ctt cca gtt tat ttg aag gca tgt ttc cgt gat cgt gga tta atg aca<br>Leu Pro Val Tyr Leu Lys Ala Cys Phe Arg Asp Arg Gly Leu Met Thr<br>345 350 355 | | | 1109 |
| tac gct cgc tgt ctc ttg gtt att cac aac att gca cat cag ggt cgt<br>Tyr Ala Arg Cys Leu Leu Val Ile His Asn Ile Ala His Gln Gly Arg<br>360 365 370 | | | 1157 |
| ggt ccg cta gat gac ttc tca tat gtg gat ttg cca cat gat cac att<br>Gly Pro Leu Asp Asp Phe Ser Tyr Val Asp Leu Pro His Asp His Ile<br>375 380 385 390 | | | 1205 |
| gac tcg ttt aga ctg gat gat cct gtt gga ggt gag cat ttt aac att<br>Asp Ser Phe Arg Leu Asp Asp Pro Val Gly Gly Glu His Phe Asn Ile<br>395 400 405 | | | 1253 |
| ttt gca gct ggt ata aga gct gct gac cgt gtg gtt aca gtt agc cat<br>Phe Ala Ala Gly Ile Arg Ala Ala Asp Arg Val Val Thr Val Ser His<br>410 415 420 | | | 1301 |
| ggc tat gct tgg gag tta aaa aca tct gaa ggt ggt tgg gga ttg cat<br>Gly Tyr Ala Trp Glu Leu Lys Thr Ser Glu Gly Gly Trp Gly Leu His<br>425 430 435 | | | 1349 |
| gag atc atc aac gag tgc cat tgg aaa ttc cat ggt att gta aat gga<br>Glu Ile Ile Asn Glu Cys His Trp Lys Phe His Gly Ile Val Asn Gly<br>440 445 450 | | | 1397 |
| atc gat acc cat agt tgg aat cca aaa ttt gac gct cac tta aat tct<br>Ile Asp Thr His Ser Trp Asn Pro Lys Phe Asp Ala His Leu Asn Ser<br>455 460 465 470 | | | 1445 |
| gat ggt tac acc aac ttc acc ctg gaa act ctt gaa atg gga aag gcc<br>Asp Gly Tyr Thr Asn Phe Thr Leu Glu Thr Leu Glu Met Gly Lys Ala<br>475 480 485 | | | 1493 |
| cag tgc aag gct gct ttg caa cga gag ttt ggt ctg cct gtt cgt gac<br>Gln Cys Lys Ala Ala Leu Gln Arg Glu Phe Gly Leu Pro Val Arg Asp<br>490 495 500 | | | 1541 |
| gac gtt cct att ctt gcc ttc att ggg aga tta gac cat caa aaa ggt<br>Asp Val Pro Ile Leu Ala Phe Ile Gly Arg Leu Asp His Gln Lys Gly<br>505 510 515 | | | 1589 |
| ata gat ctc ata gcg gag gcc atg cac tgg ctc gtc ggt caa gat cta<br>Ile Asp Leu Ile Ala Glu Ala Met His Trp Leu Val Gly Gln Asp Leu<br>520 525 530 | | | 1637 |
| cag ata atc atg ctg ggc act ggg agg cca gac ctc gag gat atg ctt<br>Gln Ile Ile Met Leu Gly Thr Gly Arg Pro Asp Leu Glu Asp Met Leu<br>535 540 545 550 | | | 1685 |
| cga aga ttt gaa cgt gag cat cgc ggt aag gtc agg gga tgg gtt ggg<br>Arg Arg Phe Glu Arg Glu His Arg Gly Lys Val Arg Gly Trp Val Gly<br>555 560 565 | | | 1733 |
| ttc tca gtg aaa atg gct cat cgg atc aca gca ggt gct gat gcc cta<br> | | | 1781 |

```
                Phe Ser Val Lys Met Ala His Arg Ile Thr Ala Gly Ala Asp Ala Leu
                                570                 575                 580 ctg atg ccc tcc agg ttc gaa cct tgt gga ttg aac caa ctt cac gct              1829
Leu Met Pro Ser Arg Phe Glu Pro Cys Gly Leu Asn Gln Leu His Ala
            585                 590                 595 atg atg tac gga aca att cct gtt gtg cat gca gta ggt ggt ctt cga              1877
Met Met Tyr Gly Thr Ile Pro Val Val His Ala Val Gly Gly Leu Arg
        600                 605                 610 gat act gtg caa cag ttt gat ccg ttc aat gag aca ggt ttg gga tgg              1925
Asp Thr Val Gln Gln Phe Asp Pro Phe Asn Glu Thr Gly Leu Gly Trp
615                 620                 625                 630 acc ttt gac agg gca gag gca cat agg atg ata gtg gca ctc ggc cat              1973
Thr Phe Asp Arg Ala Glu Ala His Arg Met Ile Val Ala Leu Gly His
                635                 640                 645 tgt cta aac aca tat cgg aat tac aag gag agc tgg gtg gga ttg cag              2021
Cys Leu Asn Thr Tyr Arg Asn Tyr Lys Glu Ser Trp Val Gly Leu Gln
            650                 655                 660 aag cga ggg atg atg cag gac ctc agt tgg gag agt gct gcc gag cac              2069
Lys Arg Gly Met Met Gln Asp Leu Ser Trp Glu Ser Ala Ala Glu His
        665                 670                 675 tat gaa aaa gtc ctt gtt gct gcc aag tac caa tgg tgatgattga                   2115
Tyr Glu Lys Val Leu Val Ala Ala Lys Tyr Gln Trp
680                 685                 690 ttccatcttt ctcatagctt cccgttgatg catgcatgca tgcatcactt ggctctgctg            2175
gaagttgtgt gacaccataa aataataaca atctatcctc atcttgattt gttttttgtt            2235
tcccctaata actcaggtca tcttgaggca ataatgtaga agaagatatc tggatctttg            2295
ttgtgagttt taattccca tgccatggga atttataaaa aaaaaaaaaa aaa                    2348

<210> SEQ ID NO 6
<211> LENGTH: 690
<212> TYPE: PRT
<213> ORGANISM: Curcuma zedoaria

<400> SEQUENCE: 6

Met Phe Ser His Leu Leu Ser Ser Pro Pro Ala Pro Pro Pro Pro Gly
 1               5                   10                  15

Ala Ala Ser Cys Arg Leu Leu His Gly Gly Ala Arg Pro Leu Gly His
            20                  25                  30

Ser Pro Leu Cys Trp Ala Asn Pro Leu Cys Thr Ser Arg Phe Met Ala
        35                  40                  45

Gly Leu Ser Glu Val Lys Lys Gly Ser Lys Ile Thr Leu Lys His Ile
    50                  55                  60

Asp His Thr Gly Ser Ala Arg Thr Met Arg Phe Leu Asn Ala Leu Tyr
65                  70                  75                  80

His Gly Gln Ser Ala Asp Leu Val Pro Ile Asn His Arg Gly Lys Ser
                85                  90                  95

Ser Gly Ala Val Gly Arg Ser Asn Ile Asn Asp Ile Gln Glu Asp Ser
            100                 105                 110

Asn Gln Asp Val Asp Ile Ala Asp Ser Val Ala Gln Thr Met Glu
        115                 120                 125

Gln Ser Lys Lys Val Leu Glu Met Gln Arg Asn Leu Leu Gln Gln Ile
    130                 135                 140

Ile Glu Lys Arg Asn Phe Ser Glu Glu Thr Glu Ser Tyr Val Lys Lys
145                 150                 155                 160

Asp Glu Asn Leu Gly Ile Tyr Ala Glu Ala Tyr Met Gln Thr Ser Asn
                165                 170                 175
```

```
Asn Gln Gln Glu Ala Pro Pro Glu Glu Gly Asn Leu Asn Ser Pro Pro
        180                 185                 190
Leu Ala Gly Pro Asn Val Met Asn Ile Ile Leu Val Ala Ala Glu Cys
        195                 200                 205
Ala Pro Trp Ser Lys Thr Gly Gly Leu Gly Asp Val Val Gly Ala Leu
        210                 215                 220
Pro Lys Ala Leu Ala Lys Arg Gly His Arg Val Met Val Val Ser Pro
225                 230                 235                 240
Arg Tyr Gly Asn Tyr Pro Glu Pro Lys Glu Ile Gly Asn Leu Lys Arg
                245                 250                 255
Tyr Lys Val Asp Gly Gln Asp Met Glu Ile Lys Tyr Tyr His Thr Tyr
                260                 265                 270
Ile Asp Ser Val Asp Phe Val Phe Ile Asp Ser Pro Ile Phe Arg His
            275                 280                 285
Ile Gly Asn Asp Ile Tyr Gly Gly Asn Arg Val Asp Ile Leu Lys Arg
        290                 295                 300
Met Val Leu Phe Cys Lys Ala Val Glu Val Pro Trp His Val Pro
305                 310                 315                 320
Cys Gly Gly Phe Cys Tyr Gly Asp Gly Asn Leu Val Phe Ile Ala Asn
                325                 330                 335
Asp Trp His Thr Ser Leu Leu Pro Val Tyr Leu Lys Ala Cys Phe Arg
            340                 345                 350
Asp Arg Gly Leu Met Thr Tyr Ala Arg Cys Leu Leu Val Ile His Asn
        355                 360                 365
Ile Ala His Gln Gly Arg Gly Pro Leu Asp Asp Phe Ser Tyr Val Asp
    370                 375                 380
Leu Pro His Asp His Ile Asp Ser Phe Arg Leu Asp Asp Pro Val Gly
385                 390                 395                 400
Gly Glu His Phe Asn Ile Phe Ala Ala Gly Ile Arg Ala Ala Asp Arg
                405                 410                 415
Val Val Thr Val Ser His Gly Tyr Ala Trp Glu Leu Lys Thr Ser Glu
            420                 425                 430
Gly Gly Trp Gly Leu His Glu Ile Ile Asn Glu Cys His Trp Lys Phe
        435                 440                 445
His Gly Ile Val Asn Gly Ile Asp Thr His Ser Trp Asn Pro Lys Phe
    450                 455                 460
Asp Ala His Leu Asn Ser Asp Gly Tyr Thr Asn Phe Thr Leu Glu Thr
465                 470                 475                 480
Leu Glu Met Gly Lys Ala Gln Cys Lys Ala Ala Leu Gln Arg Glu Phe
                485                 490                 495
Gly Leu Pro Val Arg Asp Asp Val Pro Ile Leu Ala Phe Ile Gly Arg
            500                 505                 510
Leu Asp His Gln Lys Gly Ile Asp Leu Ile Ala Glu Ala Met His Trp
        515                 520                 525
Leu Val Gly Gln Asp Leu Gln Ile Ile Met Leu Gly Thr Gly Arg Pro
    530                 535                 540
Asp Leu Glu Asp Met Leu Arg Arg Phe Glu Arg Glu His Arg Gly Lys
545                 550                 555                 560
Val Arg Gly Trp Val Gly Phe Ser Val Lys Met Ala His Arg Ile Thr
                565                 570                 575
Ala Gly Ala Asp Ala Leu Leu Met Pro Ser Arg Phe Glu Pro Cys Gly
            580                 585                 590
```

```
Leu Asn Gln Leu His Ala Met Met Tyr Gly Thr Ile Pro Val Val His
            595                 600                 605

Ala Val Gly Gly Leu Arg Asp Thr Val Gln Gln Phe Asp Pro Phe Asn
610                 615                 620

Glu Thr Gly Leu Gly Trp Thr Phe Asp Arg Ala Glu Ala His Arg Met
625                 630                 635                 640

Ile Val Ala Leu Gly His Cys Leu Asn Thr Tyr Arg Asn Tyr Lys Glu
                645                 650                 655

Ser Trp Val Gly Leu Gln Lys Arg Gly Met Met Gln Asp Leu Ser Trp
            660                 665                 670

Glu Ser Ala Ala Glu His Tyr Glu Lys Val Leu Val Ala Ala Lys Tyr
            675                 680                 685

Gln Trp
    690

<210> SEQ ID NO 7
<211> LENGTH: 25
<212> TYPE: DNA
<213> ORGANISM: Curcuma zedoaria

<400> SEQUENCE: 7
atgttctccc acctcctatc ctctc                                        25

<210> SEQ ID NO 8
<211> LENGTH: 25
<212> TYPE: DNA
<213> ORGANISM: Curcuma zedoaria

<400> SEQUENCE: 8
tcaccattgg tacttggcag caaca                                        25

<210> SEQ ID NO 9
<211> LENGTH: 3434
<212> TYPE: DNA
<213> ORGANISM: Maranta arundinacea
<220> FEATURE:
<221> NAME/KEY: CDS
<222> LOCATION: (1315)...(2913)

<400> SEQUENCE: 9
tctcagcaaa aaaggcaaca actaaaaagg gcatctcgag agcagttgcc aaaaaatata    60
agcactcatt cacatagcaa cagtgatagt gaatctctgg aagctagttc tgctgggttc   120
tcaaacacag gccaaaattc tctatcaagc catgatgatg atggtgatat tattaggaag   180
acagatgtgg cagtatcatc tgatgaagaa agtaatagtg tgattgggag tgtagtcaga   240
ggggagcatc caagcattcg tcttgaggac ttgatagcta tggtcacaaa tgctgaaaaa   300
agtagttata tttgtgtttc catgtaaaac tgttacttct caatcttttt atctacctat   360
gatatgtttt tcagatactt tgcttcttaa tcaagctcgg gttcgtgcac ttgaagaact   420
tgacaaaata cttttagaaa aggtggcttt gcaatccgaa ataaacattc tagagatgaa   480
gttggcagaa acagatgcac gtattaaagc tgcagctcaa gaaaagatca atgtggaact   540
ccttgaagat cagatggagc agttgaagaa tgaaatgcct tcaaggaatt ctattgaagg   600
aggagggaat ggtgcatttt gtggtgaatt tcctcttgct ttggagcata atgccctgca   660
aagagaaaat tcaatgctaa aaagtgtatat acagactctt aagatgaaac taactgatgt   720
tagtgaaaca gaggaccgtg tgtcatcact agagaaagaa tgttctttgt tggatgattt   780
cctaaaagat ttgcaacgtc agtttgcaac ttttgatgtt ccaaacttg attccctgca   840
```

-continued

```
atatgaatgc agggctttgt cagacaaggt aatgcaatta ttatcaaata cagtgaacaa      900
tgggtttgat gtgcctcctg taagtttaca acaatataat gaactggaga agaaggttgc      960
taagttagag gcatctatga tggaagagaa ggtgccaaag ttcccctatg aaacatttca     1020
ccattatgaa cagattctac aacagaaaat tgagagcttg gaggagcgac tacaagtgtc     1080
tgatcaaaaa atgaattctg aaattcaatt gttccaggaa tcagttagac aatttcagga     1140
tacacttgat aagctatatg aagaaattga caaaaaatca cgtgaaactt gctggaaaa     1200 tgtaccttgt gaattttgga gtcgtttact gcttctaatt gatggttggt tgctcgagaa     1260
gaagatatca tctaatgatg ctaattcatt gagagaattg acgtggaaaa aggg atg       1317
                                                            Met
                                                            1
```

```
ctc gaa tcc atg atg cat att tgg cct cta aga aca aaa gtg agc ctg       1365
Leu Glu Ser Met Met His Ile Trp Pro Leu Arg Thr Lys Val Ser Leu
         5                  10                  15 aaa gat tgg cta cat ttc tca agg tta ctt cct tct cat gca agt gta       1413
Lys Asp Trp Leu His Phe Ser Arg Leu Leu Pro Ser His Ala Ser Val
     20                  25                  30 gga ttg cac ata tcc cat att gcc gca gaa atg gct cca att gca aag       1461
Gly Leu His Ile Ser His Ile Ala Ala Glu Met Ala Pro Ile Ala Lys
 35                  40                  45 gtt ggc ggt tta gga gat gtt gta tct ggt ctt tgc aaa gcg ttg cag       1509
Val Gly Gly Leu Gly Asp Val Val Ser Gly Leu Cys Lys Ala Leu Gln
 50                  55                  60                  65 agg aag gga cac ttg gtg gaa att gtc ctt cca aaa tat gat tgt atg       1557
Arg Lys Gly His Leu Val Glu Ile Val Leu Pro Lys Tyr Asp Cys Met
             70                  75                  80 cag tat gat ctt gtt cct gat ctg agg gta ttg gat gtt gca gta gag       1605
Gln Tyr Asp Leu Val Pro Asp Leu Arg Val Leu Asp Val Ala Val Glu
         85                  90                  95 tct tat ttt gat gga caa tta ttc aag aat aaa att tgg gtt gcg gct       1653
Ser Tyr Phe Asp Gly Gln Leu Phe Lys Asn Lys Ile Trp Val Ala Ala
         100                 105                 110 gta gaa ggt ctt cct gtt tac ttt ata gag cct cat cat cca gac aag       1701
Val Glu Gly Leu Pro Val Tyr Phe Ile Glu Pro His His Pro Asp Lys
 115                 120                 125 ctc ttc tgg aga gga aaa tac tat gga gaa cat gat gac ttc aaa cgc       1749
Leu Phe Trp Arg Gly Lys Tyr Tyr Gly Glu His Asp Asp Phe Lys Arg
130                 135                 140                 145 ttt tca ttt ttt agc cgt gct gct ctt gaa tta ctc tat caa gct ggg       1797
Phe Ser Phe Phe Ser Arg Ala Ala Leu Glu Leu Leu Tyr Gln Ala Gly
                150                 155                 160 aag aaa cct gac ata att cat tgt cat gat tgg cag aca gcc ttt gtt       1845
Lys Lys Pro Asp Ile Ile His Cys His Asp Trp Gln Thr Ala Phe Val
             165                 170                 175 gca cca ctt tac tgg gat ata tat gct aac aaa ggc tta aat tca gct       1893
Ala Pro Leu Tyr Trp Asp Ile Tyr Ala Asn Lys Gly Leu Asn Ser Ala
         180                 185                 190 aga att tgc ttt acc tgc cac aac ttt gag cat cag gga att ata cct       1941
Arg Ile Cys Phe Thr Cys His Asn Phe Glu His Gln Gly Ile Ile Pro
     195                 200                 205 gct tca gcc ttg gca tcc tgt ggt ttt gat gtc cat cat atg aac aga       1989
Ala Ser Ala Leu Ala Ser Cys Gly Phe Asp Val His His Met Asn Arg
210                 215                 220                 225 gat cga atg cag gac aat tca gcg cat gac aga gtc aat gtt gtt aag       2037
Asp Arg Met Gln Asp Asn Ser Ala His Asp Arg Val Asn Val Val Lys
                230                 235                 240
```

```
ggt gca att gtg ttc tct aac att gtt act acc gta tca cca act tat    2085
Gly Ala Ile Val Phe Ser Asn Ile Val Thr Thr Val Ser Pro Thr Tyr
            245                 250                 255 gct caa gag gcg tgc act gca gag ggt ggt cgg ggc cta cac gaa aca    2133
Ala Gln Glu Ala Cys Thr Ala Glu Gly Gly Arg Gly Leu His Glu Thr
        260                 265                 270 tta cag tca ttt tcg aag aaa ttt gtg ggg att ctt aat ggc att gat    2181
Leu Gln Ser Phe Ser Lys Lys Phe Val Gly Ile Leu Asn Gly Ile Asp
    275                 280                 285 gct gat gca tgg aat cct tca act gat aaa tat atc agt gtt cag tat    2229
Ala Asp Ala Trp Asn Pro Ser Thr Asp Lys Tyr Ile Ser Val Gln Tyr
290                 295                 300                 305 agt gct gat gat ctt cag gga aaa gcc gag aac aaa gat gct ata agg    2277
Ser Ala Asp Asp Leu Gln Gly Lys Ala Glu Asn Lys Asp Ala Ile Arg
                310                 315                 320 aag cat ctt aaa ctt tcc ttg tca gag ggt tct cga cca ctg gtt gct    2325
Lys His Leu Lys Leu Ser Leu Ser Glu Gly Ser Arg Pro Leu Val Ala
            325                 330                 335 tgt att gca cgg ctc gtg cca cag aaa ggt gtg cat ctt atc agg cat    2373
Cys Ile Ala Arg Leu Val Pro Gln Lys Gly Val His Leu Ile Arg His
        340                 345                 350 gca ata tat cgt aca ctg gag tta ggt gga caa ttt gtg ctt ctt ggt    2421
Ala Ile Tyr Arg Thr Leu Glu Leu Gly Gly Gln Phe Val Leu Leu Gly
    355                 360                 365 gaa agt cca gtc cca cac att cag cgg gag ttt gag gat att gca aag    2469
Glu Ser Pro Val Pro His Ile Gln Arg Glu Phe Glu Asp Ile Ala Lys
370                 375                 380                 385 cat ttc cag agc cac cct cat gtc cgg ttg ctc ttg aaa tac gac gaa    2517
His Phe Gln Ser His Pro His Val Arg Leu Leu Leu Lys Tyr Asp Glu
                390                 395                 400 gcc ctt tca cgc tta att tat gca gca tct gac atg ttt atc att cca    2565
Ala Leu Ser Arg Leu Ile Tyr Ala Ala Ser Asp Met Phe Ile Ile Pro
            405                 410                 415 tca atg ttc gag cct tgt ggt ctt acc cag atg att gct atg aga tat    2613
Ser Met Phe Glu Pro Cys Gly Leu Thr Gln Met Ile Ala Met Arg Tyr
        420                 425                 430 ggt tct gtg cca att gca aga aaa acc ggt ggg ctc aac gat agt gtc    2661
Gly Ser Val Pro Ile Ala Arg Lys Thr Gly Gly Leu Asn Asp Ser Val
    435                 440                 445 ttt gat att gat gat aat atg ata cca gaa caa tac cag aat gga ttt    2709
Phe Asp Ile Asp Asp Asn Met Ile Pro Glu Gln Tyr Gln Asn Gly Phe
450                 455                 460                 465 acg ttt ctg aca acc gat gaa cag ggt cta agc agt gca atg gaa cga    2757
Thr Phe Leu Thr Thr Asp Glu Gln Gly Leu Ser Ser Ala Met Glu Arg
                470                 475                 480 gca ttt cgg tac tac act aaa agc cct aag aac tgg caa aat ctt gtt    2805
Ala Phe Arg Tyr Tyr Thr Lys Ser Pro Lys Asn Trp Gln Asn Leu Val
            485                 490                 495 cag aag gtt atg aga atg gac ttc agt tgg gat tct tcg gca tcg caa    2853
Gln Lys Val Met Arg Met Asp Phe Ser Trp Asp Ser Ser Ala Ser Gln
        500                 505                 510 tat gaa gaa cta tat caa aaa tcc gtg gct aga gca agg gca gca gca    2901
Tyr Glu Glu Leu Tyr Gln Lys Ser Val Ala Arg Ala Arg Ala Ala Ala
    515                 520                 525 gcc gct cga gtg taaattcctg ttaaatcccc cctataccgt tccatatcca        2953
Ala Ala Arg Val
530 gggccaaggc ctctctatac acattataaa gtccattttg ctgctgaagc ataaatcatg  3013 ggatacactg cagcgctcat atttttatt cctctgccca ccaaaatggt acaccgagtg   3073
```

-continued

```
gcaatcatca gtgattgatt aatgatccaa ttcaattgct gccaactgaa ataatcaagt    3133
tgttggatat caactccacc tcgaagaaca gcggaaagct caatgcacat aatacctggt    3193
tccggatatt tgtgaagaag caacaaaagc atgcgcctta tcagcaaatg gcatttatga    3253
tgcttactcc aagtgccaac aattttaggc aatccacttg ttcatgcatt tccacgagat    3313
gctgttgctg tttacatttg ttttacatgc agtcatcagt acagatatat cccaacagag    3373
tttgactgtt ataagtaatg cgcttattac ttaacgtgct actaaaaaaa aaaaaaaaa     3433 a                                                                    3434
```

<210> SEQ ID NO 10
<211> LENGTH: 533
<212> TYPE: PRT
<213> ORGANISM: Maranta arundinacea

<400> SEQUENCE: 10

```
Met Leu Glu Ser Met Met His Ile Trp Pro Leu Arg Thr Lys Val Ser
  1               5                  10                  15

Leu Lys Asp Trp Leu His Phe Ser Arg Leu Leu Pro Ser His Ala Ser
             20                  25                  30

Val Gly Leu His Ile Ser His Ile Ala Ala Glu Met Ala Pro Ile Ala
         35                  40                  45

Lys Val Gly Gly Leu Gly Asp Val Val Ser Gly Leu Cys Lys Ala Leu
     50                  55                  60

Gln Arg Lys Gly His Leu Val Glu Ile Val Leu Pro Lys Tyr Asp Cys
 65                  70                  75                  80

Met Gln Tyr Asp Leu Val Pro Asp Leu Arg Val Leu Asp Val Ala Val
                 85                  90                  95

Glu Ser Tyr Phe Asp Gly Gln Leu Phe Lys Asn Lys Ile Trp Val Ala
            100                 105                 110

Ala Val Glu Gly Leu Pro Val Tyr Phe Ile Glu Pro His His Pro Asp
        115                 120                 125

Lys Leu Phe Trp Arg Gly Lys Tyr Tyr Gly Glu His Asp Asp Phe Lys
    130                 135                 140

Arg Phe Ser Phe Phe Ser Arg Ala Ala Leu Glu Leu Leu Tyr Gln Ala
145                 150                 155                 160

Gly Lys Lys Pro Asp Ile Ile His Cys His Asp Trp Gln Thr Ala Phe
                165                 170                 175

Val Ala Pro Leu Tyr Trp Asp Ile Tyr Ala Asn Lys Gly Leu Asn Ser
            180                 185                 190

Ala Arg Ile Cys Phe Thr Cys His Asn Phe Glu His Gln Gly Ile Ile
        195                 200                 205

Pro Ala Ser Ala Leu Ala Ser Cys Gly Phe Asp Val His His Met Asn
    210                 215                 220

Arg Asp Arg Met Gln Asp Asn Ser Ala His Asp Arg Val Asn Val Val
225                 230                 235                 240

Lys Gly Ala Ile Val Phe Ser Asn Ile Val Thr Thr Val Ser Pro Thr
                245                 250                 255

Tyr Ala Gln Glu Ala Cys Thr Ala Glu Gly Gly Arg Gly Leu His Glu
            260                 265                 270

Thr Leu Gln Ser Phe Ser Lys Lys Phe Val Gly Ile Leu Asn Gly Ile
        275                 280                 285

Asp Ala Asp Ala Trp Asn Pro Ser Thr Asp Lys Tyr Ile Ser Val Gln
    290                 295                 300
```

-continued

```
Tyr Ser Ala Asp Asp Leu Gln Gly Lys Ala Glu Asn Lys Asp Ala Ile
305                 310                 315                 320

Arg Lys His Leu Lys Leu Ser Leu Ser Glu Gly Ser Arg Pro Leu Val
            325                 330                 335

Ala Cys Ile Ala Arg Leu Val Pro Gln Lys Gly Val His Leu Ile Arg
            340                 345                 350

His Ala Ile Tyr Arg Thr Leu Glu Leu Gly Gly Gln Phe Val Leu Leu
            355                 360                 365

Gly Glu Ser Pro Val Pro His Ile Gln Arg Glu Phe Glu Asp Ile Ala
        370                 375                 380

Lys His Phe Gln Ser His Pro His Val Arg Leu Leu Leu Lys Tyr Asp
385                 390                 395                 400

Glu Ala Leu Ser Arg Leu Ile Tyr Ala Ala Ser Asp Met Phe Ile Ile
                405                 410                 415

Pro Ser Met Phe Glu Pro Cys Gly Leu Thr Gln Met Ile Ala Met Arg
            420                 425                 430

Tyr Gly Ser Val Pro Ile Ala Arg Lys Thr Gly Gly Leu Asn Asp Ser
            435                 440                 445

Val Phe Asp Ile Asp Asp Asn Met Ile Pro Glu Gln Tyr Gln Asn Gly
        450                 455                 460

Phe Thr Phe Leu Thr Thr Asp Glu Gln Gly Leu Ser Ser Ala Met Glu
465                 470                 475                 480

Arg Ala Phe Arg Tyr Tyr Thr Lys Ser Pro Lys Asn Trp Gln Asn Leu
                485                 490                 495

Val Gln Lys Val Met Arg Met Asp Phe Ser Trp Asp Ser Ser Ala Ser
            500                 505                 510

Gln Tyr Glu Glu Leu Tyr Gln Lys Ser Val Ala Arg Ala Arg Ala Ala
            515                 520                 525

Ala Ala Ala Arg Val
        530

<210> SEQ ID NO 11
<211> LENGTH: 25
<212> TYPE: DNA
<213> ORGANISM: Maranta arundinacea

<400> SEQUENCE: 11
atgctcgaat ccatgatgca tattt                                           25

<210> SEQ ID NO 12
<211> LENGTH: 25
<212> TYPE: DNA
<213> ORGANISM: Maranta arundinacea

<400> SEQUENCE: 12
ttacactcga gcggctgctg ctgcc                                           25

<210> SEQ ID NO 13
<211> LENGTH: 2176
<212> TYPE: DNA
<213> ORGANISM: Canna edulis
<220> FEATURE:
<221> NAME/KEY: CDS
<222> LOCATION: (81)...(1928)

<400> SEQUENCE: 13
gaagctcctc acttgtcgct gcgagcaaga gcaagtcctt caatctgagt gagagtggtg     60
```

-continued

```
aatgacgtga gcatattcca atg gct gct atg acg gca tca cac ttc atc tca    113
                     Met Ala Ala Met Thr Ala Ser His Phe Ile Ser
                      1               5                  10 aat agt tca tgc tcc atc ttc aat gga gct ttt gat tct gtg gtg acg      161
Asn Ser Ser Cys Ser Ile Phe Asn Gly Ala Phe Asp Ser Val Val Thr
            15                  20                  25 tct ttc caa agc aga agg att cca ttc tcc agc aac cac act aat aat      209
Ser Phe Gln Ser Arg Arg Ile Pro Phe Ser Ser Asn His Thr Asn Asn
        30                  35                  40 tat gaa ggg ctg aga act cgg aat gtg gtg gat tca cgt aaa acg cgg      257
Tyr Glu Gly Leu Arg Thr Arg Asn Val Val Asp Ser Arg Lys Thr Arg
    45                  50                  55 atg act gcg aag gca act tct agg cta gct agg agg gtt act cga cat      305
Met Thr Ala Lys Ala Thr Ser Arg Leu Ala Arg Arg Val Thr Arg His
 60                  65                  70                  75 gcc agc caa aga ccc ttg att gtt gct gtc tgt gga act gga atg aac      353
Ala Ser Gln Arg Pro Leu Ile Val Ala Val Cys Gly Thr Gly Met Asn
                 80                  85                  90 ttg gtg ttt gtt ggt tgt gag gta gct cca tgg agc aaa act ggg ggc      401
Leu Val Phe Val Gly Cys Glu Val Ala Pro Trp Ser Lys Thr Gly Gly
             95                 100                 105 ctt ggc gat gtt ctt aga gga ttg cca cct gct atg gct gca att ggg      449
Leu Gly Asp Val Leu Arg Gly Leu Pro Pro Ala Met Ala Ala Ile Gly
        110                 115                 120 cac agg gtc atg acc gtg gtg cca cga tat gac caa tat aaa gat atc      497
His Arg Val Met Thr Val Val Pro Arg Tyr Asp Gln Tyr Lys Asp Ile
    125                 130                 135 tgg gat aca agt gtc cca gtt gag tta aaa gtt ggg gat aag att gaa      545
Trp Asp Thr Ser Val Pro Val Glu Leu Lys Val Gly Asp Lys Ile Glu
140                 145                 150                 155 act gtc cgc ttc ttc cac tgc tac aaa agg gga gtt gat cgg gtt ttt      593
Thr Val Arg Phe Phe His Cys Tyr Lys Arg Gly Val Asp Arg Val Phe
                160                 165                 170 gtg gat cac cct atg ttt ctc gag aag gtt tgg ggg aaa aca gga gga      641
Val Asp His Pro Met Phe Leu Glu Lys Val Trp Gly Lys Thr Gly Gly
            175                 180                 185 aaa tta tat ggt cct gtt aca gga aca gat tat gca gac aat caa cta      689
Lys Leu Tyr Gly Pro Val Thr Gly Thr Asp Tyr Ala Asp Asn Gln Leu
        190                 195                 200 aga ttc agc ctt ttg tgc ctg gca gct ctg gaa gct cca aga ctt cta      737
Arg Phe Ser Leu Leu Cys Leu Ala Ala Leu Glu Ala Pro Arg Leu Leu
    205                 210                 215 aat ctc aac aac agc aaa tac tat tct gga cca tat gga gat gat gtt      785
Asn Leu Asn Asn Ser Lys Tyr Tyr Ser Gly Pro Tyr Gly Asp Asp Val
220                 225                 230                 235 gtg ttt att gcc aac gat tgg cat tct gct cta ctg ccc tgc tac ttg      833
Val Phe Ile Ala Asn Asp Trp His Ser Ala Leu Leu Pro Cys Tyr Leu
                240                 245                 250 aaa act atg tac caa tca cat ggt att tac atg aat gct aag gtt gca      881
Lys Thr Met Tyr Gln Ser His Gly Ile Tyr Met Asn Ala Lys Val Ala
            255                 260                 265 ttt tgc att cat aat att gct tac cag ggc cga ttt gcc ttt tcg gac      929
Phe Cys Ile His Asn Ile Ala Tyr Gln Gly Arg Phe Ala Phe Ser Asp
        270                 275                 280 ttt gaa ctc ctt aat ctc ccc aat aaa ttt aaa tct tca ttt gat ttc      977
Phe Glu Leu Leu Asn Leu Pro Asn Lys Phe Lys Ser Ser Phe Asp Phe
    285                 290                 295 atg gat gga tat gac aaa cct gtg aaa gga agg aaa ata aat tgg atg    1025
Met Asp Gly Tyr Asp Lys Pro Val Lys Gly Arg Lys Ile Asn Trp Met
300                 305                 310                 315
```

```
aag gct gga ata ata gaa tgt gat agg tgc ttg acc gtg agc cca tat      1073
Lys Ala Gly Ile Ile Glu Cys Asp Arg Cys Leu Thr Val Ser Pro Tyr
                320                 325                 330 tat gcc caa gag ctt gtc tca ggg gta gag aag ggt gtt gag ttg ggc      1121
Tyr Ala Gln Glu Leu Val Ser Gly Val Glu Lys Gly Val Glu Leu Gly
            335                 340                 345 aat atc ctg cgc atg aaa acc atc tgt gga ata gta aat ggg atg gac      1169
Asn Ile Leu Arg Met Lys Thr Ile Cys Gly Ile Val Asn Gly Met Asp
        350                 355                 360 acc acg gag tgg aat cca tta aca gac aaa tat att tct aca aac tac      1217
Thr Thr Glu Trp Asn Pro Leu Thr Asp Lys Tyr Ile Ser Thr Asn Tyr
    365                 370                 375 gat gca aca act gta ttg gat gca aaa cct ctc tgt aag gaa gct ttg      1265
Asp Ala Thr Thr Val Leu Asp Ala Lys Pro Leu Cys Lys Glu Ala Leu
380                 385                 390                 395 caa gct gag tgt ggg ctg cct gtt aac aaa aac aag ctt gtt ttg gcc      1313
Gln Ala Glu Cys Gly Leu Pro Val Asn Lys Asn Lys Leu Val Leu Ala
                400                 405                 410 ttt gtt gga aga cta gat gag cag aaa ggc tca gac att cta gct gca      1361
Phe Val Gly Arg Leu Asp Glu Gln Lys Gly Ser Asp Ile Leu Ala Ala
            415                 420                 425 gca att cca gaa ctt ctt tgt gag aat gtt caa gtg ata gta ctt ggc      1409
Ala Ile Pro Glu Leu Leu Cys Glu Asn Val Gln Val Ile Val Leu Gly
        430                 435                 440 act ggc aag aag aag ttg gag agt gaa ctt aca tta ctt gag gaa atg      1457
Thr Gly Lys Lys Lys Leu Glu Ser Glu Leu Thr Leu Leu Glu Glu Met
    445                 450                 455 ttt cca gac aaa ttc aga gca cat ctc aaa ttc aac gtt cct tta gct      1505
Phe Pro Asp Lys Phe Arg Ala His Leu Lys Phe Asn Val Pro Leu Ala
460                 465                 470                 475 cat gca atc atg gca gga gct gat atc ctt gtt att cca agc aga ttc      1553
His Ala Ile Met Ala Gly Ala Asp Ile Leu Val Ile Pro Ser Arg Phe
                480                 485                 490 gaa ccc tgt ggc ctc att cag ctt cag gcc atg cga tat gga act ctc      1601
Glu Pro Cys Gly Leu Ile Gln Leu Gln Ala Met Arg Tyr Gly Thr Leu
            495                 500                 505 cct atg tgt agc acc act ggt gga ctt gtt gac act gtc aaa gaa ggc      1649
Pro Met Cys Ser Thr Thr Gly Gly Leu Val Asp Thr Val Lys Glu Gly
        510                 515                 520 ttc act ggc ttc cat atg ggc ccc ttc agt gtg gag tgt gat gcc gta      1697
Phe Thr Gly Phe His Met Gly Pro Phe Ser Val Glu Cys Asp Ala Val
    525                 530                 535 gac aaa gct gat gta caa aag att gtc gaa acc acg aaa agg gcc ctc      1745
Asp Lys Ala Asp Val Gln Lys Ile Val Glu Thr Thr Lys Arg Ala Leu
540                 545                 550                 555 aaa gtc tat gga aca cct gct ttt gtg gag atg atc aag aac tgc atg      1793
Lys Val Tyr Gly Thr Pro Ala Phe Val Glu Met Ile Lys Asn Cys Met
                560                 565                 570 aac caa gat ctc tca tgg aag gga cct gca aag aag tgg gaa caa ttt      1841
Asn Gln Asp Leu Ser Trp Lys Gly Pro Ala Lys Lys Trp Glu Gln Phe
            575                 580                 585 ctc ctg agc atg ggg gct gct ggc agt gaa cct gga att gat ggg gag      1889
Leu Leu Ser Met Gly Ala Ala Gly Ser Glu Pro Gly Ile Asp Gly Glu
        590                 595                 600 gaa ata gct cct ctt gcc aag gaa aat gta gct act cca tgagagatga      1938
Glu Ile Ala Pro Leu Ala Lys Glu Asn Val Ala Thr Pro
    605                 610                 615 ctaatacttt cctctttagt catagtccta agccttgttg taaagataaa taatcatcct   1998
```

```
ccaaaacctc catcgacatg atgtatcctt cacgagcttg gataaattcc aagagttttt    2058
atataagcag ttatgtagtc gtcaatctgt atggaaaatc cgtcaatgaa atttttttat    2118
tgatggctat taatcttagg ccagtatttg atgtttgtgt aaaaaaaaaa aaaaaaa       2176
```

<210> SEQ ID NO 14
<211> LENGTH: 616
<212> TYPE: PRT
<213> ORGANISM: Canna edulis

<400> SEQUENCE: 14

```
Met Ala Ala Met Thr Ala Ser His Phe Ile Ser Asn Ser Ser Cys Ser
 1               5                  10                  15

Ile Phe Asn Gly Ala Phe Asp Ser Val Val Thr Ser Phe Gln Ser Arg
            20                  25                  30

Arg Ile Pro Phe Ser Ser Asn His Thr Asn Asn Tyr Glu Gly Leu Arg
        35                  40                  45

Thr Arg Asn Val Val Asp Ser Arg Lys Thr Arg Met Thr Ala Lys Ala
    50                  55                  60

Thr Ser Arg Leu Ala Arg Arg Val Thr Arg His Ala Ser Gln Arg Pro
65                  70                  75                  80

Leu Ile Val Ala Val Cys Gly Thr Gly Met Asn Leu Val Phe Val Gly
                85                  90                  95

Cys Glu Val Ala Pro Trp Ser Lys Thr Gly Gly Leu Gly Asp Val Leu
            100                 105                 110

Arg Gly Leu Pro Pro Ala Met Ala Ala Ile Gly His Arg Val Met Thr
        115                 120                 125

Val Val Pro Arg Tyr Asp Gln Tyr Lys Asp Ile Trp Asp Thr Ser Val
    130                 135                 140

Pro Val Glu Leu Lys Val Gly Asp Lys Ile Glu Thr Val Arg Phe Phe
145                 150                 155                 160

His Cys Tyr Lys Arg Gly Val Asp Arg Val Phe Val Asp His Pro Met
                165                 170                 175

Phe Leu Glu Lys Val Trp Gly Lys Thr Gly Gly Lys Leu Tyr Gly Pro
            180                 185                 190

Val Thr Gly Thr Asp Tyr Ala Asp Asn Gln Leu Arg Phe Ser Leu Leu
        195                 200                 205

Cys Leu Ala Ala Leu Glu Ala Pro Arg Leu Leu Asn Leu Asn Asn Ser
    210                 215                 220

Lys Tyr Tyr Ser Gly Pro Tyr Gly Asp Asp Val Val Phe Ile Ala Asn
225                 230                 235                 240

Asp Trp His Ser Ala Leu Leu Pro Cys Tyr Leu Lys Thr Met Tyr Gln
                245                 250                 255

Ser His Gly Ile Tyr Met Asn Ala Lys Val Ala Phe Cys Ile His Asn
            260                 265                 270

Ile Ala Tyr Gln Gly Arg Phe Ala Phe Ser Asp Phe Glu Leu Leu Asn
        275                 280                 285

Leu Pro Asn Lys Phe Lys Ser Ser Phe Asp Phe Met Asp Gly Tyr Asp
    290                 295                 300

Lys Pro Val Lys Gly Arg Lys Ile Asn Trp Met Lys Ala Gly Ile Ile
305                 310                 315                 320

Glu Cys Asp Arg Cys Leu Thr Val Ser Pro Tyr Tyr Ala Gln Glu Leu
                325                 330                 335

Val Ser Gly Val Glu Lys Gly Val Glu Leu Gly Asn Ile Leu Arg Met
            340                 345                 350
```

```
Lys Thr Ile Cys Gly Ile Val Asn Gly Met Asp Thr Thr Glu Trp Asn
            355                 360                 365

Pro Leu Thr Asp Lys Tyr Ile Ser Thr Asn Tyr Asp Ala Thr Thr Val
    370                 375                 380

Leu Asp Ala Lys Pro Leu Cys Lys Glu Ala Leu Gln Ala Glu Cys Gly
385                 390                 395                 400

Leu Pro Val Asn Lys Asn Lys Leu Val Leu Ala Phe Val Gly Arg Leu
                405                 410                 415

Asp Glu Gln Lys Gly Ser Asp Ile Leu Ala Ala Ile Pro Glu Leu
            420                 425                 430

Leu Cys Glu Asn Val Gln Val Ile Val Leu Gly Thr Gly Lys Lys Lys
            435                 440                 445

Leu Glu Ser Glu Leu Thr Leu Leu Glu Glu Met Phe Pro Asp Lys Phe
    450                 455                 460

Arg Ala His Leu Lys Phe Asn Val Pro Leu Ala His Ala Ile Met Ala
465                 470                 475                 480

Gly Ala Asp Ile Leu Val Ile Pro Ser Arg Phe Glu Pro Cys Gly Leu
                485                 490                 495

Ile Gln Leu Gln Ala Met Arg Tyr Gly Thr Leu Pro Met Cys Ser Thr
            500                 505                 510

Thr Gly Gly Leu Val Asp Thr Val Lys Glu Gly Phe Thr Gly Phe His
            515                 520                 525

Met Gly Pro Phe Ser Val Glu Cys Asp Ala Val Asp Lys Ala Asp Val
            530                 535                 540

Gln Lys Ile Val Glu Thr Thr Lys Arg Ala Leu Lys Val Tyr Gly Thr
545                 550                 555                 560

Pro Ala Phe Val Glu Met Ile Lys Asn Cys Met Asn Gln Asp Leu Ser
                565                 570                 575

Trp Lys Gly Pro Ala Lys Lys Trp Glu Gln Phe Leu Leu Ser Met Gly
            580                 585                 590

Ala Ala Gly Ser Glu Pro Gly Ile Asp Gly Glu Glu Ile Ala Pro Leu
            595                 600                 605

Ala Lys Glu Asn Val Ala Thr Pro
    610                 615

<210> SEQ ID NO 15
<211> LENGTH: 25
<212> TYPE: DNA
<213> ORGANISM: Canna edulis

<400> SEQUENCE: 15
atggctgcta tgacggcatc acact                                              25

<210> SEQ ID NO 16
<211> LENGTH: 25
<212> TYPE: DNA
<213> ORGANISM: Canna edulis

<400> SEQUENCE: 16
tcatggagta gctacatttt ccttg                                              25

<210> SEQ ID NO 17
<211> LENGTH: 2274
<212> TYPE: DNA
<213> ORGANISM: Typha latifolia
<220> FEATURE:
<221> NAME/KEY: CDS
```

-continued

<222> LOCATION: (115)...(1956)

<400> SEQUENCE: 17

| | |
|---|---:|
| tgagatagtg aggaagagag tgagagagct cacagtagtt tgagcaaact cctaagcttt | 60 |

| | | |
|---|---|---:|
| tctctaatcc ttctatctga gagaaaagaa agaacagaa agtgagcact tcca atg<br>                                                                                                                                                                                                                                      Met<br>                                                                                                                                                                                                                                               1 | 117 |

| | |
|---|---:|
| gct act gtg act gca tca cag ttt gta cca aag tgc ttg tat ggc agt<br>Ala Thr Val Thr Ala Ser Gln Phe Val Pro Lys Cys Leu Tyr Gly Ser<br>             5                          10                     15 | 165 |
| gca gcc gat tcc aac cca aga gca ttc cac aac agg aag att gca gat<br>Ala Ala Asp Ser Asn Pro Arg Ala Phe His Asn Arg Lys Ile Ala Asp<br>          20                       25                     30 | 213 |
| ttg aag aac caa gcc act gct tat cat gga ctc aga tct caa aac tca<br>Leu Lys Asn Gln Ala Thr Ala Tyr His Gly Leu Arg Ser Gln Asn Ser<br>35                   40                       45 | 261 |
| gta gac ttg ctt cag gtt agg act aaa gct aaa aca act tcc aag caa<br>Val Asp Leu Leu Gln Val Arg Thr Lys Ala Lys Thr Thr Ser Lys Gln<br>50                   55                     60                       65 | 309 |
| ttt aag aat ggt tgt tct act gtg aat ctg aga cct cca cga gcc gtg<br>Phe Lys Asn Gly Cys Ser Thr Val Asn Leu Arg Pro Pro Arg Ala Val<br>                   70                       75                     80 | 357 |
| gtc ata tgt gga aaa ggg atg aac tta gtc ttt gtt gga gct gag atg<br>Val Ile Cys Gly Lys Gly Met Asn Leu Val Phe Val Gly Ala Glu Met<br>                     85                     90                       95 | 405 |
| gct cca tgg agc aag act gga ggc ctt ggt gat gtt ctt gga gga ctc<br>Ala Pro Trp Ser Lys Thr Gly Gly Leu Gly Asp Val Leu Gly Gly Leu<br>          100                     105                    110 | 453 |
| cca ccg gca ttg gcg gca aat gga cat cga gtt atg gtt ata gcg cca<br>Pro Pro Ala Leu Ala Ala Asn Gly His Arg Val Met Val Ile Ala Pro<br>115                  120                     125 | 501 |
| cgt tat gat caa tac atg gat gct tgg gat aca gat gct ctt gtt gag<br>Arg Tyr Asp Gln Tyr Met Asp Ala Trp Asp Thr Asp Ala Leu Val Glu<br>130                 135                   140               145 | 549 |
| ttg aaa gtt ggg gat agg tgt gaa acc gtg cgc ttc ttt cac tgc tat<br>Leu Lys Val Gly Asp Arg Cys Glu Thr Val Arg Phe Phe His Cys Tyr<br>                   150                     155                   160 | 597 |
| aaa aga gga gtt gat cga gtt ttt gtc gat cac cct atg ttt ctt gcg<br>Lys Arg Gly Val Asp Arg Val Phe Val Asp His Pro Met Phe Leu Ala<br>                   165                     170                   175 | 645 |
| aag gtc tgg ggg aaa act ggt ggg aag att tat ggt cct aac act gga<br>Lys Val Trp Gly Lys Thr Gly Gly Lys Ile Tyr Gly Pro Asn Thr Gly<br>180                  185                     190 | 693 |
| aca gac tat cag gac aat cag cta cgc ttc agc ttt cta tgc cag gca<br>Thr Asp Tyr Gln Asp Asn Gln Leu Arg Phe Ser Phe Leu Cys Gln Ala<br>195                  200                     205 | 741 |
| gca ttg gaa gct cct aga att cta aat ctc aac aac agt gat tct ttc<br>Ala Leu Glu Ala Pro Arg Ile Leu Asn Leu Asn Asn Ser Asp Ser Phe<br>210                  215                     220                     225 | 789 |
| tct ggt cct tat ggg gaa gat gtt atc ttc att tgc aat gat tgg cac<br>Ser Gly Pro Tyr Gly Glu Asp Val Ile Phe Ile Cys Asn Asp Trp His<br>                   230                     235                   240 | 837 |
| act tct ctt ctg cca tgc tac tta aag agc atg tac cat ccc cgt ggc<br>Thr Ser Leu Leu Pro Cys Tyr Leu Lys Ser Met Tyr His Pro Arg Gly<br>                   245                     250                   255 | 885 |
| att tac aag aac gcc aag gtt gct ttc tgc att cac aat ata tca tac<br>Ile Tyr Lys Asn Ala Lys Val Ala Phe Cys Ile His Asn Ile Ser Tyr<br>          260                     265                    270 | 933 |
| caa ggt cga ttt tct ccc tca gac ttc gaa ttt ctc aat ctt ccg gag | 981 |

```
Gln Gly Arg Phe Ser Pro Ser Asp Phe Glu Phe Leu Asn Leu Pro Glu
    275                 280                 285 aat ttc aaa tct tct ttc agt ttc att gat ggg tac aac aag cct gtg      1029
Asn Phe Lys Ser Ser Phe Ser Phe Ile Asp Gly Tyr Asn Lys Pro Val
290                 295                 300                 305 aag gga atg aag ata aat tgg atg aag gca gga atc tta gaa tca gac      1077
Lys Gly Met Lys Ile Asn Trp Met Lys Ala Gly Ile Leu Glu Ser Asp
                310                 315                 320 agg gtg ttt aca gtg agt cca tat tat gca caa gag ctc ctt tca gga      1125
Arg Val Phe Thr Val Ser Pro Tyr Tyr Ala Gln Glu Leu Leu Ser Gly
            325                 330                 335 gaa gaa agg gga gtc gag ttg gac aac att ttg cgt gtg acc agt atc      1173
Glu Glu Arg Gly Val Glu Leu Asp Asn Ile Leu Arg Val Thr Ser Ile
        340                 345                 350 aca gga att gtg aat gga atg gat gtt aat gag tgg aat cca tta aca      1221
Thr Gly Ile Val Asn Gly Met Asp Val Asn Glu Trp Asn Pro Leu Thr
    355                 360                 365 gac aag tat att tct gtt aat tat gat gca aaa cct gta atg gaa gca      1269
Asp Lys Tyr Ile Ser Val Asn Tyr Asp Ala Lys Pro Val Met Glu Ala
370                 375                 380                 385 aag cct ctt aac aag gaa gca ttg caa gct gaa agt tgg ctt gcc tgt      1317
Lys Pro Leu Asn Lys Glu Ala Leu Gln Ala Glu Ser Trp Leu Ala Cys
                390                 395                 400 aga cag gga cat ccc tgt aat tgt att cat gga aga cta gag gag cag      1365
Arg Gln Gly His Pro Cys Asn Cys Ile His Gly Arg Leu Glu Glu Gln
            405                 410                 415 aaa gga tca gat att cta gca gca tcc att cca gag atc atg gat gag      1413
Lys Gly Ser Asp Ile Leu Ala Ala Ser Ile Pro Glu Ile Met Asp Glu
        420                 425                 430 aat gtt cag cta att att ctt gga act ggc aag aag gaa atg gag aat      1461
Asn Val Gln Leu Ile Ile Leu Gly Thr Gly Lys Lys Glu Met Glu Asn
    435                 440                 445 cag ctt gag agt atg gag gaa atg ttc ccg gac aag gtg agg gca gtt      1509
Gln Leu Glu Ser Met Glu Glu Met Phe Pro Asp Lys Val Arg Ala Val
450                 455                 460                 465 atg aag ttc aat gct ccc tta gct cac cag atg acg gcg gga gct gat      1557
Met Lys Phe Asn Ala Pro Leu Ala His Gln Met Thr Ala Gly Ala Asp
                470                 475                 480 ata att gtc att cca agt cga ttc gaa cca tgc ggc ctt atc cag ttg      1605
Ile Ile Val Ile Pro Ser Arg Phe Glu Pro Cys Gly Leu Ile Gln Leu
            485                 490                 495 caa ggc atg caa tat gga acg cct tct gcg tgt tcc tcc act ggt ggg      1653
Gln Gly Met Gln Tyr Gly Thr Pro Ser Ala Cys Ser Ser Thr Gly Gly
        500                 505                 510 ctt gtg gac acg gtg aaa gaa ggc aaa act gga ttc cat atg gga cct      1701
Leu Val Asp Thr Val Lys Glu Gly Lys Thr Gly Phe His Met Gly Pro
    515                 520                 525 ttc agt gct gaa tgc gaa gtg gtc gat ctt tct gat gta aag aaa gtt      1749
Phe Ser Ala Glu Cys Glu Val Val Asp Leu Ser Asp Val Lys Lys Val
530                 535                 540                 545 gtc aca act gtg aaa cgc gca ctt aag gtc atc ggc aca cct gcc ttt      1797
Val Thr Thr Val Lys Arg Ala Leu Lys Val Ile Gly Thr Pro Ala Phe
                550                 555                 560 gag gat atg atc aag aat tgc atg gca caa gac ctc tca tgg aag ggg      1845
Glu Asp Met Ile Lys Asn Cys Met Ala Gln Asp Leu Ser Trp Lys Gly
            565                 570                 575 cct gca aag aac tgg gag caa gtt cta ctg aac ttg gga gtt gcg gga      1893
Pro Ala Lys Asn Trp Glu Gln Val Leu Leu Asn Leu Gly Val Ala Gly
        580                 585                 590
```

```
agt gaa cca gga tat gat gga gaa gag att gtt cct ctt gct aag gaa    1941
Ser Glu Pro Gly Tyr Asp Gly Glu Glu Ile Val Pro Leu Ala Lys Glu
    595                 600                 605 aat gtg gca act cct tgaaattaaa cagctctata atctatgtat aaaccttgcc    1996
Asn Val Ala Thr Pro
610 gtggaaaaac tgatgtcatt gtaagtctct tcaggtgttc tcctcagcag gaggaaagaa    2056 tatctactgc agaaagaact atataaatat atatatatat atgataagta atatcttaat    2116 taagaactct ataattgctt gctttcacct cataattcgc tgaataaatc tctcgtactc    2176 ctattcctaa tttatgctgt atgttgtaaa tattgtgata caaatatagc taagtttcct    2236 tctaaaaaaa aaaaaaaaaa aaaaaaaaaa aaaaaaa                             2274

<210> SEQ ID NO 18
<211> LENGTH: 614
<212> TYPE: PRT
<213> ORGANISM: Typha latifolia

<400> SEQUENCE: 18

Met Ala Thr Val Thr Ala Ser Gln Phe Val Pro Lys Cys Leu Tyr Gly
1               5                   10                  15

Ser Ala Ala Asp Ser Asn Pro Arg Ala Phe His Asn Arg Lys Ile Ala
            20                  25                  30

Asp Leu Lys Asn Gln Ala Thr Ala Tyr His Gly Leu Arg Ser Gln Asn
        35                  40                  45

Ser Val Asp Leu Leu Gln Val Arg Thr Lys Ala Lys Thr Thr Ser Lys
    50                  55                  60

Gln Phe Lys Asn Gly Cys Ser Thr Val Asn Leu Arg Pro Pro Arg Ala
65                  70                  75                  80

Val Val Ile Cys Gly Lys Gly Met Asn Leu Val Phe Val Gly Ala Glu
                85                  90                  95

Met Ala Pro Trp Ser Lys Thr Gly Gly Leu Gly Asp Val Leu Gly Gly
            100                 105                 110

Leu Pro Pro Ala Leu Ala Ala Asn Gly His Arg Val Met Val Ile Ala
        115                 120                 125

Pro Arg Tyr Asp Gln Tyr Met Asp Ala Trp Asp Thr Asp Ala Leu Val
    130                 135                 140

Glu Leu Lys Val Gly Asp Arg Cys Glu Thr Val Arg Phe Phe His Cys
145                 150                 155                 160

Tyr Lys Arg Gly Val Asp Arg Val Phe Val Asp His Pro Met Phe Leu
                165                 170                 175

Ala Lys Val Trp Gly Lys Thr Gly Gly Lys Ile Tyr Gly Pro Asn Thr
            180                 185                 190

Gly Thr Asp Tyr Gln Asp Asn Gln Leu Arg Phe Ser Phe Leu Cys Gln
        195                 200                 205

Ala Ala Leu Glu Ala Pro Arg Ile Leu Asn Leu Asn Ser Asp Ser
    210                 215                 220

Phe Ser Gly Pro Tyr Gly Glu Asp Val Ile Phe Ile Cys Asn Asp Trp
225                 230                 235                 240

His Thr Ser Leu Leu Pro Cys Tyr Leu Lys Ser Met Tyr His Pro Arg
                245                 250                 255

Gly Ile Tyr Lys Asn Ala Lys Val Ala Phe Cys Ile His Asn Ile Ser
            260                 265                 270

Tyr Gln Gly Arg Phe Ser Pro Ser Asp Phe Glu Phe Leu Asn Leu Pro
        275                 280                 285
```

-continued

```
Glu Asn Phe Lys Ser Ser Phe Ser Phe Ile Asp Gly Tyr Asn Lys Pro
    290                 295                 300
Val Lys Gly Met Lys Ile Asn Trp Met Lys Ala Gly Ile Leu Glu Ser
305                 310                 315                 320
Asp Arg Val Phe Thr Val Ser Pro Tyr Tyr Ala Gln Glu Leu Leu Ser
                325                 330                 335
Gly Glu Glu Arg Gly Val Glu Leu Asp Asn Ile Leu Arg Val Thr Ser
            340                 345                 350
Ile Thr Gly Ile Val Asn Gly Met Asp Val Asn Glu Trp Asn Pro Leu
        355                 360                 365
Thr Asp Lys Tyr Ile Ser Val Asn Tyr Asp Ala Lys Pro Val Met Glu
    370                 375                 380
Ala Lys Pro Leu Asn Lys Glu Ala Leu Gln Ala Glu Ser Trp Leu Ala
385                 390                 395                 400
Cys Arg Gln Gly His Pro Cys Asn Cys Ile His Gly Arg Leu Glu Glu
                405                 410                 415
Gln Lys Gly Ser Asp Ile Leu Ala Ala Ser Ile Pro Glu Ile Met Asp
            420                 425                 430
Glu Asn Val Gln Leu Ile Ile Leu Gly Thr Gly Lys Lys Glu Met Glu
        435                 440                 445
Asn Gln Leu Glu Ser Met Glu Glu Met Phe Pro Asp Lys Val Arg Ala
    450                 455                 460
Val Met Lys Phe Asn Ala Pro Leu Ala His Gln Met Thr Ala Gly Ala
465                 470                 475                 480
Asp Ile Ile Val Ile Pro Ser Arg Phe Glu Pro Cys Gly Leu Ile Gln
                485                 490                 495
Leu Gln Gly Met Gln Tyr Gly Thr Pro Ser Ala Cys Ser Ser Thr Gly
            500                 505                 510
Gly Leu Val Asp Thr Val Lys Glu Gly Lys Thr Gly Phe His Met Gly
        515                 520                 525
Pro Phe Ser Ala Glu Cys Glu Val Val Asp Leu Ser Asp Val Lys Lys
    530                 535                 540
Val Val Thr Thr Val Lys Arg Ala Leu Lys Val Ile Gly Thr Pro Ala
545                 550                 555                 560
Phe Glu Asp Met Ile Lys Asn Cys Met Ala Gln Asp Leu Ser Trp Lys
                565                 570                 575
Gly Pro Ala Lys Asn Trp Glu Gln Val Leu Leu Asn Leu Gly Val Ala
            580                 585                 590
Gly Ser Glu Pro Gly Tyr Asp Gly Glu Glu Ile Val Pro Leu Ala Lys
        595                 600                 605
Glu Asn Val Ala Thr Pro
    610
```

<210> SEQ ID NO 19
<211> LENGTH: 25
<212> TYPE: DNA
<213> ORGANISM: Typha latifolia

<400> SEQUENCE: 19
atggctactg tgactgcatc acagt    25

<210> SEQ ID NO 20
<211> LENGTH: 25
<212> TYPE: DNA
<213> ORGANISM: Typha latifolia -continued

```
<400> SEQUENCE: 20
tcaaggagtt gccacatttt cctta                                          25

<210> SEQ ID NO 21
<211> LENGTH: 2067
<212> TYPE: DNA
<213> ORGANISM: Tulipa fosteriana
<220> FEATURE:
<221> NAME/KEY: CDS
<222> LOCATION: (58)...(1857)

<400> SEQUENCE: 21 ccaaaacct aacaaggtac ttcctcacca actctctaat cctagcagag aactcca atg    60
                                                                Met
                                                                 1 gct acc acg acg gcc gct ccg cat ttc atc atc tcc aag agt tgg tat    108
Ala Thr Thr Thr Ala Ala Pro His Phe Ile Ile Ser Lys Ser Trp Tyr
         5                  10                  15 gag ttg gag cca aaa ggg ttc atc aag agt ttg agc aac cca tcc ccc    156
Glu Leu Glu Pro Lys Gly Phe Ile Lys Ser Leu Ser Asn Pro Ser Pro
 20                  25                  30 ggc ttc cgc ggt ctg aga cct ctg aag ccg gtg ggt tcg ctg cag atg    204
Gly Phe Arg Gly Leu Arg Pro Leu Lys Pro Val Gly Ser Leu Gln Met
     35                  40                  45 cga ctc aac acg aaa tca acc ccc aaa gtt ggt agc tct gtc gtt gcg    252
Arg Leu Asn Thr Lys Ser Thr Pro Lys Val Gly Ser Ser Val Val Ala
 50                  55                  60                  65 cct acg gtc gaa act aca ggg atg aac ctg gtg ttc gtc ggg acc gag    300
Pro Thr Val Glu Thr Thr Gly Met Asn Leu Val Phe Val Gly Thr Glu
             70                  75                  80 acg ggt ccg tac agc aag acc ggc ggg ctc ggg gat gtg cta gga ggg    348
Thr Gly Pro Tyr Ser Lys Thr Gly Gly Leu Gly Asp Val Leu Gly Gly
         85                  90                  95 tta ccg ccc gcc ctg gcg gcg aga ggg cat cgg gtc atg gtt gtc act    396
Leu Pro Pro Ala Leu Ala Ala Arg Gly His Arg Val Met Val Val Thr
    100                 105                 110 ccg cgg tac gat cag tac aag gat gca tgg gac aca aac act gtg ctt    444
Pro Arg Tyr Asp Gln Tyr Lys Asp Ala Trp Asp Thr Asn Thr Val Leu
115                 120                 125 gag atc aaa gtc ggg gat aaa atg gag acg gtt cgt ttc ttc cac ctc    492
Glu Ile Lys Val Gly Asp Lys Met Glu Thr Val Arg Phe Phe His Leu
130                 135                 140                 145 cat aag agg ggg gtg gat agg gtg ttt att gat cac cct tgg ttt ctt    540
His Lys Arg Gly Val Asp Arg Val Phe Ile Asp His Pro Trp Phe Leu
                150                 155                 160 gag aag gtt tgg ggg aaa acc ggt ggg aaa ttg tat ggt cct gtt act    588
Glu Lys Val Trp Gly Lys Thr Gly Gly Lys Leu Tyr Gly Pro Val Thr
            165                 170                 175 gga act gat tat gat gat aac cag cta cgg ttc agt ctt ctg tgt cag    636
Gly Thr Asp Tyr Asp Asp Asn Gln Leu Arg Phe Ser Leu Leu Cys Gln
        180                 185                 190 gct gct ttg gag gct cca aga gtt cta aat ctc aac aac agt aaa tat    684
Ala Ala Leu Glu Ala Pro Arg Val Leu Asn Leu Asn Asn Ser Lys Tyr
    195                 200                 205 ttt tct gga cca tat ggt gaa gat gtc gtt ttt att gcg aac gat tgg    732
Phe Ser Gly Pro Tyr Gly Glu Asp Val Val Phe Ile Ala Asn Asp Trp
210                 215                 220                 225 cac act gga cct ctt cca tgc tac ttg aag agt gtg tat aaa tca gaa    780
His Thr Gly Pro Leu Pro Cys Tyr Leu Lys Ser Val Tyr Lys Ser Glu
                230                 235                 240
```

```
gga tta tat gag agt gcc aag gtt gcc ttt tgc att cat aat atg gca      828
Gly Leu Tyr Glu Ser Ala Lys Val Ala Phe Cys Ile His Asn Met Ala
            245                 250                 255 tac caa ggc aga ttc gcc ttt cct gat ttc tcg ctt ctc aac ctt cca      876
Tyr Gln Gly Arg Phe Ala Phe Pro Asp Phe Ser Leu Leu Asn Leu Pro
        260                 265                 270 gac aca ttt aaa tcc tcg ttt gat ttc ttc gat gga tat aca aaa cct      924
Asp Thr Phe Lys Ser Ser Phe Asp Phe Phe Asp Gly Tyr Thr Lys Pro
    275                 280                 285 gtg aaa ggt aga aaa ata aat tgg atg aag gct gga ata ttg gaa gcg      972
Val Lys Gly Arg Lys Ile Asn Trp Met Lys Ala Gly Ile Leu Glu Ala
290                 295                 300                 305 gac act gtt gta act gtg agc ccg tat tat gct aaa gag ctc gtc tct     1020
Asp Thr Val Val Thr Val Ser Pro Tyr Tyr Ala Lys Glu Leu Val Ser
            310                 315                 320 gga gaa gat aga ggt gtc gag ttg gac aac gtt ctg cgc ttg agg ggc     1068
Gly Glu Asp Arg Gly Val Glu Leu Asp Asn Val Leu Arg Leu Arg Gly
        325                 330                 335 gtc aaa gga att gtg aat ggg atg gat act aat gtg tgg aat cca ttg     1116
Val Lys Gly Ile Val Asn Gly Met Asp Thr Asn Val Trp Asn Pro Leu
    340                 345                 350 aca gac aaa ttt atc act gca aat tac gat gca aca atg gta aca gag     1164
Thr Asp Lys Phe Ile Thr Ala Asn Tyr Asp Ala Thr Met Val Thr Glu
355                 360                 365 gca aaa cgt gtt aat aag caa gaa tta caa gca gaa gtt ggc ttg cct     1212
Ala Lys Arg Val Asn Lys Gln Glu Leu Gln Ala Glu Val Gly Leu Pro
370                 375                 380                 385 gta gat cca gac att cct gtt ata gtt ttt gtt gga agg ctg gag gag     1260
Val Asp Pro Asp Ile Pro Val Ile Val Phe Val Gly Arg Leu Glu Glu
            390                 395                 400 cag aaa ggt tca gat att cta gct gca gca att cca gaa tta atg gat     1308
Gln Lys Gly Ser Asp Ile Leu Ala Ala Ala Ile Pro Glu Leu Met Asp
        405                 410                 415 gag aac gtt cag atc ata att ctt gga act ggc aag aaa cac ctc gaa     1356
Glu Asn Val Gln Ile Ile Ile Leu Gly Thr Gly Lys Lys His Leu Glu
    420                 425                 430 aag gag ctt gaa gaa ata gaa gaa caa ttt cca gac aag atg aga ctt     1404
Lys Glu Leu Glu Glu Ile Glu Glu Gln Phe Pro Asp Lys Met Arg Leu
435                 440                 445 gtt gcg aaa ttc aat gtt ccg ttg gct cat atg atg atg gct gga ggt     1452
Val Ala Lys Phe Asn Val Pro Leu Ala His Met Met Met Ala Gly Gly
450                 455                 460                 465 gat ttt ata ata att cct agt aga ttt gag ccg tgt ggg ctt att cag     1500
Asp Phe Ile Ile Ile Pro Ser Arg Phe Glu Pro Cys Gly Leu Ile Gln
            470                 475                 480 ctt gaa ggc atg aaa tat ggg atg cca gcc ata tgt tcc acc acc ggt     1548
Leu Glu Gly Met Lys Tyr Gly Met Pro Ala Ile Cys Ser Thr Thr Gly
        485                 490                 495 ggt ctt gta gac aca atc agg gaa ggc ttc acc gga ttt cac atg ggt     1596
Gly Leu Val Asp Thr Ile Arg Glu Gly Phe Thr Gly Phe His Met Gly
    500                 505                 510 gcc ttc act gtt gag tgt gaa act gtt gat ccg gtg gat gtg gcg gga     1644
Ala Phe Thr Val Glu Cys Glu Thr Val Asp Pro Val Asp Val Ala Gly
515                 520                 525 att gtt aaa act gta aag agg gcc ctt aag gtc tat gga act cca gcc     1692
Ile Val Lys Thr Val Lys Arg Ala Leu Lys Val Tyr Gly Thr Pro Ala
530                 535                 540                 545 ttc agc gaa atg gtt cag aac tgc atg gct caa gat cac tca tgg aag     1740
Phe Ser Glu Met Val Gln Asn Cys Met Ala Gln Asp His Ser Trp Lys
```

```
                550               555               560
gaa cct gca aaa aaa tgg gaa gag cta ctc ctg gga ctg gaa gtc gac      1788
Glu Pro Ala Lys Lys Trp Glu Glu Leu Leu Leu Gly Leu Glu Val Asp
            565               570               575 ggc agc gaa cct ggg ttt gat ggg gag gaa att gct cct ctt gca aag      1836
Gly Ser Glu Pro Gly Phe Asp Gly Glu Glu Ile Ala Pro Leu Ala Lys
        580               585               590 gaa aat gtg gct gct cca ttc tagtgatctg tatgccgtct tcaagccatc         1887
Glu Asn Val Ala Ala Pro Phe
    595               600 tcatgctaac atccttgagt cataaattta tgtattagtg agcccttccc ttatgttcag    1947
tgcttctatg ttagtggtgt atcattcatg agatgtataa tttctcgtgg aagtccagac    2007
ttgtaagaat aatctctttg ataaggcatg cagatcggat ataaaaaaaa aaaaaaaaaa    2067
```

<210> SEQ ID NO 22
<211> LENGTH: 600
<212> TYPE: PRT
<213> ORGANISM: Tulipa fosteriana

<400> SEQUENCE: 22

```
Met Ala Thr Thr Thr Ala Ala Pro His Phe Ile Ile Ser Lys Ser Trp
 1               5                  10                  15

Tyr Glu Leu Glu Pro Lys Gly Phe Ile Lys Ser Leu Ser Asn Pro Ser
            20                  25                  30

Pro Gly Phe Arg Gly Leu Arg Pro Leu Lys Pro Val Gly Ser Leu Gln
        35                  40                  45

Met Arg Leu Asn Thr Lys Ser Thr Pro Lys Val Gly Ser Ser Val Val
    50                  55                  60

Ala Pro Thr Val Glu Thr Thr Gly Met Asn Leu Val Phe Val Gly Thr
65                  70                  75                  80

Glu Thr Gly Pro Tyr Ser Lys Thr Gly Gly Leu Gly Asp Val Leu Gly
                85                  90                  95

Gly Leu Pro Pro Ala Leu Ala Ala Arg Gly His Arg Val Met Val Val
            100                 105                 110

Thr Pro Arg Tyr Asp Gln Tyr Lys Asp Ala Trp Asp Thr Asn Thr Val
        115                 120                 125

Leu Glu Ile Lys Val Gly Asp Lys Met Glu Thr Val Arg Phe Phe His
    130                 135                 140

Leu His Lys Arg Gly Val Asp Arg Val Phe Ile Asp His Pro Trp Phe
145                 150                 155                 160

Leu Glu Lys Val Trp Gly Lys Thr Gly Gly Lys Leu Tyr Gly Pro Val
                165                 170                 175

Thr Gly Thr Asp Tyr Asp Asp Asn Gln Leu Arg Phe Ser Leu Leu Cys
            180                 185                 190

Gln Ala Ala Leu Glu Ala Pro Arg Val Leu Asn Leu Asn Asn Ser Lys
        195                 200                 205

Tyr Phe Ser Gly Pro Tyr Gly Glu Asp Val Val Phe Ile Ala Asn Asp
    210                 215                 220

Trp His Thr Gly Pro Leu Pro Cys Tyr Leu Lys Ser Val Tyr Lys Ser
225                 230                 235                 240

Glu Gly Leu Tyr Glu Ser Ala Lys Val Ala Phe Cys Ile His Asn Met
                245                 250                 255

Ala Tyr Gln Gly Arg Phe Ala Phe Pro Asp Phe Ser Leu Leu Asn Leu
            260                 265                 270
```

```
Pro Asp Thr Phe Lys Ser Ser Phe Asp Phe Asp Gly Tyr Thr Lys
            275                 280                 285

Pro Val Lys Gly Arg Lys Ile Asn Trp Met Lys Ala Gly Ile Leu Glu
            290                 295                 300

Ala Asp Thr Val Val Thr Val Ser Pro Tyr Tyr Ala Lys Glu Leu Val
305                 310                 315                 320

Ser Gly Glu Asp Arg Gly Val Glu Leu Asp Asn Val Leu Arg Leu Arg
            325                 330                 335

Gly Val Lys Gly Ile Val Asn Gly Met Asp Thr Asn Val Trp Asn Pro
            340                 345                 350

Leu Thr Asp Lys Phe Ile Thr Ala Asn Tyr Asp Ala Thr Met Val Thr
            355                 360                 365

Glu Ala Lys Arg Val Asn Lys Gln Glu Leu Gln Ala Glu Val Gly Leu
            370                 375                 380

Pro Val Asp Pro Asp Ile Pro Val Ile Val Phe Val Gly Arg Leu Glu
385                 390                 395                 400

Glu Gln Lys Gly Ser Asp Ile Leu Ala Ala Ala Ile Pro Glu Leu Met
            405                 410                 415

Asp Glu Asn Val Gln Ile Ile Leu Gly Thr Gly Lys Lys His Leu
            420                 425                 430

Glu Lys Glu Leu Glu Glu Ile Glu Glu Gln Phe Pro Asp Lys Met Arg
            435                 440                 445

Leu Val Ala Lys Phe Asn Val Pro Leu Ala His Met Met Met Ala Gly
450                 455                 460

Gly Asp Phe Ile Ile Ile Pro Ser Arg Phe Glu Pro Cys Gly Leu Ile
465                 470                 475                 480

Gln Leu Glu Gly Met Lys Tyr Gly Met Pro Ala Ile Cys Ser Thr Thr
            485                 490                 495

Gly Gly Leu Val Asp Thr Ile Arg Glu Gly Phe Thr Gly Phe His Met
            500                 505                 510

Gly Ala Phe Thr Val Glu Cys Glu Thr Val Asp Pro Val Asp Val Ala
            515                 520                 525

Gly Ile Val Lys Thr Val Lys Arg Ala Leu Lys Val Tyr Gly Thr Pro
            530                 535                 540

Ala Phe Ser Glu Met Val Gln Asn Cys Met Ala Gln Asp His Ser Trp
545                 550                 555                 560

Lys Glu Pro Ala Lys Lys Trp Glu Glu Leu Leu Leu Gly Leu Glu Val
            565                 570                 575

Asp Gly Ser Glu Pro Gly Phe Asp Gly Glu Glu Ile Ala Pro Leu Ala
            580                 585                 590

Lys Glu Asn Val Ala Ala Pro Phe
            595                 600

<210> SEQ ID NO 23
<211> LENGTH: 25
<212> TYPE: DNA
<213> ORGANISM: Tulipa fosteriana

<400> SEQUENCE: 23
atggctacca cgacggccgc tccgc                                          25

<210> SEQ ID NO 24
<211> LENGTH: 25
<212> TYPE: DNA
<213> ORGANISM: Tulipa fosteriana
```

-continued

```
<400> SEQUENCE: 24
ctagaatgga gcagccacat tttcc                                              25

<210> SEQ ID NO 25
<211> LENGTH: 2418
<212> TYPE: DNA
<213> ORGANISM: Typha latifolia
<220> FEATURE:
<221> NAME/KEY: CDS
<222> LOCATION: (1)...(2418)

<400> SEQUENCE: 25 atg agt gtt ggt aaa gcc agg tct ttt aga gtc aga aag cgt gaa agc         48
Met Ser Val Gly Lys Ala Arg Ser Phe Arg Val Arg Lys Arg Glu Ser
1               5                   10                  15 ttg gtg ggt ctg cga gcc act ggg aaa agt ggt agc ttt gaa gag gaa         96
Leu Val Gly Leu Arg Ala Thr Gly Lys Ser Gly Ser Phe Glu Glu Glu
            20                  25                  30 ggg gag gag aga gag ggt gtt ggt cgt gcg ggt gtt ggt gat gat gct        144
Gly Glu Glu Arg Glu Gly Val Gly Arg Ala Gly Val Gly Asp Asp Ala
        35                  40                  45 ctt cgt gca acg att gat aag agc aat gag att ctt gca atc cac agt        192
Leu Arg Ala Thr Ile Asp Lys Ser Asn Glu Ile Leu Ala Ile His Ser
    50                  55                  60 aac cta ctt caa cag att gca aaa aga aag aat att gtt tca tca atc        240
Asn Leu Leu Gln Gln Ile Ala Lys Arg Lys Asn Ile Val Ser Ser Ile
65                  70                  75                  80 aga agt gac gta act aag gaa gaa aat gat tca agt tct tat gtt gag        288
Arg Ser Asp Val Thr Lys Glu Glu Asn Asp Ser Ser Ser Tyr Val Glu
                85                  90                  95 aag gaa aat ttg gag cca agc agt gga gag caa aat ggg aag tac aaa        336
Lys Glu Asn Leu Glu Pro Ser Ser Gly Glu Gln Asn Gly Lys Tyr Lys
            100                 105                 110 agc ggc gcc gtt cct aat aat tat tcc caa ttg gct caa gat gat aca        384
Ser Gly Ala Val Pro Asn Asn Tyr Ser Gln Leu Ala Gln Asp Asp Thr
        115                 120                 125 tct gag aat cca ctt gtt aat tcc ttt gga ggt tct cca aaa gat aac        432
Ser Glu Asn Pro Leu Val Asn Ser Phe Gly Gly Ser Pro Lys Asp Asn
    130                 135                 140 gta gaa gct gtt gaa ttt cag gtg aga caa tca gca gta gat gct ttt        480
Val Glu Ala Val Glu Phe Gln Val Arg Gln Ser Ala Val Asp Ala Phe
145                 150                 155                 160 gga aga cct gaa gaa ccc agt ttg ggg acg acg aag att ctc tca cca        528
Gly Arg Pro Glu Glu Pro Ser Leu Gly Thr Thr Lys Ile Leu Ser Pro
                165                 170                 175 ttt tat ctt gaa gct gaa tct gat ggt gct aaa gaa gag aat gct gaa        576
Phe Tyr Leu Glu Ala Glu Ser Asp Gly Ala Lys Glu Glu Asn Ala Glu
            180                 185                 190 gat ctt gta gaa gca aaa ttg gat agt gta cat gtc aaa gat gat ttg        624
Asp Leu Val Glu Ala Lys Leu Asp Ser Val His Val Lys Asp Asp Leu
        195                 200                 205 aat cct ggg gaa gaa aat gag gtt cct ctt cct ttg gct ggg gca aat        672
Asn Pro Gly Glu Glu Asn Glu Val Pro Leu Pro Leu Ala Gly Ala Asn
    210                 215                 220 gtc atg aac atc ata gta gtt gct gca gaa tgt gct cct tgg tcc aaa        720
Val Met Asn Ile Ile Val Val Ala Ala Glu Cys Ala Pro Trp Ser Lys
225                 230                 235                 240 aca ggt ggg ctt gga gat gtt gca gga gca ttg ccg aag gct ttg gcc        768
Thr Gly Gly Leu Gly Asp Val Ala Gly Ala Leu Pro Lys Ala Leu Ala
                245                 250                 255
```

-continued

| | |
|---|---|
| aga aga gga cat agg gtc atg gtt gtg gca cca agg tat gga aac tat<br>Arg Arg Gly His Arg Val Met Val Val Ala Pro Arg Tyr Gly Asn Tyr<br>            260                    265                  270 | 816 |
| gct gaa ccc caa gat ata gga gtc cgc aaa tac tac aag gtt cat ggg<br>Ala Glu Pro Gln Asp Ile Gly Val Arg Lys Tyr Tyr Lys Val His Gly<br>        275                    280                    285 | 864 |
| cag gat atg gaa gta act tat ttc cat gct tat atc gac ggt gtg gat<br>Gln Asp Met Glu Val Thr Tyr Phe His Ala Tyr Ile Asp Gly Val Asp<br>290                    295                    300 | 912 |
| ttt gtt ttt atg gat agt cca gac ttc cgt cac cgg ggg aat cgt att<br>Phe Val Phe Met Asp Ser Pro Asp Phe Arg His Arg Gly Asn Arg Ile<br>305                    310                    315                  320 | 960 |
| tat gag gga aac cga gtg gat atc tta aaa cgt atg att ttg ttc tgc<br>Tyr Glu Gly Asn Arg Val Asp Ile Leu Lys Arg Met Ile Leu Phe Cys<br>            325                    330                    335 | 1008 |
| aag gca gct gta gag gtt cct tgg cat gtt cca tgt ggt ggc ttc tgt<br>Lys Ala Ala Val Glu Val Pro Trp His Val Pro Cys Gly Gly Phe Cys<br>                340                    345                    350 | 1056 |
| tat gga gat ggt aat ttg gct ttc atc acg aat gat tgg cat act gct<br>Tyr Gly Asp Gly Asn Leu Ala Phe Ile Thr Asn Asp Trp His Thr Ala<br>        355                    360                    365 | 1104 |
| ctc ttg cct gtt tat ctg aag gca tat tat cgt gac aat ggc ttg atg<br>Leu Leu Pro Val Tyr Leu Lys Ala Tyr Tyr Arg Asp Asn Gly Leu Met<br>370                    375                    380 | 1152 |
| aaa tat gct cgg tct gtt ctg gta ata cac aac ata gcc cac cag ggt<br>Lys Tyr Ala Arg Ser Val Leu Val Ile His Asn Ile Ala His Gln Gly<br>385                    390                    395                  400 | 1200 |
| cgt ggt cct gta gat gac ttc aaa ttt gtg ggc ttg ccg gat cac tac<br>Arg Gly Pro Val Asp Asp Phe Lys Phe Val Gly Leu Pro Asp His Tyr<br>                405                    410                    415 | 1248 |
| ttg gac ctt ttc aga ttg tat gac ccc gtc gga ggt gaa cac ctc aat<br>Leu Asp Leu Phe Arg Leu Tyr Asp Pro Val Gly Gly Glu His Leu Asn<br>            420                    425                    430 | 1296 |
| att ttt gct gct ggc ctg aag act gct gac cga gtg gtt act gtt agc<br>Ile Phe Ala Ala Gly Leu Lys Thr Ala Asp Arg Val Val Thr Val Ser<br>                435                    440                    445 | 1344 |
| cat ggt tat gca tgg gag ctg aaa aca tca gaa ggt ggt tgg ggc cta<br>His Gly Tyr Ala Trp Glu Leu Lys Thr Ser Glu Gly Gly Trp Gly Leu<br>        450                    455                    460 | 1392 |
| cat gaa att ata aat gaa agt aac tgg aag ttt caa ggt att gta aat<br>His Glu Ile Ile Asn Glu Ser Asn Trp Lys Phe Gln Gly Ile Val Asn<br>465                    470                    475                  480 | 1440 |
| ggc att gat gca aag gag tgg agc ccc gaa ttt gat gtg cac ctt aaa<br>Gly Ile Asp Ala Lys Glu Trp Ser Pro Glu Phe Asp Val His Leu Lys<br>                485                    490                    495 | 1488 |
| tcc gat gga tac aca aat tat tct cta gat act tta gag atg ggt aag<br>Ser Asp Gly Tyr Thr Asn Tyr Ser Leu Asp Thr Leu Glu Met Gly Lys<br>        500                    505                    510 | 1536 |
| cca gta tgt aag gct gct ttg cag cga gag gtc ggt ctg cct gtt cgt<br>Pro Val Cys Lys Ala Ala Leu Gln Arg Glu Val Gly Leu Pro Val Arg<br>            515                    520                    525 | 1584 |
| gat aat gta ccc atc att gca ttc att gga agg tta gac cac cag aaa<br>Asp Asn Val Pro Ile Ile Ala Phe Ile Gly Arg Leu Asp His Gln Lys<br>530                    535                    540 | 1632 |
| ggc gtc gat ctc att gcc gag gcc atg cct tgg att gtc agt cat gat<br>Gly Val Asp Leu Ile Ala Glu Ala Met Pro Trp Ile Val Ser His Asp<br>545                    550                    555                  560 | 1680 |
| gtt caa gta gtc atg tta ggc acg ggg agg caa gac ctt gag aat tta<br>Val Gln Val Val Met Leu Gly Thr Gly Arg Gln Asp Leu Glu Asn Leu<br>            565                    570                    575 | 1728 |

-continued

```
ctg agg aac ttt gag ggt caa cac agg gac aaa gtt aga gca tgg gtt    1776
Leu Arg Asn Phe Glu Gly Gln His Arg Asp Lys Val Arg Ala Trp Val
            580                 585                 590 gca ttt tca gta aag atg gcg cat aga att aca gca ggt gcc gac atc    1824
Ala Phe Ser Val Lys Met Ala His Arg Ile Thr Ala Gly Ala Asp Ile
        595                 600                 605 ctc atg atg cct tcg agg ttt gag cca tgc gga ttg aac cag ctt tac    1872
Leu Met Met Pro Ser Arg Phe Glu Pro Cys Gly Leu Asn Gln Leu Tyr
    610                 615                 620 gca atg atg tat gga acc att cca gtg gtg cat gct gtt ggg ggc ctt    1920
Ala Met Met Tyr Gly Thr Ile Pro Val Val His Ala Val Gly Gly Leu
625                 630                 635                 640 aga gat aca gtg act caa ttt gat cct ttc aac gag tct ggt ctt ggt    1968
Arg Asp Thr Val Thr Gln Phe Asp Pro Phe Asn Glu Ser Gly Leu Gly
                645                 650                 655 tgg acc ttc gac agg gca gag gca gga aag ctg atc cat gca ttg aat    2016
Trp Thr Phe Asp Arg Ala Glu Ala Gly Lys Leu Ile His Ala Leu Asn
            660                 665                 670 aac tgc ttg aat aca tac tgg aat tac aag gac agt tgg aag ggt ctt    2064
Asn Cys Leu Asn Thr Tyr Trp Asn Tyr Lys Asp Ser Trp Lys Gly Leu
        675                 680                 685 caa aca aga ggg atg atg caa gat ctt agc tgg gat aat gct gct cag    2112
Gln Thr Arg Gly Met Met Gln Asp Leu Ser Trp Asp Asn Ala Ala Gln
    690                 695                 700 caa tac gag gat gtc ctt gtt gca gcc aag tac caa tgg tga ttc ttc    2160
Gln Tyr Glu Asp Val Leu Val Ala Ala Lys Tyr Gln Trp     Phe Phe
705                 710                 715 tcc atc aca tgt gtg tta att gag atc tat cga gag atg atg ata atg    2208
Ser Ile Thr Cys Val Leu Ile Glu Ile Tyr Arg Glu Met Met Ile Met
720                 725                 730                 735 gtc tat atg tga gat cat agt ttc aga tat gcg gca gca tgc aaa tag    2256
Val Tyr Met     Asp His Ser Phe Arg Tyr Ala Ala Ala Cys Lys
                740                 745 atg aaa ttt ttt tgg ctc atg ctg gaa cat gta aat tgt ttc tct ttt    2304
Met Lys Phe Phe Trp Leu Met Leu Glu His Val Asn Cys Phe Ser Phe
750                 755                 760                 765 ttt cca ttt ttg ccc tgc act ctg tac aga gga agg agg aaa caa ttg    2352
Phe Pro Phe Leu Pro Cys Thr Leu Tyr Arg Gly Arg Arg Lys Gln Leu
                770                 775                 780 ctg aaa act gtg gag gtc tgt gta ccc tat att tct agc ttt tat taa    2400
Leu Lys Thr Val Glu Val Cys Val Pro Tyr Ile Ser Ser Phe Tyr
            785                 790                 795 tgc aag tag ttc ttc gtt                                             2418
Cys Lys     Phe Phe Val
                800
```

<210> SEQ ID NO 26
<211> LENGTH: 801
<212> TYPE: PRT
<213> ORGANISM: Typha latifolia

<400> SEQUENCE: 26

```
Met Ser Val Gly Lys Ala Arg Ser Phe Arg Val Arg Lys Arg Glu Ser
 1               5                  10                  15

Leu Val Gly Leu Arg Ala Thr Gly Lys Ser Gly Ser Phe Glu Glu Glu
            20                  25                  30

Gly Glu Glu Arg Glu Gly Val Gly Arg Ala Gly Val Gly Asp Asp Ala
        35                  40                  45

Leu Arg Ala Thr Ile Asp Lys Ser Asn Glu Ile Leu Ala Ile His Ser
```

```
                    50                       55                       60
Asn Leu Leu Gln Gln Ile Ala Lys Arg Lys Asn Ile Val Ser Ser Ile
 65                      70                       75                   80

Arg Ser Asp Val Thr Lys Glu Asn Asp Ser Ser Tyr Val Glu
                     85                       90                   95

Lys Glu Asn Leu Glu Pro Ser Ser Gly Glu Gln Asn Gly Lys Tyr Lys
                    100                      105                  110

Ser Gly Ala Val Pro Asn Asn Tyr Ser Gln Leu Ala Gln Asp Asp Thr
                    115                      120                  125

Ser Glu Asn Pro Leu Val Asn Ser Phe Gly Gly Ser Pro Lys Asp Asn
                    130                      135              140

Val Glu Ala Val Glu Phe Gln Val Arg Gln Ser Ala Val Asp Ala Phe
145                      150                      155                 160

Gly Arg Pro Glu Glu Pro Ser Leu Gly Thr Thr Lys Ile Leu Ser Pro
                    165                      170                  175

Phe Tyr Leu Glu Ala Glu Ser Asp Gly Ala Lys Glu Glu Asn Ala Glu
                    180                      185                  190

Asp Leu Val Glu Ala Lys Leu Asp Ser Val His Val Lys Asp Asp Leu
                    195                      200                  205

Asn Pro Gly Glu Glu Asn Glu Val Pro Leu Pro Leu Ala Gly Ala Asn
                    210                      215              220

Val Met Asn Ile Ile Val Val Ala Ala Glu Cys Ala Pro Trp Ser Lys
225                      230                      235                 240

Thr Gly Gly Leu Gly Asp Val Ala Gly Ala Leu Pro Lys Ala Leu Ala
                    245                      250                  255

Arg Arg Gly His Arg Val Met Val Val Ala Pro Arg Tyr Gly Asn Tyr
                    260                      265                  270

Ala Glu Pro Gln Asp Ile Gly Val Arg Lys Tyr Tyr Lys Val His Gly
                    275                      280                  285

Gln Asp Met Glu Val Thr Tyr Phe His Ala Tyr Ile Asp Gly Val Asp
                    290                      295              300

Phe Val Phe Met Asp Ser Pro Asp Phe Arg His Arg Gly Asn Arg Ile
305                      310                      315                 320

Tyr Glu Gly Asn Arg Val Asp Ile Leu Lys Arg Met Ile Leu Phe Cys
                    325                      330                  335

Lys Ala Ala Val Glu Val Pro Trp His Val Pro Cys Gly Gly Phe Cys
                    340                      345                  350

Tyr Gly Asp Gly Asn Leu Ala Phe Ile Thr Asn Asp Trp His Thr Ala
                    355                      360              365

Leu Leu Pro Val Tyr Leu Lys Ala Tyr Tyr Arg Asp Asn Gly Leu Met
                    370                      375                  380

Lys Tyr Ala Arg Ser Val Leu Val Ile His Asn Ile Ala His Gln Gly
385                      390                      395                 400

Arg Gly Pro Val Asp Asp Phe Lys Phe Val Gly Leu Pro Asp His Tyr
                    405                      410                  415

Leu Asp Leu Phe Arg Leu Tyr Asp Pro Val Gly Gly Glu His Leu Asn
                    420                      425              430

Ile Phe Ala Ala Gly Leu Lys Thr Ala Asp Arg Val Val Thr Val Ser
                    435                      440                  445

His Gly Tyr Ala Trp Glu Leu Lys Thr Ser Glu Gly Gly Trp Gly Leu
                    450                      455                  460

His Glu Ile Ile Asn Glu Ser Asn Trp Lys Phe Gln Gly Ile Val Asn
465                      470                      475                 480
```

```
Gly Ile Asp Ala Lys Glu Trp Ser Pro Glu Phe Asp Val His Leu Lys
            485                 490                 495
Ser Asp Gly Tyr Thr Asn Tyr Ser Leu Asp Thr Leu Glu Met Gly Lys
            500                 505                 510
Pro Val Cys Lys Ala Ala Leu Gln Arg Glu Val Gly Leu Pro Val Arg
            515                 520                 525
Asp Asn Val Pro Ile Ile Ala Phe Ile Gly Arg Leu Asp His Gln Lys
            530                 535                 540
Gly Val Asp Leu Ile Ala Glu Ala Met Pro Trp Ile Val Ser His Asp
545                 550                 555                 560
Val Gln Val Val Met Leu Gly Thr Gly Arg Gln Asp Leu Glu Asn Leu
                565                 570                 575
Leu Arg Asn Phe Glu Gly Gln His Arg Asp Lys Val Arg Ala Trp Val
                580                 585                 590
Ala Phe Ser Val Lys Met Ala His Arg Ile Thr Ala Gly Ala Asp Ile
                595                 600                 605
Leu Met Met Pro Ser Arg Phe Glu Pro Cys Gly Leu Asn Gln Leu Tyr
            610                 615                 620
Ala Met Met Tyr Gly Thr Ile Pro Val Val His Ala Val Gly Gly Leu
625                 630                 635                 640
Arg Asp Thr Val Thr Gln Phe Asp Pro Phe Asn Glu Ser Gly Leu Gly
                645                 650                 655
Trp Thr Phe Asp Arg Ala Glu Ala Gly Lys Leu Ile His Ala Leu Asn
                660                 665                 670
Asn Cys Leu Asn Thr Tyr Trp Asn Tyr Lys Asp Ser Trp Lys Gly Leu
            675                 680                 685
Gln Thr Arg Gly Met Met Gln Asp Leu Ser Trp Asp Asn Ala Ala Gln
            690                 695                 700
Gln Tyr Glu Asp Val Leu Val Ala Ala Lys Tyr Gln Trp Phe Phe Ser
705                 710                 715                 720
Ile Thr Cys Val Leu Ile Glu Ile Tyr Arg Glu Met Met Ile Met Val
                725                 730                 735
Tyr Met Asp His Ser Phe Arg Tyr Ala Ala Ala Cys Lys Met Lys Phe
                740                 745                 750
Phe Trp Leu Met Leu Glu His Val Asn Cys Phe Ser Phe Phe Pro Phe
            755                 760                 765
Leu Pro Cys Thr Leu Tyr Arg Gly Arg Arg Lys Gln Leu Leu Lys Thr
            770                 775                 780
Val Glu Val Cys Val Pro Tyr Ile Ser Ser Phe Tyr Cys Lys Phe Phe
785                 790                 795                 800
Val
```

<210> SEQ ID NO 27
<211> LENGTH: 23
<212> TYPE: DNA
<213> ORGANISM: Typha latifolia

<400> SEQUENCE: 27
atgagtgttg gtaaagccag gtc                                           23

<210> SEQ ID NO 28
<211> LENGTH: 24

-continued

```
<212> TYPE: DNA
<213> ORGANISM: Typha latifolia

<400> SEQUENCE: 28
tcaccattgg tacttggctg caac                                              24
```